US012207859B2

(12) United States Patent
Wiltberger et al.

(10) Patent No.: US 12,207,859 B2
(45) Date of Patent: *Jan. 28, 2025

(54) SYSTEMS FOR INCISING TISSUE

(71) Applicant: INSIGHTFUL INSTRUMENTS, INC., Santa Clara, CA (US)

(72) Inventors: Michael W. Wiltberger, Santa Clara, CA (US); Phillip Gooding, Mountain View, CA (US); Dan E. Andersen, Menlo Park, CA (US)

(73) Assignee: INSIGHTFUL INSTRUMENTS, INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/747,645

(22) Filed: Jun. 19, 2024

(65) Prior Publication Data
US 2024/0335224 A1 Oct. 10, 2024

Related U.S. Application Data

(63) Continuation of application No. 18/390,759, filed on Dec. 20, 2023, now Pat. No. 12,053,220, which is a
(Continued)

(51) Int. Cl.
*A61B 18/14* (2006.01)
*A61B 18/04* (2006.01)
(Continued)

(52) U.S. Cl.
CPC .... *A61B 18/042* (2013.01); *A61B 2018/0019* (2013.01); *A61B 2018/00601* (2013.01);
(Continued)

(58) Field of Classification Search
CPC ........... H05H 2245/30; H05H 2245/32; H05H 2245/34; A61B 18/042; A61B 2018/144;
(Continued)

(56) References Cited

U.S. PATENT DOCUMENTS 4,542,742 A 9/1985 Winkelman
5,215,104 A 6/1993 Steinert
(Continued)

FOREIGN PATENT DOCUMENTS

CN 208426205 1/2019
JP H11501555 2/1999
(Continued)

OTHER PUBLICATIONS

Ağca, Alper, et al. "Comparison of Visual Acuity and Higher-Order Aberrations after Femtosecond Lenticule Extraction and Small-Incision Lenticule Extraction." Contact Lens and Anterior Eye, vol. 37, No. 4, Aug. 2014, pp. 292-296, doi: 10/gh2btw.
(Continued)

*Primary Examiner* — Sean W Collins
(74) *Attorney, Agent, or Firm* — FisherBroyles, LLP; John K. Shimmick

(57) ABSTRACT

An elongate electrode is configured to flex and generate plasma to incise tissue. An electrical energy source operatively coupled to the electrode is configured to provide electrical energy to the electrode to generate the plasma. A tensioning element is operatively coupled to the elongate electrode. The tensioning element can be configured to provide tension to the elongate electrode to allow the elongate electrode to flex in response to the elongate electrode engaging the tissue and generating the plasma. The tensioning element operatively coupled to the flexible elongate electrode may allow for the use of a small diameter electrode, such as a 5 μm to 20 μm diameter electrode, which can allow narrow incisions to be formed with decreased tissue damage. In some embodiments, the tensioning of the electrode allows the electrode to more accurately incise tissue by decreasing variations in the position of the electrode along the incision path.

19 Claims, 28 Drawing Sheets

Related U.S. Application Data continuation of application No. 17/935,401, filed on Sep. 26, 2022, now Pat. No. 11,896,283, which is a continuation of application No. 17/250,965, filed as application No. PCT/US2020/070757 on Nov. 6, 2020, now Pat. No. 11,490,948.

(60) Provisional application No. 62/966,925, filed on Jan. 28, 2020, provisional application No. 62/931,226, filed on Nov. 6, 2019.

(51) Int. Cl.
   - A61B 18/00 (2006.01)
   - A61F 9/007 (2006.01)
   - H05H 1/46 (2006.01)

(52) U.S. Cl.
   CPC ..... *A61B 2018/144* (2013.01); *A61F 9/00781* (2013.01); *A61F 9/0079* (2013.01); *H05H 1/466* (2021.05); *H05H 2245/32* (2021.05)

(58) Field of Classification Search
   CPC .... A61B 2018/1213; A61B 2018/1407; A61B 2018/122; A61F 9/0079
   See application file for complete search history.

(56) References Cited

U.S. PATENT DOCUMENTS

| | | | |
|---|---|---|---|
| 5,556,406 A | 9/1996 | Gordon | |
| 5,683,366 A * | 11/1997 | Eggers | A61B 18/1482 604/114 |
| 5,833,701 A | 11/1998 | Gordon | |
| 6,312,440 B1 | 11/2001 | Hood | |
| 6,358,260 B1 | 3/2002 | Ross | |
| 6,730,075 B2 | 5/2004 | Palanker | |
| 6,780,178 B2 | 8/2004 | Palanker | |
| 7,238,185 B2 | 7/2007 | Palanker | |
| 7,357,802 B2 | 4/2008 | Palanker | |
| 7,789,879 B2 | 9/2010 | Palanker | |
| 7,922,735 B2 | 4/2011 | Daxer | |
| 8,043,286 B2 | 10/2011 | Palanker | |
| 8,088,126 B2 | 1/2012 | Fugo | |
| 8,177,783 B2 | 5/2012 | Davison | |
| 8,292,877 B2 | 10/2012 | Raksi | |
| 8,323,276 B2 | 12/2012 | Palanker | |
| 8,414,572 B2 | 4/2013 | Davison | |
| 8,870,864 B2 | 10/2014 | Davison | |
| 9,018,983 B2 | 4/2015 | Vankov | |
| 11,490,948 B2 | 11/2022 | Wiltberger | |
| 11,896,283 B2 | 2/2024 | Wiltberger | |
| 12,053,220 B1 | 8/2024 | Wiltberger | |
| 2001/0025117 A1 | 9/2001 | Hong | |
| 2001/0025177 A1* | 9/2001 | Woloszko | A61B 18/1492 606/41 |
| 2003/0084907 A1 | 5/2003 | Pacek | |
| 2006/0064113 A1 | 3/2006 | Nakao | |
| 2007/0280994 A1 | 12/2007 | Cunanan | |
| 2007/0282328 A1 | 12/2007 | Yahagi | |
| 2008/0021444 A1 | 1/2008 | Scoption | |
| 2008/0039832 A1 | 2/2008 | Palanker | |
| 2008/0125774 A1 | 5/2008 | Palanker | |
| 2008/0281303 A1 | 11/2008 | Culbertson | |
| 2009/0187184 A1 | 7/2009 | Muller | |
| 2009/0301860 A1 | 12/2009 | Iida | |
| 2011/0190741 A1 | 8/2011 | Deisinger | |
| 2011/0276089 A1 | 11/2011 | Straehnz | |
| 2011/0301637 A1 | 12/2011 | Kerr | |
| 2011/0313344 A1* | 12/2011 | Daxer | A61F 9/0133 606/166 |
| 2012/0245580 A1 | 9/2012 | Germain | |
| 2015/0282822 A1 | 10/2015 | Trees | |
| 2015/0297257 A1 | 10/2015 | Galer | |
| 2015/0297280 A1 | 10/2015 | Li | |
| 2016/0074226 A1 | 3/2016 | Spooner | |
| 2017/0105797 A1 | 4/2017 | Mikkaichi | |
| 2017/0333114 A1* | 11/2017 | Atwell | A61B 18/1445 |
| 2019/0328377 A1 | 10/2019 | Johnson | |
| 2020/0254270 A1 | 8/2020 | Wandke | |

FOREIGN PATENT DOCUMENTS

| | | | |
|---|---|---|---|
| JP | 2019503228 | 2/2019 | |
| WO | 1997018765 | 5/1997 | |
| WO | WO-0009055 A1 * | 2/2000 | A61F 9/013 |
| WO | 2017124062 | 7/2017 | |
| WO | 2021092628 | 5/2021 | |

OTHER PUBLICATIONS

Ang, Marcus, et al. "Small Incision Lenticule Extraction (SMILE) versus Laser in-Situ Keratomileusis (LASIK): Study Protocol for a Randomized, Non-Inferiority Trial." Trials, vol. 13, May 2012, p. 75, doi:10/gbbgv5.

Ganesh, Sri, et al. "Refractive Lenticule Extraction Small Incision Lenticule Extraction: A New Refractive Surgery Paradigm." Indian Journal of Ophthalmology, vol. 66, No. 1, Jan. 2018, pp. 10-19, doi:10/gcrf6z.

Gyldenkerne, Anders, et al. "Comparison of Corneal Shape Changes and Aberrations Induced by FS-LASIK and SMILE for Myopia." Journal of Refractive Surgery, Mar. 2015, doi:10/f684jm.

Hammer, D. X., et al. "Experimental Investigation of Ultrashort Pulse Laser-Induced Breakdown Thresholds in Aqueous Media." IEEE Journal of Quantum Electronics, vol. 32, No. 4, Apr. 1996, pp. 670-678, doi:10.1109/3.488842.

International Search Report and Written Opinion for PCT/US2020/070757, 10 pages (Mar. 23, 2021).

Lombardo, Marco, and Giuseppe Lombardo. "Wave Aberration of Human Eyes and New Descriptors of Image Optical Quality and Visual Performance." Journal of Cataract & Refractive Surgery, vol. 36, No. 2, Feb. 2010, pp. 313-331, doi:10.1016/j.jcrs.2009.09.026.

Palanker, D. V., et al. "Pulsed Electron Avalanche Knife (PEAK) for Intraocular Surgery." Investigative Ophthalmology & Visual Science, vol. 42, No. 11, Oct. 2001, pp. 2673-2678.

Pallikaris, I. G., et al. "Laser in Situ Keratomileusis." Lasers in Surgery and Medicine, vol. 10, No. 5, 1990, pp. 463-468, doi:10/cpjdwq.

Peponis, Vasileios, et al. "The Use of the Fugo Blade in Corneal Surgery: A Preliminary Animal Study." Cornea, vol. 25, No. 2, Feb. 2006, pp. 206-208, doi: 10.1097/01.ico.0000179927.12899.bb.

Reinstein, Dan Z., et al. "Small Incision Lenticule Extraction (SMILE) History, Fundamentals of a New Refractive Surgery Technique and Clinical Outcomes." Eye and Vision, vol. 1, No. 1, Dec. 2014, p. 3, doi:10/gh2btx.

Sekundo W., Chapters 1, 6, 13, 15, and 19, from "Small Incision Lenticule Extraction (SMILE) Principles, Techniques, Complication Management, and Future Concepts," 65 pages (2015).

Shen, Yang, et al. "Comparison of Corneal Deformation Parameters After Smile, Lasek, and Femtosecond Laser-Assisted LASIK." Journal of Refractive Surgery, vol. 30, No. 5, May 2014, pp. 310-318, doi: 10/f56ckn.

Shen, Zeren, et al. "Small Incision Lenticule Extraction (SMILE) versus Femtosecond Laser-Assisted In Situ Keratomileusis (FS-LASIK) for Myopia: A Systematic Review and Meta-Analysis." PloS One, vol. 11, No. 7, 2016, p. e0158176, doi:10/gbnfgj.

* cited by examiner

SYSTEMS FOR INCISING TISSUE

RELATED APPLICATIONS

This application is a continuation of U.S. patent application Ser. No. 18/390,759, filed Dec. 20, 2023, now U.S. Pat. No. 12,053,220, issued Aug. 6, 2024, which is a continuation of U.S. patent application Ser. No. 17/935,401, filed Sep. 26, 2022, now U.S. Pat. No. 11,896,283, issued Feb. 13, 2024, which is a continuation of U.S. patent application Ser. No. 17/250,965, filed Apr. 2, 2021, now U.S. Pat. No. 11,490,948, issued Nov. 8, 2022, which is a 371 national phase of PCT/US2020/070757, filed Nov. 6, 2020, published as WO 2021/092628 A1 on May 14, 2021, and claims the benefit under 35 U.S.C. § 119 (c) of U.S. Provisional Patent Application No. 62/966,925, filed Jan. 28, 2020, and U.S. Provisional Patent Application No. 62/931,226, filed Nov. 6, 2019, the entire disclosures of which are incorporated herein by reference.

The subject matter of the present application is related to U.S. Provisional Patent Application No. 62/909,092, filed Oct. 1, 2019, the entire disclosure of which is incorporated herein by reference.

BACKGROUND

Tissue ablation and incisions can be used to in many ways to perform procedures such as surgical procedures. For example, lasers can be used to correct refractive error such as myopia, to remove cataracts, and to treat glaucoma and retinal disease. Tissue ablation and incisions can also be used orthopedics and cardiology to perform surgical procedures, for example.

Work in relation to the present disclosure suggests that the efficacy and availability of surgical procedures may be related to limitations of the devices used to incise and ablate tissue in at least some instances. For example, lasers such as femtosecond lasers can be complex, and the treatments may take longer than would be ideal. Also, the tissue removal profile along a laser induced incision may not be as smooth as would be ideal in at least some instances. Also, with laser treatments tissue artifacts and debris such as a plume associated with the laser irradiation can affect the accuracy and effectiveness of ablations and incisions.

Although mechanical cutting with blades such as microkeratome blades can be used for some surgical procedures, work in relation to the present disclosure suggests that mechanical cutting with blades can be less accurate and may produce rougher surfaces than would be ideal in at least some instances. Although mechanical keratomes have been used to create corneal flaps for surgical procedures such as LASIK, work in relation to the present disclosure suggests that mechanical keratomes can take somewhat longer than would be ideal, and the resulting flaps may be some irregular and rougher than would be ideal in at least some instances. Although a scalpel or diamond knife may be used to manually resect two separate flaps within tissue, such as scleral and/or corneal tissue in traditional canaloplasty, this can be technique dependent and somewhat difficult for at least some practitioners, which may be related postoperative complications. It would be helpful to reduce technique dependency and postoperative complications.

Although, femtosecond lasers have been used to create corneal flaps and pockets, work in relation to the present disclosure suggests that the time to form the flaps and pockets may take longer than would be ideal in at least some instances. The Small Incision Lenticule Extraction (SMILE) procedure is a more recent approach to reshaping the cornea that utilizes a femtosecond laser system to ablate tissue along the boundaries of a 3-dimensional lenticule within the corneal stroma, which may be removed through a corneal opening. However, work in relation to the present disclosure suggests that the 3-dimensional lenticule formed and removed with this procedure may be less than ideally shaped in at least some instances. Also, the amount of time to ablate tissue that defines the lenticule and opening can be somewhat longer than would be ideal.

Although electrodes have been proposed to treat tissue, the prior approaches can result in more tissue damage and less precise incisions than would be ideal. Although electrodes that generate plasma have been suggested, these prior approaches may not be well suited for cutting large volumes of tissue and the accuracy can be less than ideal in at least some instances.

In light of the above, there is a need for improved approaches to treating tissue with incisions that ameliorate at least some of the aforementioned limitations. Ideally, such approaches would decrease complexity and treatment times and provide more accurate incisions with improved outcomes.

SUMMARY

Embodiments of the present disclosure provide improved methods and systems for incising tissue. In some embodiments, an elongate electrode is configured to flex and generate plasma to incise tissue. An electrical energy source can be operatively coupled to the electrode and configured to provide electrical energy to the electrode to generate the plasma. In some embodiments, a tensioning element is operatively coupled to the elongate electrode. The tensioning element can be configured to provide tension to the elongate electrode to allow the elongate electrode to flex in response to the elongate electrode engaging the tissue and generating the plasma. In some embodiments, the tensioning element operatively coupled to the flexible elongate electrode allows the use of a small diameter electrode, such as a 5 µm to 20 µm diameter electrode, which can allow narrow incisions to be formed with decreased tissue damage. In some embodiments, the tensioning of the electrode allows the electrode to more accurately incise tissue by decreasing variations in the position of the electrode along the incision path.

In some embodiments, the elongate electrode is operatively coupled to one or more components to allow tissue resection along a path. The elongate electrode can be coupled to a support structure that moves with the electrode to provide an incision along a path. The support structure can be configured to support one or more arms, such as a plurality of arms, which arms support the electrode suspended between the arms. The support structure, one or more arms, and the elongate electrode may comprise components of an electrode assembly. The electrode assembly can be operatively coupled to a translation element to provide translational movement to the electrode in order to incise tissue. In some embodiments, a contact plate is configured to engage tissue to shape the tissue prior to incision with the elongate electrode, which can provide improved accuracy of the incision and the shape of tissue to be removed.

In some embodiments, a gap extends between the support structure and the electrode suspended between the arms, which can provide bidirectional tissue incisions and decrease treatment times. In some embodiments, the gap is sized to receive tissue and to incise tissue that extends into the gap when the support structure and electrode are drawn proximally. In some embodiments, the support structure and electrode are advanced to into the tissue to incise the tissue with a first incision on a first pass with a first configuration of one or more contact plates, and the support structure and electrode drawn proximally to incise tissue with a second configuration of the one or more contact plates. In some embodiments, the second configuration is different from the first configuration, and tissue incised with the first pass extends into the gap and is incised with the second pass so as to provide a resected volume of tissue for subsequent removal. In some embodiments, the resected volume of tissue comprises a thickness profile corresponding to a difference between a first profile of the first configuration and a second profile of the second configuration of the one or more contact plates. In some embodiments, a lenticule corresponding to a refractive correction of an eye is incised with the first pass and the second pass, and the lenticule can be subsequently removed to provide the refractive correction.

In some embodiments, an elongate electrode is configured to incise tissue such as corneal tissue. An electrical energy source is operatively coupled to the elongate electrode and configured to provide electrical energy to the electrode. A contact plate is configured to engage a portion of the tissue such as the cornea to shape the tissue prior to incising the cornea with the electrode. A support structure can be operatively coupled to the elongate electrode and the plate, the support configured to move the electrode relative to the plate and incise the corneal tissue with the electrode.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments and the accompanying drawings listed below.

DETAILED DESCRIPTION

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed systems and methods are well suited for incorporation into prior devices and surgical procedures, such as microkeratomes, incising tissue to form one or more of flaps, pockets, or lenticles for removal from tissue, e.g. SMILE. The presently disclosed methods and systems are well suited for combination with lens removal and prosthesis, such as removal of the lens nucleus and cortex for placement of an intraocular lens. By way of non-limiting example, a plasma-induced incision may be created in the capsule to produce a capsulorrhexis. Incisions may be created in the to produce lens fragments or to simplify lens fragmentation and/or lens removal. The incisions may be formed in the retina to produce a pocket or flap. In some embodiments an incision is formed in the TM to improve drainage and/or to lower intraocular pressure ("IOP") for the treatment of glaucoma, or in the iris to produce an iridotomy for example.

Although reference is made to incisions in tissues of the eye, the presently disclosed systems and methods are well suited for forming incisions in non-ophthalmic surgeries such as orthopedic surgery, cardiovascular surgery, neurosurgery, robotic surgery, pulmonary surgery, urologic surgery, and soft tissue surgery. Although reference is made to cutting ocular tissue, the presently disclosed methods and systems are well suited to forming incisions in one or more of collagenous tissue, cartilage, stromal tissue, neural tissue, vascular tissue, muscle and soft tissue.

Figure 1A:
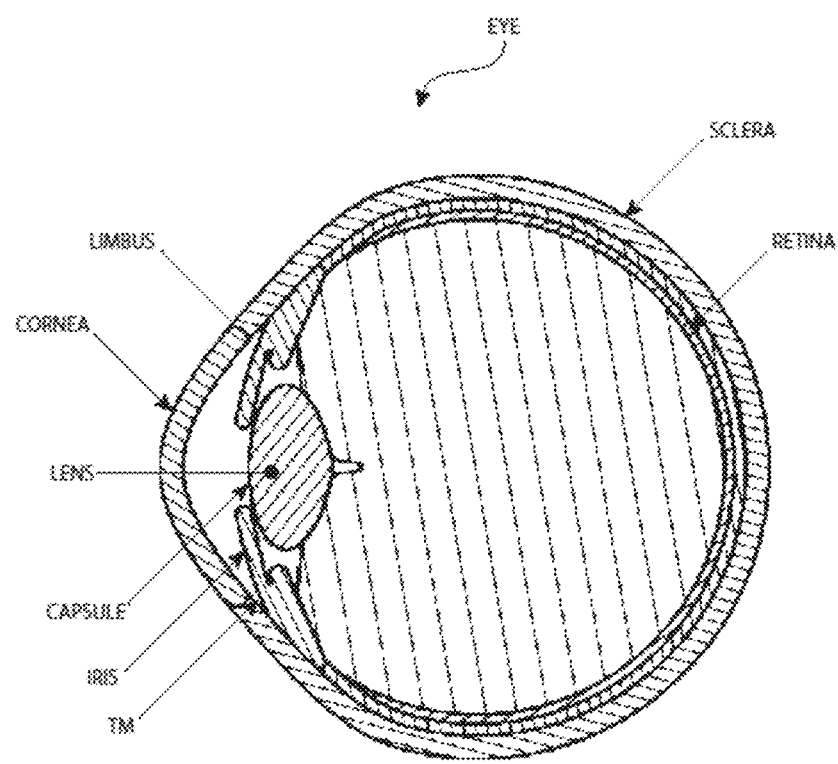
FIG. 1A is directed at a schematic image of an eye shown in cross section to show anatomical locations therein, in accordance with embodiments of the present disclosure.

By way of non-limiting example, FIG. 1A illustrates various anatomical locations in eye that may be suitable for practicing the present disclosure. The eye includes a cornea, a sclero-corneal limbus, a sclera, a lens capsule, a lens, a retina, an iris, and a trabecular meshwork TM. Although not shown for purposes of clarity, a Schlemm's canal may be located adjacent to TM. The presently disclosed systems can be used to treat any of these locations. In some embodiments, the cornea is shaped to provide refractive treatment of the eye. In some embodiments, the sclera is incised, for example to provide a filtering bleb to treat glaucoma. In some embodiments, at least a portion of the capsule is incised, for example so as to access the cortex and nucleus of the lens. In some embodiments, at least a portion of the lens is incised and resected. In some embodiments the retina is treated, for example with the electrode. In some embodiments, the IRIS is incised with the electrode. In some embodiments, tissues associated with TM and Schlemm's canal are incised, for example with reference to glaucoma surgery.

In some embodiments, the application of a sufficient voltage, including a periodic or pulsatile voltage, to an electrode in or around a biological tissue (i.e., a "target tissue structure") may result in the formation of a vapor in proximity to said electrode that derives from the initial current and/or the electric field established by heating at least a component of said tissue (e.g., water within a tissue) to about a vaporization temperature (or a "critical temperature", e.g. ~100° C. for pure water at standard pressure). The contents of such a vapor cavity may then be ionized by said electrode voltage to disrupt (or equivalently, "ablate") at least a portion of said target tissue structure, especially if the pulse duration of a pulsatile voltage waveform is sufficiently short when compared to the thermal relaxation time of the target tissue structure and thermal confinement is achieved and the amount remaining damaged tissue created thereby may be minimized. The creation of said vapor may be due to a phase change process and thus a concomitant temperature increase may cease once the vaporization temperature is reached via a latent heat process. The volume of said vapor cavity (or equivalently, "bubble") may increase as the amount of vapor is increased and may further scale directly with the electrode voltage and/or the current supplied by said electrode to the tissue as larger volumes of tissue are heated. Likewise, and/or pressure within said bubble may increase as the amount of vapor is increased and may further scale directly with the electrode voltage and/or the current supplied by said electrode to the tissue as larger volumes of tissue are heated. Subsequently, a plasma may be formed at least partially within said vapor cavity by ionizing the vapor should said electrode be operated with a voltage great enough such that the resultant electric field strength within the vapor cavity exceeds a discharge threshold to create a plasma-induced ablation, a combination of which when created along an electrode may create a plasm-induced incision. By way of non-limiting example, said discharge threshold may be selected from the group consisting of: an ionization threshold, an electrical breakdown threshold, a dielectric breakdown threshold, a glow discharge threshold, an ablation threshold, a disruption threshold, and combinations thereof. If the electrode voltage is great enough, the resultant electric field strength may allow for secondary discharge and produce an arc. Avoiding such arc discharge may be advantageous, as will be described elsewhere herein. Said plasma may allow electrical current to again flow through the electrode, the vapor, and the tissue, and my thus cause a further temperature increase. The bulk electrode temperature may be directly proportional to the amount of current flowing said electrode and/or to surface bombardment of ions and charged particles, chemical reactions, and radiation; which themselves may be functions of the amount of plasma generated. Energy may be efficiently delivered to a target tissue structure to achieve thermal confinement within at least a portion of a target tissue structure that is nearby the electrode and/or the vapor cavity to create and/or sustain said vapor cavity. Thermal confinement may be achieved if said energy is deposited in a target at an energy deposition rate that is greater than an energy dissipation rate; such as may be when a current only flows through a tissue nominally within a time that is less than or equal to about a thermal time constant of said tissue, such as may be achieved using a periodic or pulsatile voltage. Said thermal time constant may be a thermal relaxation time, as defined by the size or shape or geometry of the electrode, the size or shape or geometry of the vapor cavity, and combinations thereof. A time constant may alternately be defined as a mechanical response time, such as a displacement relaxation due to a transient deformation of tissue adjacent to a collapsing vapor cavity. For a semi-infinite slab of material, said thermal relaxation time $\tau$ may be approximated by $$\tau \approx \frac{d^2}{4\alpha},$$

where d is the distance into the tissue, and $\alpha$ is the thermal diffusivity of the tissue. For sclera and cornea $\alpha$ is ~0.14 mm2·s$^{-1}$. For example, such a thermal relaxation time for a d=~2 μm damage extent is $\tau$=~28 μs. Damage is defined herein as at least partially denatured tissue or at least partially denatured tissue components caused by the mechanism for creating the incision, such as plasma, heating, etc. Such mechanical response times may be dictated by the material's compressibility and density, which in turn may be related to the tissue hydration. For most species including humans, water may contribute ~76% of the weight of the corneal stroma.

In some embodiments, for example related to soft tissues, the following relations may be used to approximate the mechanical properties of said tissue;

$$M = K + \frac{4}{3}G,$$

where K and G are the bulk and shear moduli, respectively, and $$G \ll K, M \approx K = \frac{1}{\beta},$$

where $\beta$ is the tissue compressibility and the mean elastic modulus of corneal tissue may range between ~1 and ~3 MPa. Thus, a sufficiently intense and rapid increase in the temperature of a material (i.e. a tissue, or the constituents or components of a tissue) may cause an amount of said material to be vaporized. Said vaporization may be an explosive vaporization that disrupts the tissue; i.e. causes tissue "disruption," also known as tissue "breakdown," and tissue "rupture," and tissue "ablation." The extent of a vapor cavity may intrinsically mediate the plasma discharge process when operated as described in an at least partially compressive material, such as tissue, due to transient mechanical deformation and displacement of said material as an electric field strength may decrease as the square of the distance from an electrode (e.g. $\propto r^{-2}$) and a discharge may cease when the bubble grows to the extent that the distance from the electrode surface to the bubble surface is too large to continue to support said discharge throughout a vapor cavity with the operating voltage because the electric field strength may be commensurately diminished. Maintaining a glow-type of discharge or disallowing an arc-type of discharge may be beneficial to producing precise incisions with minimal collateral damage. Flashes of light may accompany the plasma. The rate of said flashes of light may be dependent upon a velocity. The intensity of said flashes of light may be dependent upon an energy per pulse, or the power to the electrode.

Figure 1B:
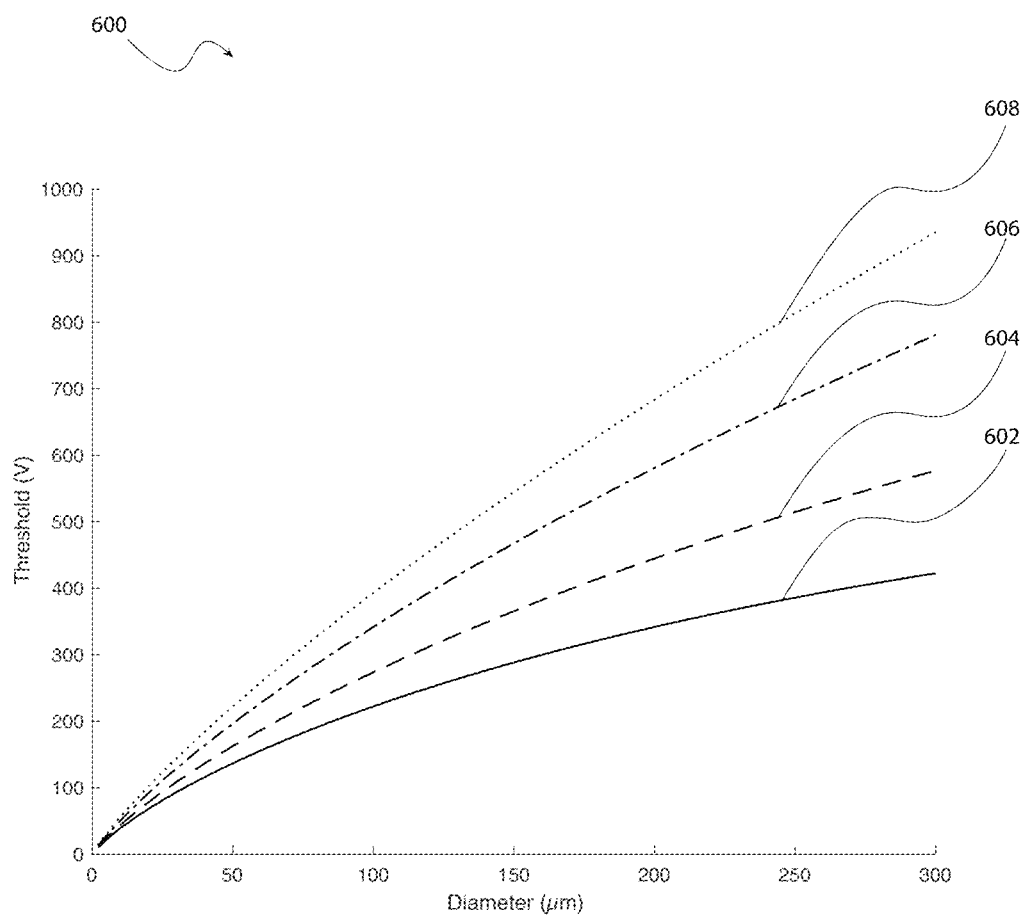
FIG. 1B is directed at a plot displaying a relationship between the measured threshold discharge voltage and pulse duration for negative and positive voltages for a single long, thin electrode, in accordance with embodiments of the present disclosure.

In some embodiments, the required voltage and associated energy deposition may be reduced by decreasing the width of the electrode, as shown in FIG. 1B, which contains plot 600; a relationship between the negative voltage threshold for tissue vaporization versus the diameter of a long cylindrical electrode for ~50 µs pulses using electrode lengths of ~1 mm, ~2 mm, ~5 mm, and ~10 mm corresponding to curves 602, 604, 606, and 608, respectively. Such electrodes may be deemed "elongate electrodes" due to the aspect ratio between a width and a length of said electrode. That is, an elongate electrode comprises a cross-sectional distance that is significantly smaller than its incisional length. This voltage may be made to be as low as possible and cutting with this voltage may be possible when the voltage exceeds the breakdown threshold without allowing for significant thermionic emission, where significant refers to an amount that noticeably contributes to tissue thermal damage beyond what would otherwise be present. An electric field around an electrode may scale with distance r is as follows, $$E = \frac{E_e r_e}{r},$$

where $E_e$ is the electric field at the surface of the electrode and $r_e$ is the radius of the electrode. Thus, the difference in electrical potential on the surface of the electrode to that at distance R from a nominally cylindrical elongate electrode may be $$\Delta U(R) = \int_R^{r_e} E(r) dr = E_e r_e \ln\left(\frac{R}{r_e}\right).$$

Thus, it may be that the electric field becomes nominally spherical at distances larger than the length of the electrode, L, and we may assume that at distances comparable to L the potential drops to zero; yielding $$E_e = \frac{U_e}{\ln\left(\frac{L}{r_e}\right)}.$$

The power density of the Joule heat generated by a current density j in a conductive material with resistivity $\gamma$ may be $$w = j^2 \gamma = \frac{U_e^2}{r_e^2 \gamma \ln\left(\frac{L}{r_e}\right)^2}.$$

The minimal energy density A required for vaporizing the surface layer of water within a tissue may be $A = w\tau = \rho C \Delta T$, where $\Delta T$ is the temperature rise of a liquid layer during a pulse of duration $\tau$, $\rho = \sim 1$ g/cm$^3$ is density of water, and $C = \sim 4.2$ J·g$^{-1}$·K$^{-1}$ is its heat capacity. Thus, the voltage U required for vaporization may be $$U = r_e \sqrt{\frac{\rho C \Delta T \gamma}{\tau}} \ln\left(\frac{L}{r_e}\right).$$

This voltage and associated energy deposition may be reduced by decreasing the thickness of the electrode, i.e. the radius of the aforementioned wire. Pulse durations $\tau$ may be kept shorter than a thermal relaxation time $\tau_r$ of a target tissue structure for a given electrode geometry. For example, the 1/e relaxation time for a long cylinder may be $$\tau_r \approx \frac{d^2}{9.32 \, \alpha},$$

where $$\alpha \equiv \frac{k}{\rho C}$$

is the thermal diffusivity of the material, and k being the thermal conductivity, which may yield a $\tau_r$ of ~65 µs for a ~20 µm diameter pure tungsten wire electrode, or ~1/5$^{th}$ that of an equivalent cylinder of water or tissue, as $\alpha_{tungsten} = \sim 0.66$ mm$^2$·s$^{-1}$ and $\alpha_{tissue} = \sim 0.14$ mm$^2$·s$^{-1}$. It may be noted from these curves that for a wire electrode of length of ~10 mm and diameter of less than ~30 µm utilizing a negative voltage of ~–200V may be appropriate for incising a target tissue structure while maintaining a margin of ~200V between the positive going breakdown threshold, as will be described elsewhere herein.

In some embodiments, discharge may start from vaporization of tissue around electrode and may continue when voltage is high enough to bridge the ionized gas-filled vapor gap between the electrode and the tissue. If the voltage is not enough to maintain such a vapor cavity along the entire length of electrode, liquid may contact the electrode, and allow an electrical current through that interface. The depth of heating may be proportional to the length of the liquid-electrode interface. Thus, the extent of the damage zone may increase with decreasing voltage for an otherwise fixed system. Greater voltage may correct for this, but if the voltage exceeds both negative and positive plasma thresholds, the electrode may become too hot and the plasma discharge may be self-sustained, as will be described elsewhere with respect to FIG. 3. Thermionic emission may be avoided to limit collateral damage to tissue. Turbulence may break the vapor cavity and both electrode and tissue may be damaged. An electrode may be so thin that a small voltage can support the vapor cavity and said voltage may be slightly above plasma threshold. A small thickness of vapor cavity may be maintained around at least a portion of the electrode at voltages lower than any plasma threshold. Translating the electrode may allow for contact of a small region of tissue and may be conceptualized as a single point of contact, or point-like contact. Such point-like contact may cause sudden vaporization, ignite a plasma discharge in the commensurately confined volume and disrupt tissue thereby. After a section of tissue is disrupted in this manner, a different section of the tissue may be already touching the advancing electrode elsewhere, leading to a next vaporization, discharge, and subsequent disruption in this region.

The amalgamation of such disruptions may be considered an incision. The heat distribution around a point-like discharge may be nominally spherical. The extent of heat deposition may be short and may scale as $r^{-4}$ where r is radius of discharge and the tissue damage zone may now depend more on the radius of electric discharge and less on length of electrode. If the radius of the point-like discharges is in the ~10 μm range, a sequence of such discharges may cut the tissue in a "punctuated" or "staccato" fashion by repeatedly breaking down different regions (i.e., at discontiguous locations or, equivalently, non-overlapping regions) of tissue along the electrode length and may leave a damage zone of only about a few μm in thickness. A constant arc may be avoided, and plasma made to remain in the glow regime by repeatedly breaking down regions of tissue and thereby modulating the electrode voltage to minimize damage from thermionic and resultant thermal effects. The different regions of tissue within a target tissue structure that may be repeatedly broken down may be adjacent to each other but need not.

Figure 2A:
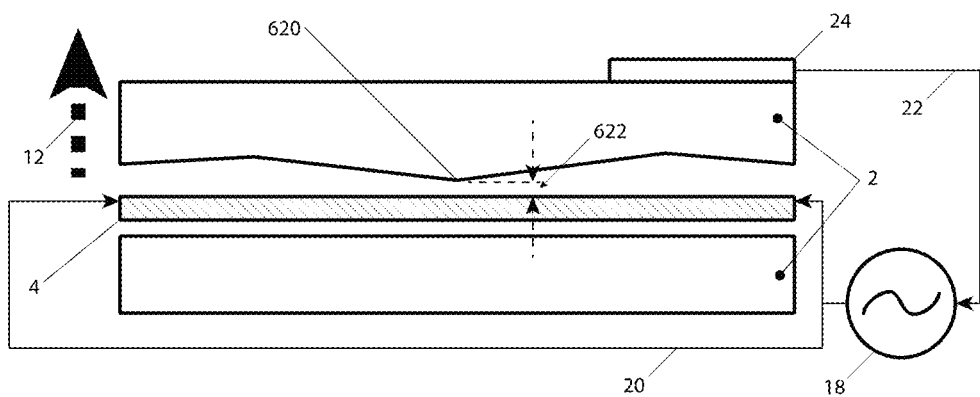
FIGS. 2A through 2F depict examples of different conditions encountered with varying electrode-to-tissue spacing and/or the electrode voltage, in accordance with embodiments of the present disclosure.

FIG. 2A illustrates electrode assembly 4 approaching tissue 2 along direction 12, where gap 622 exists between electrode assembly 4 and the closest region of tissue to the elongate electrode, tissue region 620. In this exemplary embodiment, both ends of electrode assembly 4 are connected in parallel to driver 18 via connections 20 and the return path to driver 18 is via connection 22 from return electrode 24. Driver 18 may be considered to be an electrical energy source that provides electrical energy to the electrode in order to produce plasma within a target tissue structure.

Figure 2B:
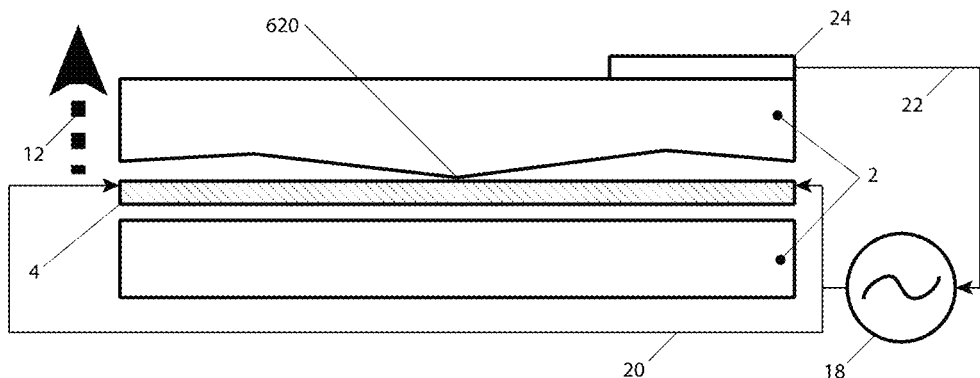

FIG. 2B illustrates the initial instantaneous connection of tissue 2 to electrode assembly 4 at contact region 620, wherein gap 622 has decreased to ~0.

Figure 2C:
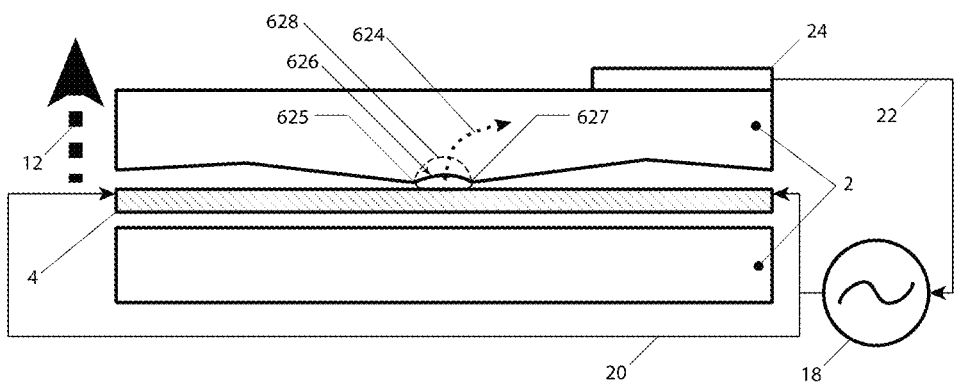

FIG. 2C illustrates a condition wherein the magnitude of the voltage on electrode assembly 4 is above at least a negative voltage plasma threshold value in region 620 (not shown) which may cause vaporization of at least a component of tissue 2 within tissue region 626 to create a vapor cavity 635 and may allow current 624 to flow to return electrode 24 and may create damage zone 628. Such damage zone 628 in turn may be limited in extent to a volume of tissue directly adjacent to tissue region 620 and either of such tissue regions 625 & 627 may be the next portion of tissue 2 to be instigate vaporization in the same manner as region 620 did previously to create a staccato processes, as described elsewhere herein. Discharge may start from the vaporization of tissue around electrode and may continue while voltage is high enough to bridge the vapor gap between the electrode and the tissue and ionize the vapor in the gap. If a portion of such an electrode has no contact with the tissue, for example, as may be the case when a vapor bubble has been formed about that region of the electrode, the electrode temperature may rise and increase in resistivity. For example, as may happen when a portion of a wire consumes more current than another portion of the wire when connected in series to a power source that is in "power-limiting-mode", as the average power may stay constant, but localized overheating in regions of increased resistivity may cause the portion of the wire to evaporate and break. However, this may be reduced, e.g. avoided, if an electrode is placed at a common voltage, such as may occur if both ends of a wire are connected to the same location in a circuit (or "node"). In this exemplary configuration, when one portion of the electrode may become more resistive due to overheating and the current may go through another portion of the electrode, wherein the current through the heated region may decrease and preserve the wire from failing as described earlier with respect to the serial connection configuration. The velocity of a moving electrode may be chosen to satisfy the condition of constant tension below the rupture tension of the wire. Too little tension may reduce said velocity. If an electrode is not in contact with tissue, there may be no heat transfer from the electrode to the tissue and the electrode temperature may increase. An arc current may then increase due to the electrode temperature increase and may instigate a positive feedback loop, which may in turn cause an overheating of tissue and/or the electrode when the electrode is under slack and/or low tension conditions that reduce the likelihood of a small region tissue contacting the electrode to produce the aforementioned staccato discharge. Since the plasma threshold is polarity dependent, the discharge may work as a rectifier and a rectified current may be used as feedback for cutting at about a minimum negative voltage threshold for plasma discharge, including by way of non-limiting example operation in the glow discharge regime. In this configuration the damage zone may now depend on the radius of the electric discharge instead of the electrode length. A punctuated sequence of discharges whose extents are in the ~10 μm range may result in a damage zone thickness of between ~1 μm and ~3 μm. The duty cycle of the power supply (e.g. driver 18, or "electrical energy source") in this configuration may be kept at ~100% due to the punctuated discharge process.

Figure 2D:
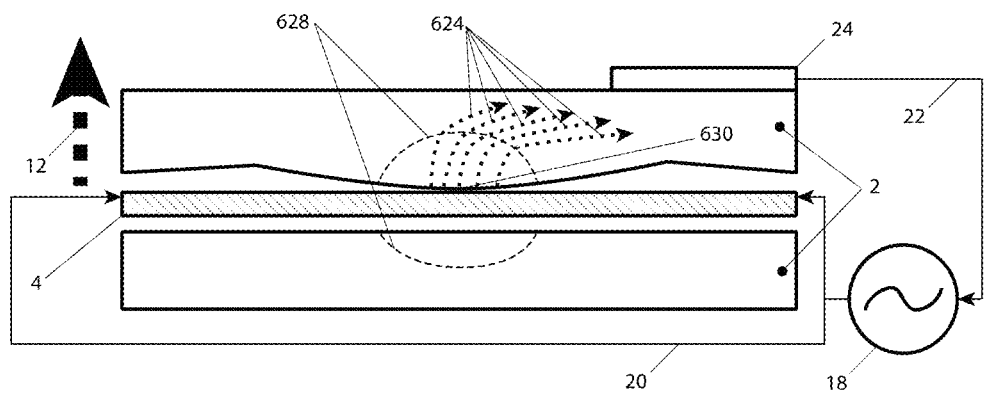

FIG. 2D illustrates a condition wherein the voltage on electrode assembly 4 is below a plasma threshold value and may fail to maintain a maintain a vapor cavity 635 such as region 626 of the previous figure and may cause contact region 620 to expanded along electrode assembly 4 to produce extended contact region 630, which is larger than contact region 620, and may allow for more current 624 to flow from electrode assembly 4 through tissue 2 to return electrode 24, producing a larger damage zone 628 than that of FIG. 2C, which may extend to portion of tissue 2 behind direction 12 via thermal conduction. If the electrode voltage cannot maintain a vapor cavity 635 along the electrode, tissue and/or liquid may contact the electrode and allow a large current through the interface. The extent of the damage may be proportional to the length of the electrode-tissue interface; i.e. extended region 630. Thus, a damage zone extent may increase with a decrease of voltage. Similarly, large damage zone may occur if no voltage is supplied to the electrode prior to its contacting tissue, as a relatively large portion of said electrode may simultaneously contact tissue before a discharge process initiates. To avoid such damage, a suprathreshold voltage may be applied to the electrode before it contacts tissue and an incision be produced as described with respect to FIG. 2C. Another way to protect tissue from overheating may be by using nonconductive liquids like Electro Lube Surgical, or viscoelastic substances (e.g. Healon). Such nonconductive liquids may serve as both a cooling agent and protection against current-related tissue damage such as electroporation. For example, a nonconductive liquid may be injected into the cutting region to protect tissue nearby the target tissue which may be in the current return path. Nonconductive liquid may also be cooled before use.

Figure 2E:
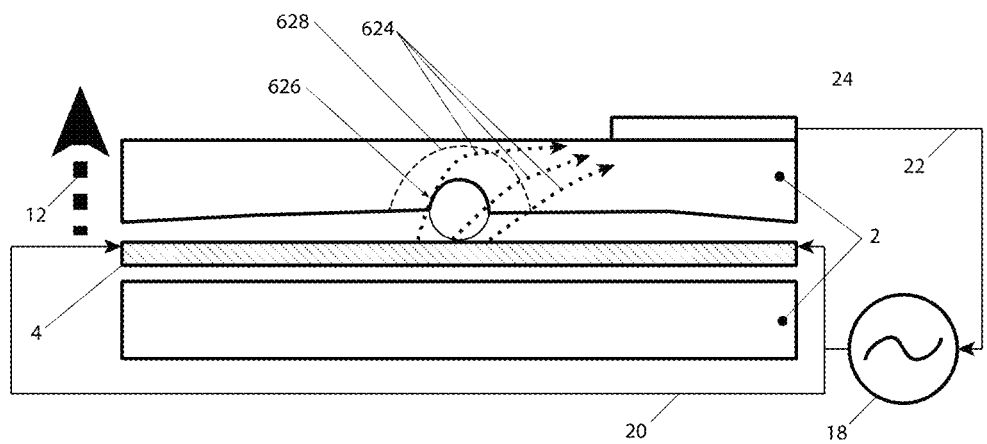

FIG. 2E illustrates a condition wherein the magnitude of the voltage on electrode assembly 4 may be greater than both a negative plasma threshold value and a positive plasma threshold value and contact region 620 has expanded along electrode assembly 4 to produce a vaporization region 626 that may be greater than that of the vaporization region 626 in FIG. 2C. Likewise, more current 624 may flow from electrode assembly 4 through tissue 2 to return electrode 24 in this configuration than that of FIG. 2C, producing a larger damage zone 628 than that of FIG. 2C. An electrode voltage exceeding both negative and positive plasma thresholds may cause the electrode to become hot enough to provide self-sustained thermionic emission. Turbulence may interrupt vapor cavity 635 and may damage the electrode and/or the tissue.

An elongate electrode may comprise a nominally circular cross sectional (or "round") wire and decreasing the electrode width may be equivalent to reducing the diameter (or, equivalently, its "cross-sectional distance") of said wire. This voltage may be kept as low as possible while still rupturing tissue to avoid overheating of a target tissue. The electric field from a nominally cylindrical electrode may tend toward zero at distances on the order of the electrode length, which may in turn cause unnecessarily extended damage zones in tissue when using such an electrode with an aspect ratio >>1 (e.g., when the electrode comprises a long, thin wire). A staccato process of tissue breakdown as described herein may provide for a reduced damage zone due to the intrinsic interruption of current flow through tissue that may accompany said approach, as in the absence of tissue disruption electrical current may nominally only substantially flow through tissue when the tissue is contact with the electrode.

Although usually circular in cross-section, wire can be made in square, hexagonal, flattened rectangular, or other cross-sections. Thus, an electrode may be alternately configured using a nominally non-circular cross-sectional conductor, such as that of a rectangular cross-section. Such nominally non-circular cross-sectional wire may be available from Eagle Alloys (Talbott, TN). Rectangular cross-sectional electrodes may be created by stamping a foil sheet, such as those that also may be available from Eagle Alloys (Talbott, TN). A non-circular cross-section electrode may be further configured such that its thinnest dimension is nominally parallel to the translation direction to provide for electrode deformability along the translation direction and increased stiffness in the orthogonal direction. A conducting wire or thread with a high melting point, forming part of an electric circuit may be referred to as a filament as will be appreciated by one of ordinary skill in the art.

Figure 2F:
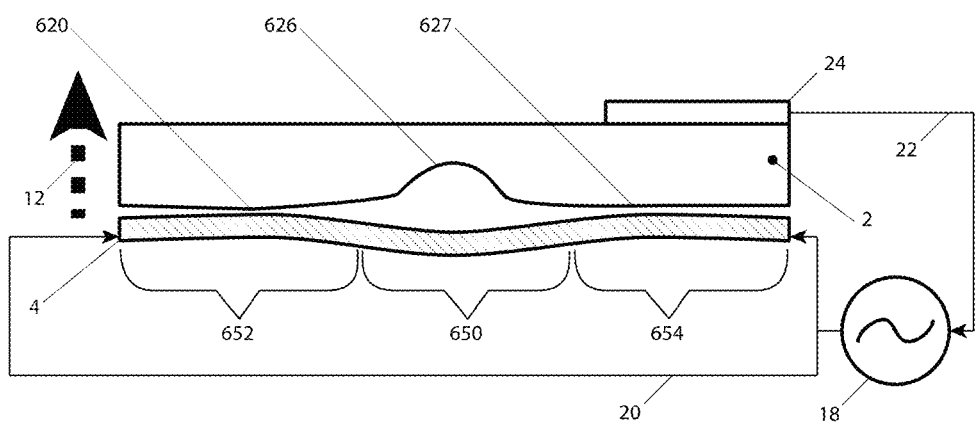

FIG. 2F illustrates a condition wherein electrode assembly 4 may be comprised of electrode regions 650, 652, and 654, which need not represent the entire incisional length. The electrode as shown has deformed during an incision and electrode regions 652 and 654 are displaced in the direction of motion 12 while electrode region 650 is not, which may occur when at least one of the electrode regions 650 through 654 is flexible. By way of non-limiting example, configuring electrode assembly 4 to be flexible, such as by using a thin wire, for at least a single region of an electrode regions 650 through 654 may provide said deformability. In the exemplary embodiment, a new closest region of tissue to the electrode, most proximal tissue region 620 is now approached by electrode region 652 and most proximal tissue region 620 is what was tissue region 625 of FIG. 2C and may be the next portion of tissue 2 to instigate vaporization in the same manner as region 620 did previously to create a piecewise incision. The shape of tissue 2 may be altered by the ablation of at least a single tissue region and thus cause a portion of tissue 2 to instigate vaporization in the same manner as region 620 did previously to create a piecewise incision.

Figure 3:
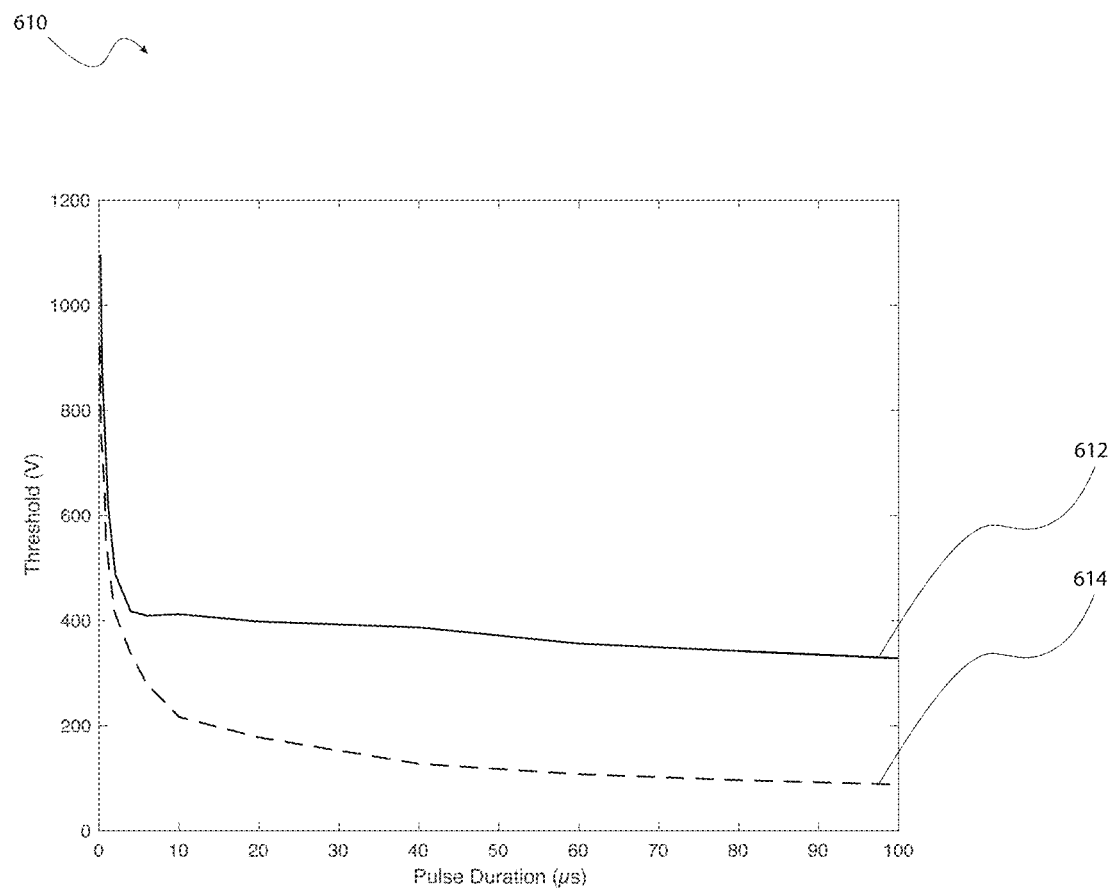
FIG. 3 is directed at a plot displaying a relationship between the measured negative threshold voltage and electrode diameter for a fixed pulse of varying duration, in accordance with embodiments of the present disclosure.

FIG. 3 shows plot 610; measured relationships between the polarity dependent voltage thresholds for vaporization versus pulse duration for a negative voltage discharge (curve 614) and a positive voltage discharge (curve 612) using a pulsatile voltage delivered with a ~8 mm long ~Ø50 µm tungsten wire electrode submerged in a bath of a physiologically balanced salt solution and observing such discharge using a camera. The lower threshold voltage for the negative discharge regime may lend itself to creating an incision with less damage than that of the positive discharge regime due to the concomitant lower currents. Thus, driver 18 may be configured to utilize a negative voltage bias.

A pulsatile voltage waveform may be used to create a plasma as described. In water, for example, a vapor cavity may expand at a mean velocity of ~0.5 m·s$^{-1}$, as averaged over a bubble lifetime of ~500 µs, away from a ~Ø20 µm thick electrode operating with a nominally sinusoidal waveform having a peak voltage of ~300V, causing discharge to cease due to a collapse of the vapor bubble (and possible subsequent cavitation), which may transfer momentum between the material and the electrode. In this configuration, the time required to reignite a plasma may be on the order of milliseconds, which may be long in comparison to the pulse period of the energizing waveform in the ~MHz regime and require considerably greater voltage to sustain discharge. However, if the distance between the tissue and the electrode surface is reduced, such as by moving the electrode, breakdown may be reinitiated sooner. The velocity of the resultant incision produced by the plasma may be referred to herein as the "tissue velocity." The frequency of a pulsatile electrode voltage may be configured in the ~MHz range and allow for a plurality of cycles during a tissue breakdown and/or a bubble lifetime. By way of non-limiting example, the nominal type of said waveform may be selected from the group consisting of: a sinusoidal waveform, a square-wave waveform, a triangle-wave waveform, a ramp waveform, a periodic waveform, a non-periodic waveform, and combinations thereof. The amount of time it takes for the electrode to move into tissue contact and the amount of time it takes for vaporization may be longer than the amount of time it takes to complete a discharge process. An electrode may be cooling when not disrupting tissue and the time an electrode is in contact with tissue and not disrupting tissue may cause tissue damage due to thermal diffusion from the electrode into the tissue, which may in turn require more energy to overcome a reduced electrode temperature. Thus, a lower incisional duty cycle may engender concomitantly greater thermal damage to tissue than a higher incisional duty cycle.

In some embodiments, the failure to achieve thermal confinement may result in collateral tissue damage. Such as may be the case for a rigid electrode, as the velocity at all locations along the electrode is constant, but the velocity of the tissue along the electrode may not be constant, i.e. there may be a distribution of tissue velocities in both time and space along the cutting edge of an electrode. A rigid electrode can only move as fast as the slowest cutting velocity it achieves. That is, a rigid electrode may need to incise a complete path along its cutting edge in order to advance and incise further, thus causing regions of tissue to compact onto the electrode prior to being incised and limit the instantaneous cutting velocity by allowing only an average cutting velocity. Hot spots along the cutting edge of a rigid electrode may provide for punctate vaporization, but those same locations may then linger in tissue awaiting similar breakdown at other locations, even with a rigid elongate electrode. The time spent lingering may be longer than a thermal or a mechanical response time of a tissue and result in collateral damage due to heat dissipation into tissue, especially in the presence of excessive liquid. A more efficient use of energy may be the desiccation of a next region of tissue to be incised. Actuating a rigid electrode at too fast a translation rate may not allow for a complete incision and cause "traction." Collateral damage may be thus reduced if the actuated velocity of an electrode nominally accommodates the discharge velocity within a vapor cavity 635.

In some embodiments, a deformable electrode may move within the material it is incising with a piecewise velocity profile. That is, unlike a traditional rigid electrode, a portion of a deformable electrode may advance into a cavity (or "bubble") created by a vaporization event to then vaporize a new region of tissue before other regions along the electrode have similarly advanced and thus allow for a velocity distribution of instantaneous cutting velocities along the electrode. Such a deformable electrode may be kept under tension along its length, which may in turn cause the deformable electrode to advance through tissue at a rate at least partially determined by an average cutting rate and at least partially determined by a local cutting rate, which may be itself at least partially determined by the tension force on the electrode. The mass (or a mass density) and/or the stiffness of a deformable electrode may at least partially dictate its ability to advance into a cavity created by a vaporization event. An average cutting rate may be affected by moving an electrode or electrode assembly using a translation element (or "translation device") and an actuator (e.g. along the x-axis, where +x may be defined as the direction of the intended incision). By way of non-limiting example, a translation element may be selected from the group consisting of: a translation stage, a linear stage, a rotary stage, a rail, a rod, a cylindrical sleeve, a screw, a roller screw, a travelling nut, a rack, pinion, a belt, a chain, a linear motion bearing, a rotary motion bearing, a cam, a flexure, a dovetail, and combinations thereof. As used herein, the terms "stage" and "slide" are considered equivalent when used to describe a translation element, device, or system. By way of non-limiting example, such actuators may be chosen from the group consisting of: a motor, a rotary motor, a squiggle motor, a linear motor, a solenoid, a rotary solenoid, a linear solenoid, a voice coil, a spring, a moving coil, a piezoelectric actuator, a pneumatic actuator, a hydraulic actuator, a fluidic actuator, and combinations thereof. Alternately, the electrode assembly may be manually actuated.

In some embodiments, a tension may be chosen to accommodate the stiffness of the material being used to form an electrode, such as may be represented by an elastic modulus. By way of non-limiting example, an elastic modulus may be chosen from the group consisting of: a flexural modulus, a Young's modulus, a bulk modulus, a section modulus, and a shear modulus. For a deformable electrode supported at least a single end by a support structure, a modulus E of the electrode material may be used to determine a tension force F for an allowed deflection distance $$d = \frac{FL^3}{48IE},$$

where L is the unsupported length of the electrode and I is the second moment of inertia for the cross-sectional shape of the electrode; and may be given by $$I = \frac{bh^3}{12}$$

for a rectangular electrode, where w is the thickness of the electrode in the direction orthogonal to the deflection, and h the thickness of the electrode in the direction of deflection, such as may be equal to $\sim 2r_e$ as described earlier herein. Similarly, second moment of a cylindrical electrode, such as a wire, may be given by $$I = \frac{\pi r^4}{2},$$

where r represents the radius of said cylinder.

In some embodiments, there may be a tradeoff between a characteristic extent (i.e. a "dimension" or a "thickness" or a "size") of an electrode (e.g. a diameter in the case of a wire or other such elongate electrode) and its corresponding mechanical stability, and therefore the strength and ruggedness of an instrument constructed thereby, especially in a system comprising a moving elongate electrode. Therefore, a thin wire electrode stretched taught may provide for increased mechanical stability over a slack thin wire electrode. Increased mechanical stability may manifest increased incisional precision (e.g., such an electrode may be less likely to drift transversely to the incision direction). An alternate embodiment may further comprise a tensioning element mechanically coupled to the electrode provide for a nominally more constant tension force on the electrode. A thin, deformable elongate electrode as described herein may be treated as the fundamental mode of a simple harmonic oscillator, with a fundamental frequency (or, equivalently, a mechanical resonance frequency)

$$f_0 = \frac{1}{2\pi}\sqrt{\frac{k}{m}},$$

with k being the material stiffness and m the mass. The collapse of a vapor cavity may cause said tensioned electrode to accelerate at least partially according to the tension provide and where the collapse of the cavity may be considered much like releasing a plucked string (i.e., the electrode). A force F on such a tensioned deformable elongate electrode adjacent to a cavity of extent z may then be understood as $$F = \frac{2Tz}{l},$$

where T is the tension on the electrode, l the unsupported length of the electrode, and extent z may be a diameter of a nominally spherical cavity, and z<<l. Similarly, $$f_0 = \frac{1}{\pi l}\sqrt{\frac{T}{2\mu}}$$

for a tensioned electrode with linear mass density µ, where $$\mu = \frac{\pi \rho \varphi^2}{4}$$

and ρ=~9*10³ kg·m⁻³ for pure tungsten. For example, considering a ~Ø10 µm nominally pure tungsten wire of unsupported length l=~10 mm (i.e., a mass of ~7 µg, or a linear mass density µ (or, equivalently, a mass per unit length) of ~0.7 µg·mm⁻¹) that is tensioned at T=~200 mN the preceding relations may yield k=~40N·m⁻¹, f=~12 kHz and a period of τ=~83 µs. Alternately, a ~Ø5 µm nominally pure tungsten wire of unsupported length l~10 mm, µ~0.177 µg·mm⁻¹, and T~100 mN may yield f=~17 kHz. Alternately, a ~Ø19 µm nominally pure tungsten wire of unsupported length l~8 mm, µ~2.55 µg·mm⁻¹, and T~300 mN may yield f=~9.65 kHz. Alternately, a ~Ø12.5 µm nominally pure tungsten wire of unsupported length l~3 mm, µ~1.1 µg·mm⁻¹, and T~300 mN may yield f=~39.1 kHz. Alternately, a ~Ø200 µm nominally pure tungsten wire of unsupported length l~12 mm, µ~282 µg·mm⁻¹, and T~1N may yield f=~1 kHz. The force required to deform an elongate electrode may scale nonlinearly with a characteristic cross-sectional distance of said electrode.

In this configuration such an electrode may be translated in the x-direction, and may be displaced ("plucked") by x=~20 µm to produce a local peak velocity x' of $$x' = \frac{20\,\mu m}{\frac{83\,\mu s}{4}} \to \sim 1\ m\cdot s^{-1},$$

which may be constrained to motion predominantly along the incision direction, x-axis (i.e. parallel to the direction of electrode translation, or equivalently, transverse to an elongate direction) and thereby minimizing errors that are transverse to the intended incision direction. Such a configuration may provide for reduced thermal damage and/or reduced traction as compared to that of systems comprising of rigid electrodes as primary heat deposition and/or thermal diffusion may be relatively reduced by utilizing such a deformable electrode to better match the tissue velocity. Such a deformable (or "flexible") electrode may move faster than its associated plasma incises tissue, as a local velocity of said electrode may be inversely proportional to the sag on said electrode and said electrode may tend to follow the plasma to relieve an increased tension thereon and may move with velocities greater than ~1 m·s⁻¹. In doing such, said electrode may be said to "flex" or "deform" or "vibrate." As such, an elongate electrode, as described herein, may vibrate (or, equivalently, "deform", or, equivalently, "flex") transversely to the elongate axis of the electrode. By way of non-limiting example, the following table lists various configurations of electrode materials, sizes, and their corresponding mechanical resonance frequencies.

In some embodiments, thermal confinement may be achieved if a discharge is produced within a single cycle of a pulsatile voltage waveform, such as within a nanosecond timeframe. From the field of laser-tissue interaction we know that explosive vaporization by nanosecond pulses may produce a peak temperature of ~200° C. and that the volume of the resultant void (or "crater" or "cavity") may be ~50% greater than the substantially heated volume. For example, photodisruption is known to produce such damage volumes. The ejection of vapor and/or water and/or debris from an incised region may preclude the formation of an arc discharge between the electrode and its environment, even at high temperatures; something which a thin deformable electrode may intrinsically provide, especially should said deformable electrode contact tissue along a region that is less than its circumference and produce a void that is larger than the interaction volume, as was described regarding certain effects of photodisruptive nanosecond laser pulses. This extended damage volume may assist in the ejection of debris and/or water and/or vapor. For example, the energy E required to raise a ~Ø10 µm sphere of water from ~20° C. to ~200° C. is E=ρc ΔT V→396 nJ. However, a bubble that is smaller than the extent of the electrode may nonetheless provide for a resultant cavity of sufficient extent to allow passage of the entire electrode, such as may be the case with tissue contact along only ~½ to ~⅔ of the electrode circumference (or equivalently, only ~½ to ~⅔ of the electrode diameter, as geometrically projected onto said tissue) due to the increase in the resultant crater volume. The commensurate reduction in energy required to induce a plasma in this case may be $$E^* \sim \frac{2}{3}E \to 114\ nJ$$

and the extent of the resultant crater may be sufficient to accommodate the entire ~Ø10 µm electrode, as may be especially the case for mechanically compliant tissues. By way of non-limiting example, a power of ~15 W may be delivered to an electrode at a pulse repetition frequency ("PRF") of ~1 MHz for an incision width of ~10 mm (or equivalently, an average linear average power density of ~1.5 W·mm$^{-1}$), providing ~15 µJ of energy per cycle (or per "pulse"), for $\tau_{pulse}$=~1 µs. For example, a ~10 mm long, ~Ø10 µm wire electrode operating as described with PRF=~1 MHz and $E_{pulse}$=~15 µJ, an active ablation length per pulse may observe the following relation, $$L_a = \phi \frac{E_{pulse}}{E*},$$

and $L_a$ may be ~1.32 mm. Furthermore, $L_a$ need not comprise a single contiguous length but may be comprised of separate instances of discrete ablations or discrete ablation regions distributed along an entire electrode length such that the individual lengths of said discontinuous zones (or, equivalently, non-overlapping regions) may sum to about the value of $L_a$ per pulse. Said electrode may also be translated through tissue at an active translation velocity (or "rate") $v_a$ that is at least partially determined by $L_a$, such as $$v_a \approx PRF \frac{\phi}{2} \frac{L_a}{L}.$$

Continuing with the previous exemplary configuration, a total active length of ~1.32 mm along a ~10 mm long, ~Ø10 µm electrode may be translated through tissue with an active translation velocity $v_a$ of ~660 mm·s$^{-1}$ to incise tissue while the electrode may deform as it incises and an actual local peak velocity of at least a single portion of said electrode may be different than $v_a$ due to the velocity of an underlying translation via an actuator, $v_t$, as well as the elasticity of and tension applied to the electrode, as described elsewhere herein. That is, $v_t$ need not be equal to $v_a$. $v_t$ may be chosen to be between ~1 mm·s$^{-1}$ and ~5000 mm·s$^{-1}$. Optionally, $v_t$ may be chosen to be between ~10 mm·s$^{-1}$ and ~1000 mm·s$^{-1}$. Optionally, $v_t$ may be chosen to be between ~50 mm·s$^{-1}$ and ~500 mm·s$^{-1}$. By way of non-limiting example, a ~10 mm long, ~Ø13 µm tungsten wire under ~300 mN of tension operating with PRF=~1 MHz and $E_{pulse}$=~15 µJ may be translated with a peak $v_t$ of ~300 mm·s$^{-1}$ to incise corneal tissue with minimal collateral damage. Considering the foregoing, a system may be configured to allow the electrode velocity to nominally match the tissue velocity using a moving front of plasma-induced bubbles along the length of a deformable electrode that is translated through a tissue to be incised. A variable velocity may be used, as is discussed elsewhere herein.

Figure 4:
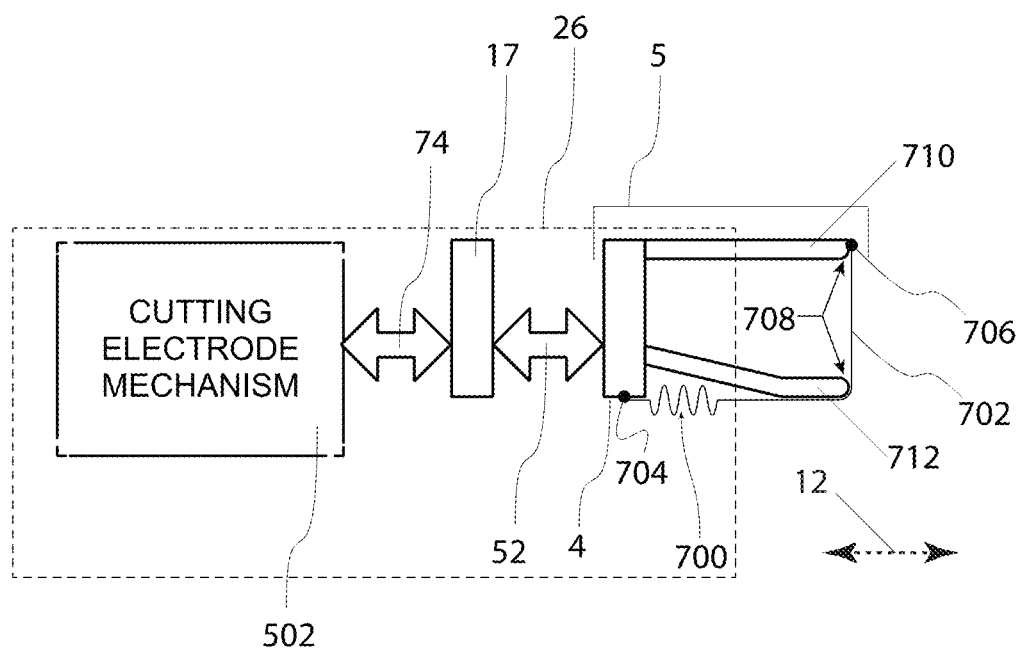
FIGS. 4 & 5 are directed at an electrode subsystem of a system to incise a target tissue structure, in accordance with embodiments of the present disclosure.

FIG. 4 shows a tensioned electrode assembly 5 may comprise tensioning element 700, which in turn may be operatively coupled to electrode 702 and affixed to electrode assembly 4 via attachments 704 & 706 such that tensioning element 700 allows electrode 702 to stretch (or "deform" or "flex" or "vibrate") while in contact with tissue 2 (not shown in the present figure). The incisional portion of electrode 702 may comprise only a portion of the conductive portion of electrode 702. Radii 708 located atop arms 710 & 712 may provide a smooth surface for electrode 702 while it stretches in order to avoid excessive strain as might be imparted at a sharper transition. Arms 710 & 712 may be considered to be at least a portion of a support structure intended to provide mechanical stability to at least a portion of electrode 702. A gap may exist between arms 710, 712, and may serve to receive tissue before and/or during and/or after creating an incision, such as is shown in the instant embodiment. In some embodiments, the electrode assembly 5 comprises a support structure as described herein.

In some embodiments, a processor, e.g. a controller, is operatively coupled to the elongate electrode to provide movement to the elongate electrode. For example the processor can be configured with instructions provide to control the actuator and move one or components of the electrode assembly. In some embodiments, the processor is configured with instructions to advance the electrode distally and draw the electrode proximally, for example.

In some embodiments, the elongate electrode is sized for insertion into the tissue, and the processor is configured with instructions to incise the tissue with the electrode to define a volume of incised tissue within a pocket. While the volume can be configured in many ways, in some embodiments the volume comprises a shape profile, e.g. the shape profile of a lenticule. In some embodiments, the processor is configured with instructions to move the electrode with a first movement to define a first incised surface on a first side of the volume of tissue and moved with a second movement to define a second incised surface on a second side of the volume of tissue. In some embodiments, the processor is configured with instructions to advance the electrode distally to define a first surface on a first side of the volume of tissue and to draw the electrode proximally to define a second surface on a second side of the volume of tissue. In some embodiments, a gap extends between the elongate electrode and the support structure and the gap is sized to receive tissue such that tissue extending into the gap is incised when the electrode is drawn proximally.

In some embodiments, the movement of the electrode is coordinated with the shape of one or more contact plates, in order to define the volume of incised tissue. In some embodiments, the contact plate comprises a first configuration to define a first surface on a first side of the volume of tissue and a second configuration to define a second surface on a second side of the volume of tissue. In some embodiments, a first contact plate comprises a first shape profile to define a first surface on a first side of the volume of tissue and a second shape profile to define a second surface on a second side of the volume of tissue, e.g. first and second surfaces of a lenticule comprising the volume of tissue. In some embodiments, the contact plate comprises a plurality of actuators operatively coupled to the processor, and the processor is configured with instructions to shape the contact plate with a first surface profile for a first incision, and to shape the contact plate with a second profile for a second incision. In some embodiments, processor is configured with instructions to shape the contact plate with the first profile, incise the first side with the first shape profile, shape the contact plate with the second profile, and incise the second side with the second profile, with a total time of no more than about 10 s, for example no more than 5 s, or no more than 2 s, for example.

A support structure may be fabricated, at least partially from a material that is selected from the group consisting of: tungsten, nitinol, steel, copper, brass, titanium, stainless steel, beryllium-copper alloy, cupronickel alloy, palladium, platinum, platinum-iridium, silver, aluminum, polyimide, PTFE, polyethylene, polypropylene, polycarbonate, poly (methyl methacrylate), acrylonitrile butadiene styrene, polyamide, polylactide, polyoxymethylene, polyether ether ketone, polyvinyl chloride, polylactic acid, glass, ceramic, and combinations thereof. Tensioning element 700 may be connected directly to at least a portion of electrode assembly 4 as shown, or alternately to a at least a portion of a subsequent element to which electrode assembly 4 is attached; such as coupler 52 or electrode assembly mount 17. By way of non-limiting example, tensioning element 700 may be a spring, a coil spring, a leaf spring, a torsion spring, an elastic mesh, a hinge, a living hinge, and combinations thereof. A deformable electrode may be supported by a support structure and allowed to deform while creating a plasma-induced incision within a target tissue or target tissue structure. An electrode (e.g. electrode 702, or portions thereof) may be at least partially composed of a material selected from the group consisting of: tungsten, nitinol, steel, copper, brass, titanium, stainless steel, beryllium-copper alloy, cupronickel alloy, palladium, platinum, platinum-iridium, silver, aluminum, and combinations thereof. Alternately, an electrode may comprise a wire composed of the same materials just listed. Alternately, an electrode may be coated in certain areas to preclude conduction and/or incision in said areas. Alternately, tubing may be used in lieu of a coating to insulate areas of an electrode. Such a coating or tubing may be selected from the group consisting of: polyimide, PTFE, polyethylene, polypropylene, polycarbonate, poly(methyl methacrylate), acrylonitrile butadiene styrene, polyamide, polylactide, polyoxymethylene, polyether ether ketone, polyvinyl chloride, polylactic acid, glass, ceramic, and combinations thereof. An electrode (e.g. electrode 702) may be a wire having a diameter between ~3 μm and ~300 μm. Alternately, said wire may have a diameter between ~10 μm and ~50 μm. Alternately, said wire may have a diameter between ~12 μm and ~17 μm. Tensioning element 700 may be configured to provide tension of such that the resultant force on an electrode is ~80% of a rated or measured yield strength of the electrode or its material; such as may be the case for a tungsten wire of ~Ø12.5 μm loaded with a tension of ~295 mN, which may also correspond to an elongation of ~0.5%. Optionally, a tensional force may be between ~50% and ~95% of a yield strength. Optionally, a tensional force may be between ~70% and ~85% of a yield strength. Other configurations may be scaled using the relationships relating to the second moment of inertia, as described earlier herein with respect to allowable deflection distances (e.g. ~80% of a rated yield tension force of ~4.7N, or ~3.8N, for a nominally pure tungsten wire with a diameter of ~Ø25 μm. Coupler 52 may be operatively coupled to cutting electrode mechanism 502 via coupler 74. By way of non-limiting example, coupler 74 may be a receptacle configured to accept a disposable module comprised of elements electrode 4, coupler 52, and electrode mount 17 and wherein electrode mount 17 comprises mating features compatible with those of coupler 74 such as threads, a clasp, a snap fitting, and combinations thereof. Cutting electrode mechanism 502 may further comprise mating features compatible with those of couplers 71 & 72, which are themselves mechanically coupled to actuators 50 & 504, respectively, and may provide axes of motion to move electrode assembly 4 to create an incision in tissue 2 (not shown). Alternately, by way of non-limiting example, elements electrode 4, coupler 52, electrode mount 17, cutting electrode mechanism 502, and coupler 74 may be packaged into a probe body 26 as a disposable module configured to engage with a more complete incisional system to actuate said electrode or electrode assembly or probe assembly along axis of motion 12. Although not shown for clarity, at least portions of probe body 5, including tensioned electrode assembly 5, maybe made to move using a translation element to ensure mechanical stability and accuracy along at least a single direction of motion.

Figure 5:
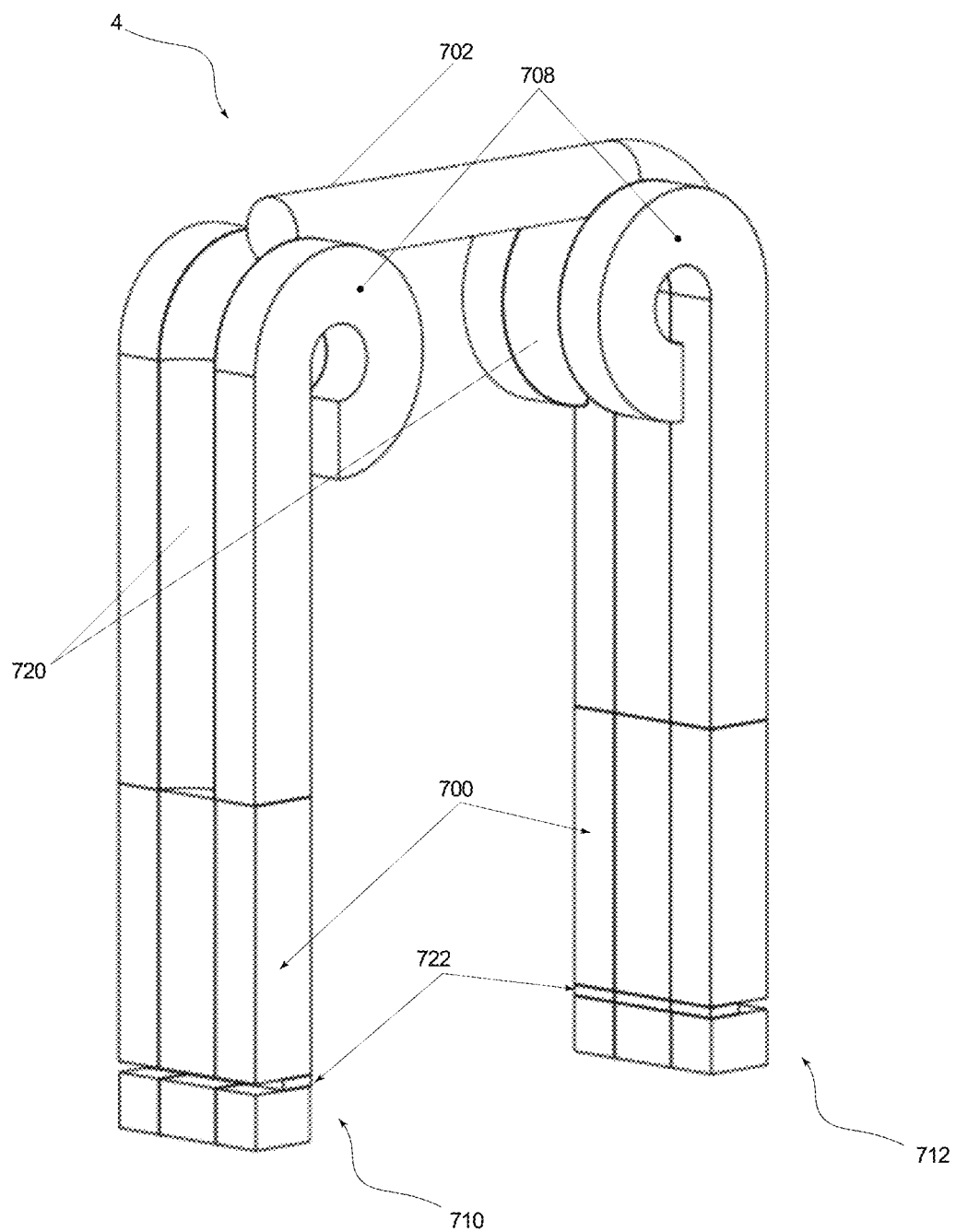

FIG. 5 shows a tensioned electrode assembly 5 similar to that of FIG. 4, wherein radii 708 may further comprise channels 720 into which electrode 702 may be placed to minimize positional errors due to unintentional electrode movement, especially that which is transverse to the intended incision direction. Tensioning element 700 may be configured as a living hinge (or hinges, as shown) within or along arms 710 & 712. Arms 710 & 712 may be comprised of a notched rigid material, as shown to provide living hinge 722. By way of non-limiting example, a suitable material for creating a living hinge may be selected from the group consisting of: polyethylene, polypropylene, polycarbonate, poly(methyl methacrylate), acrylonitrile butadiene styrene, polyamide, polylactide, polyoxymethylene, polyether ether ketone, polyvinyl chloride, copper beryllium, and combinations thereof. In the case where living hinge 722 is integral to an arm 710 or 712 and an electrically conductive material may be chosen and such cutting electrode may be soldered, brazed, adhered with an electrically conductive adhesive, and/or welded to the arm(s). In the case where a living hinge is integral to an arm 710 or 712 and an electrically insulating material is chosen, electrode 702 may be otherwise adhered to the arm, or be soldered, brazed, and/or welded to an adjacent conductive material.

Figure 6:
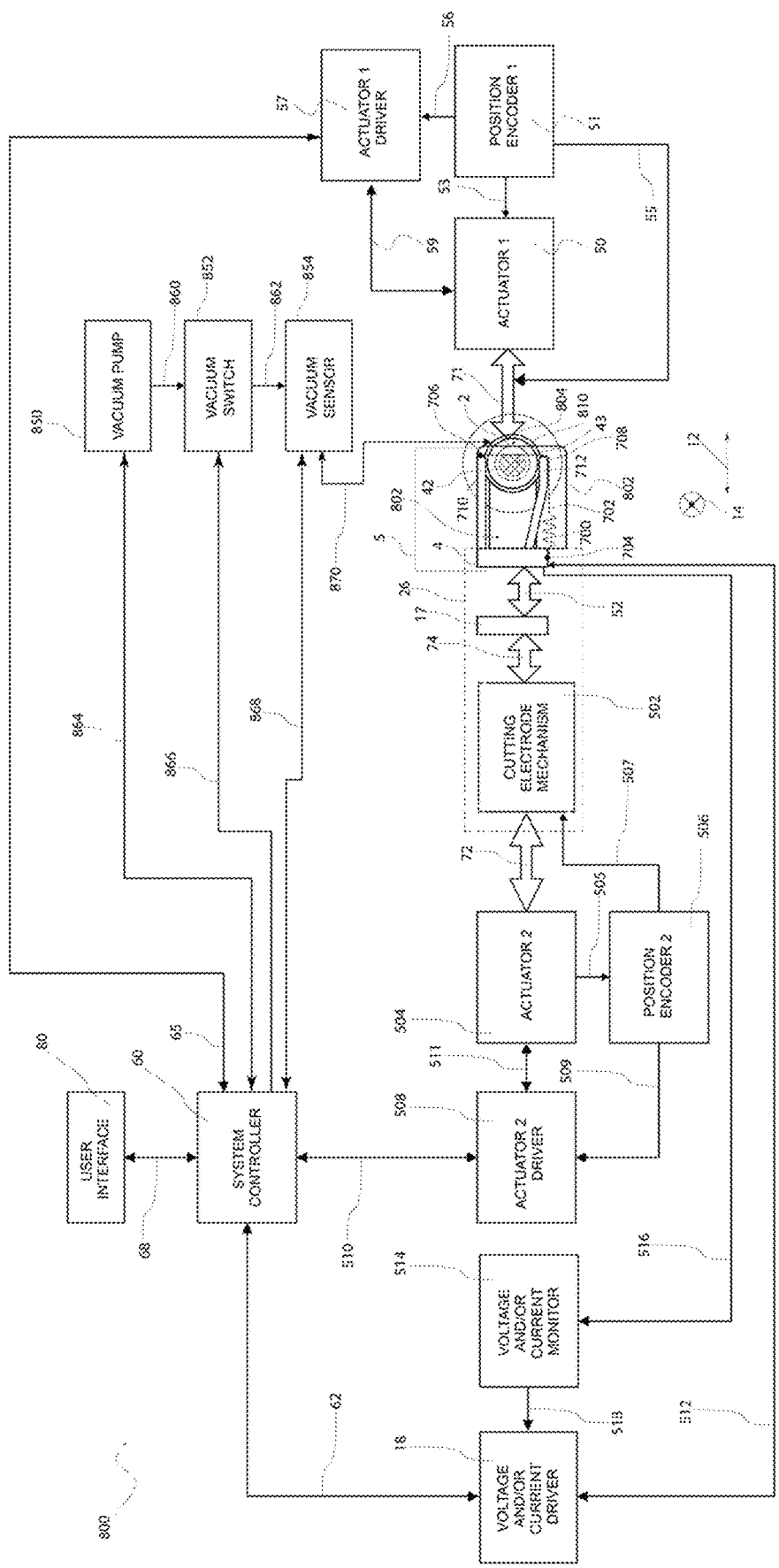
FIG. 6 is directed at a system to incise target tissue structure, in accordance with embodiments of the present disclosure.

FIG. 6 shows a system to incise tissue; such as ocular tissue, including corneal, limbal, and stromal tissue, system 800. System 800 may comprise a tensioned electrode assembly 5 similar to that of FIGS. 4 & 5. Electrode assembly 4 may be coupled to electrode mount 17 via coupler 52. By way of non-limiting example, coupler 52 may be made to be at least partially electrically insulated. Electrode assembly 4 may comprise arms 710 & 712, electrode 702, and tensioning element 700, which may be operatively coupled to electrode 702 and affixed via attachments 704 & 706 to create tensioned electrode assembly 5 such that tensioning element 700 may allow electrode 702 to stretch while in contact with tissue 2. Attachments 704 and/or 706 may be achieved via soldering, brazing, adhering, compression fitting, clamping, and combinations thereof. Radii 708 located atop arms 710 & 712 may provide a smooth surface for electrode 702 while it stretches in order to avoid excessive strain as might be experienced at a sharper corner. Tensioning element 700 may be connected directly to an electrically conductive portion of electrode 4, or alternately to a subsequent element to which to comprise electrode 702; such as coupler 52 or electrode mount 17. An incision may be made by moving along axis of motion 12. In the instant exemplary configuration, tensioned electrode assembly 5 may be comprised of elements 700, 702, 704, 706, 708, 710, and 712; all of which may be at least partially constructed from an at least a partially conductive material and thus may be held at about the same voltage by driver 18 (not shown) and all of which may be considered to comprise tensioned electrode assembly 5. Alternately, electrode assembly 4 and tensioned electrode assembly 5 may be the same. Alternately, some of the aforementioned elements may be comprised at least partially of an electrically insulating material and thus may not be at the same electrical potential as the other elements comprised of at least partially electrically conductive material and electrode assembly 4 may be considered to be only those elements comprising an at least partially electrically conductive material and be a subsystem of an tensioned electrode assembly 5, as shown. By way of non-limiting example, tensioning element 700 may be a spring, a coil spring, a leaf spring, a torsion spring, an elastic mesh or web, a hinge, a living hinge, and combinations thereof. A torsion spring may be such as that found in a staple remover. By way of non-limiting example, an at least partially electrically conductive electrode material may be selected from the group consisting of: tungsten, nitinol, steel, copper, brass, titanium, stainless steel, beryllium-copper alloy, cupronickel alloy, palladium, platinum, platinum-iridium, silver, aluminum, and combinations thereof. Alternately, an electrode 702 may be at least partially comprised a wire composed of the same material. Alternately, an electrode assembly 4 may be at least partially comprised of elements composed of electrically insulating materials. Alternately, an electrode assembly 4 may be coated in certain areas to preclude conduction and/or incision in said areas. Similarly, tubing may be used in lieu of a coating to insulate areas of an electrode assembly. By way of non-limiting example, such a coating or tubing may selected from the group consisting of: polyimide, PTFE (e.g., Teflon), polyethylene, polypropylene, polycarbonate, poly(methyl methacrylate), acrylonitrile butadiene styrene, polyamide, polylactide, polyoxymethylene, polyether ether ketone, polyvinyl chloride, polylactic acid, glass, ceramic, and combinations thereof. A return electrode (not shown) may be placed on or near the eye of the patient and connected to driver 18. A serial load of between ~150Ω and ~500Ω may be placed in-line with the electrode in order to provide for current limitation. Coupler 52 may be operatively coupled to cutting electrode mechanism 502 via coupler 74. Alternately, by way of non-limiting example, elements electrode 4, coupler 52, electrode mount 17, cutting electrode mechanism 502, coupler 74, or a subset thereof may be packaged into a probe body 26 as a disposable module configured to engage system 800 via couplers 71 & 72, which in turn may comprise mating features compatible with those of actuators 50 & 504, respectively; such as threads, a clasp, a snap fitting, and combinations thereof. Actuator 504 may provide an axis of motion (or equivalently, a "translation" along a direction of motion, e.g. axis of motion 14) be coupled to position encoder 51 via connection 53 and both position encoder 51 and actuator 50 may be connected to a translation device and/or actuator driver 57 via connections 55 & 59, respectively. By way of non-limiting example, connections 55 & 507 may comprise at least one of the following, a mechanical coupler, an electrical coupler, a magnetic coupler, and an optical coupler. Actuator 504 may also provide an axis of motion (e.g. axis of motion 12) and be coupled to position encoder 506 via connection 505 and both position encoder 506 and actuator 504 may be connected to actuator driver 508 via connections 509 & 511, respectively. It should be noted that only a single axis of motion may be relied on to practice certain embodiments of the present disclosure, such as in the creation of a corneal flap utilizing a single incision. The axes of motion for actuators 50 & 504, axes of motion 14 & 12, respectively, may be configured to be orthogonal or at least not colinear. Actuators 504 & 50 may be configured to actuate tensioned electrode assembly 5, or portions thereof, along axes of motion 12 & 14. Position encoders 51 & 506 may be mechanically coupled, via connections 55 & 507, respectively, to the module onto which electrode assembly 4 is mechanically coupled in order better provide reliable position information than non-collocated sensors may provide. Alternately, Actuator 50 may be configured to correspond to (or, "move along") axis of motion 14 and be made to actuate (or "translate") a contact plate 804 and connection 55 may be made with contact plate 804, or structure supporting contact plate 804. Driver 18 may be configured to provide controlled voltage and/or controlled current to electrode 4. Driver 18 may provide an alternating voltage and/or current waveform to electrode 702. The type of such a waveform may be, by way of non-limiting examples; selected from the group consisting of: pulsatile, sinusoidal, a square, sawtooth, triangular, fixed frequency, variable frequency, and combinations thereof. Driver 18 may be configured to supply a waveform with a peak-to-peak full range voltage of between ~50V and ~1000V. Alternately, driver 18 may be configured to supply a waveform with a peak-to-peak full range voltage of between ~200V and ~500V. Driver 18 may be configured to supply a waveform with a carrier (or "base") frequency of between ~10 kHz and ~10 MHz. Alternately, driver 18 may be configured to supply a waveform frequency of between ~500 kHz and ~2 MHz. Alternately, driver 18 may be configured to supply a waveform frequency of between ~800 kHz and ~1.2 MHz. A burst duration may also be used and may further depend on the electrode velocity, $v_t$. Driver 18 may be further modulated to comprise bursts of pulses at a modulation frequency of between ~100 Hz and ~3 MHz to create a duty cycle. The duty cycle may be between ~0.01% and ~100%. Alternately, the duty cycle may be between ~50% and ~100%. Alternately, the duty cycle may be between ~95% and ~100%. Driver 18 may be configured to supply an average power of between ~1 W and ~25 W. Alternately, driver 18 may be configured to supply an average power of between ~12 W and ~18 W. Driver 18 may be configured to supply an energy per cycle (or, equivalently, an "energy per pulse") of between ~1 µJ and ~100 µJ. Alternately, driver 18 may be configured to supply an energy per cycle of between ~5 µJ and ~50 µJ. Alternately, driver 18 may be configured to supply an energy per cycle of between ~10 µJ and ~20 µJ.

In some embodiments, a flap may be described as an incision yielding a "flap" of tissue that maybe lifted and pivot on a "hinge" to provide access to the tissue beneath it. By way of non-limiting example, cutting a segment of tissue to depth of 130 µm and razing a plane at that depth beneath a tissue surface may yield a flap with an uncut edge as its hinge. A flap may be amputated by completing the uncut edge of the exemplary incision. In some embodiments, a pocket may be described as an incision that separates a first depth (or layer) of tissue from a second depth (or layer) of a segment of tissue without necessarily creating a flap. By way of further non-limiting example, cutting one side of a tissue to a depth and razing a plane at that depth beneath a tissue surface may yield a pocket.

In some embodiments, significant drops of the input impedance of driver 18 due to plasma discharge at electrode 702 may cause local current spiking, which in turn may destroy the electrode and/or cause damage tissue. The power delivered (or, equivalently "delivered power", or equivalently "maximum power output") to the electrode may be limited instead to avoid such situations. An average power suitable for practicing embodiments of the present disclosure may be between ~1 W·mm$^{-1}$~10 W·mm$^{-1}$, especially during glow discharge. The delivered power may be higher during the initial exposure to better ensure commencement of dielectric breakdown. Alternately, a voltage and/or current waveform (or alternately, a power control signal) used to power said electrode 702 may be further modulated, or adjusted, such that it is proportional to the instant or expected length of tissue engagement and/or the electrode translation velocity, $v_t$.

By way of non-limiting example, when incising a cornea, a voltage may be increased from an initial value that corresponds to when electrode 702 is about to initially engage, or initially engages, or is expected to initially engage the tissue and is nominally directed towards a region of more central cornea to a higher voltage that corresponds to when electrode 702 is traversing or expected to traverse the central cornea and thus have a relatively greater length of tissue engagement than it did initially; said electrode voltage may be then made to decrease as electrode 702 continues traversing cornea 2 and incising tissue with inherently less engagement length, said decrease may be configured to be the opposite of the initial increase, but need not be. The position of an electrode 702 within a cornea 2 may be inferred using an encoder in the translation subsystem, as described elsewhere herein. In an embodiment, the voltage provided by driver 18 may be configured to deliver a maximum peak-to-peak bipolar nominally sinusoidal voltage of ~500V (comprising both ~+250V and ~−250V amplitudes, relative to a nominal neutral voltage, which need not be a ground voltage) with a PRF (or "carrier frequency") of ~1 MHz that may ramp from ~0V to maximum amplitude during the initial ~50 µs of a translation and then may ramp back to ~0V during the final ~100 µs of a translation, such as may be useful when tensioned electrode assembly 5 is comprised of an ~10 mm long, ~Ø10 µm, ~99.99% pure tungsten wire for the incisional portion of electrode 702 that is tensioned to ~300 mN by tensioning element 700 and translated at a maximum rate (i.e., $v_{t,max}$) of ~300 mm·s$^{-1}$ along direction 12 with a constant acceleration of ~2,000 mm·s$^{-2}$ with an initial electrode location that is between ~4 mm and ~7 mm from the closest aspect of the target tissue to be incised. It is to be noted that such a constant acceleration may yield a linear velocity profile in which an electrode may be brought to rest inside of the target tissue, such as may be required to create a flap or a lenticule as opposed to a complete incision, as will be described elsewhere herein.

In some embodiments, monitor 514 may be configured to monitor the voltage and/or current suppled to electrode assembly 4 via connection 516 and provide data regarding said voltage and/or current to driver 18 via connection 518. The data regarding voltage and/or current of electrode assembly 4 may be in the form of signals from a comparator. System controller 60 may be operatively coupled to driver 18 via connection 62, which is at least a unidirectional connection. Alternately, connection 62 may also be a bidirectional connection wherein controller 60 is able to sense and/or respond to at least a signal from driver 18. Signals from monitor 514 may be also provided to system controller 60 and acted upon thereby to control the incision created by electrode assembly 4. Monitor 514 may reside within system controller 60, and/or communicate with system controller 60 via driver 18. Such a signal may be a safety signal related to a sensed voltage or current, such as when said voltage or current is outside of prescribed bounds. In a further alternate embodiment, driver 18 and/or monitor 514 may provide feedback to controller 60 or use such feedback internally. Such feedback may be, by way of non-limiting example, EMF or current feedback and may be useful in determining when electrode assembly 4 contacts tissue and/or the status of the plasma. Such status may be, for example, whether or not the plasma in the glow discharge regime or not. Connection 65 connects controller 60 with actuator 50 and is at least a unidirectional connection. Actuator 50 may be comprised of at least one electrical motor and may further comprise a positional encoder. Connection 65 may alternately be a bidirectional connection wherein signals are shared between controller 60 and actuator 50, such as position, velocity, acceleration, out of bounds errors, etc. In a further alternate embodiment, actuator 50 may provide feedback to controller 60 or use such feedback internally and may share such feedback as signals with controller 60. Such feedback may be, by way of non-limiting example, force feedback and may be useful in determining when electrode assembly 4 contacts tissue or when it imparts excessive force on the tissue to be incised. Likewise, connection 67 connects controller 60 with power supply 70 and is at least a unidirectional connection. In a further alternate embodiment, power supply 70 may provide feedback to controller 60 or use such feedback internally and may share such feedback as signals with controller 60. Such feedback may be, by way of non-limiting example, an error signal. Such error signals may be temperature errors, input voltage errors, output voltage errors, input current errors, output current errors, etc. Likewise, connection 68 connects controller 60 with user interface 80 and is at least a unidirectional connection from user interface 80 to controller 80. In a further alternate embodiment, user interface 80 may provide feedback to controller 60 or use such feedback internally and may share such feedback as signals with controller 60. For example, user interface 80 may be a graphical user interface or a button or a foot pedal used to signal actuator 50 to move electrode assembly 4 and incise tissue. Actuator drivers 57 & 508 may be connected to system controller 60 via connections 65 & 510, respectively. User interface 80 may be connected to system controller 60 via connection 68 and user instructions sent therethrough.

In some embodiments, the system controller 60 comprises a processor configured with instructions to determine a profile of tissue to be removed from the eye to provide refractive correction. The processor can be configured to determine the shape profile of one or more plates used to provide a refractive correction for the patient. Also although reference is made to controller 60, controller 60 may comprise a component of a distributed computing system and may be operatively connected to one or more processors as described herein, such as a distributed processing system.

In some embodiments, system 800 may further comprise contact plate 804, a support element 802, a suction element 810, and accompanying vacuum apparatus which may be used to fixate a contact tissue 2. An incision 42 may be made in tissue 2 (the cornea and/or corneal stroma in the instant exemplary embodiment) by moving at least portions of tensioned electrode assembly 5 along axis of motion 12 to create bed 43 using actuator 504. A contact plate 804 may be incorporated to applanate the cornea by moving it onto the anterior surface of the cornea along axes of motion 14 by means of actuator 50. Contact plate 804 may further comprise a contact surface 806 (not shown). Said contact plate 804 may be used to applanate the cornea, especially when contact surface 806 is nominally about planar. By way of non-limiting example, contact plate 804 may be configured to be a planar glass window to allow visibility therethrough. By way of non-limiting example, contact plate 804 may be composed of a material selected from the group consisting of: glass, crystalline, ceramic, metal, polymer, and combinations thereof. A contact element 808 (not shown) may be placed on the distal surface of contact plate 804 to provide a clean and/or sterile surface for contact with tissue 2 and may be configured as a thin, conformal, peel-and-stick sterile barrier, which may also be disposable. By way of non-limiting example, contact element 808 may be composed of a material selected from the group consisting of: polyethylene (PE), polyvinylchloride (PVC), polypropene (PP), oriented PP (OPP), biaxially oriented PP (BOPP), polyethylene terephthalate (PET), and combinations thereof. Contact plate 804 may be supported, at least in part, by support 802. Support 802 may further at least partially support elements of tensioned electrode assembly 5, such as arms 710 & 712 and thereby also supporting electrode 702 and tensioning element 700 to form a at least a portion of electrode assembly 4 and tensioned electrode assembly 5. As such, arms 710 & 712 may be considered to be a support structure for electrode 702. Alternately, support 802 may be operatively coupled to probe body 26 and/or sheath 6. Alternately, contact plate 804 may be made to move along with support 802 relative to tissue 2. A suction element 810 may be used to stabilize the eye containing tissue 2 relative to contact plate 804 and/or electrode 4. Suction element 810 may be configured as a nominally open annular ring, as shown, or alternately by any other applicable construction to achieve fixation to the eye, such as a single open pocket, or a plurality of open pockets. Suction element 810 may be operatively coupled to vacuum pump 850 via vacuum line 870 to provide a negative pressure within suction element 810. For patient safety and system reliability, a vacuum switch 852 and/or a vacuum sensor 854 may be placed in between suction element 810 and vacuum pump 850, and connected via connections 860 and 862, respectively. System controller 60 may be connected to vacuum pump 850, vacuum switch 852, and vacuum sensor 854 via electrical connections 864, 866, and 868, respectively. In the instant configuration, actuator 50 may be configured to correspond to axis of motion 14 and be made to actuate (or "translate") a contact plate 804 and connection 55 may be made with contact plate 804, or such structure supporting contact plate 804. Contact plate 804 may be translated at a rate, or velocity of between ~0.1 mm·s$^{-1}$ and ~1000 mm·s$^{-1}$, and in an alternate embodiment it may be translated at a rate of between ~10 mm·s$^{-1}$ and ~100 mm·s$^{-1}$. The motion corresponding to actuator 50 may be configured to be at least partially simultaneous with of actuator 504, or the velocity profiles thereof.

In some embodiments, system 800 may be further configured such that a tensioned electrode assembly 5 that at least partially comprises an electrode 702. Electrode 702 may comprise a tungsten wire of ~12.5 µm in diameter and at least ~99% purity that runs across arms 710 & 712 to form a bridge distance of ~12 mm and uses a mechanical coil spring imparting a tensional force of ~300 mN on electrode 702, for example.

Figure 7:
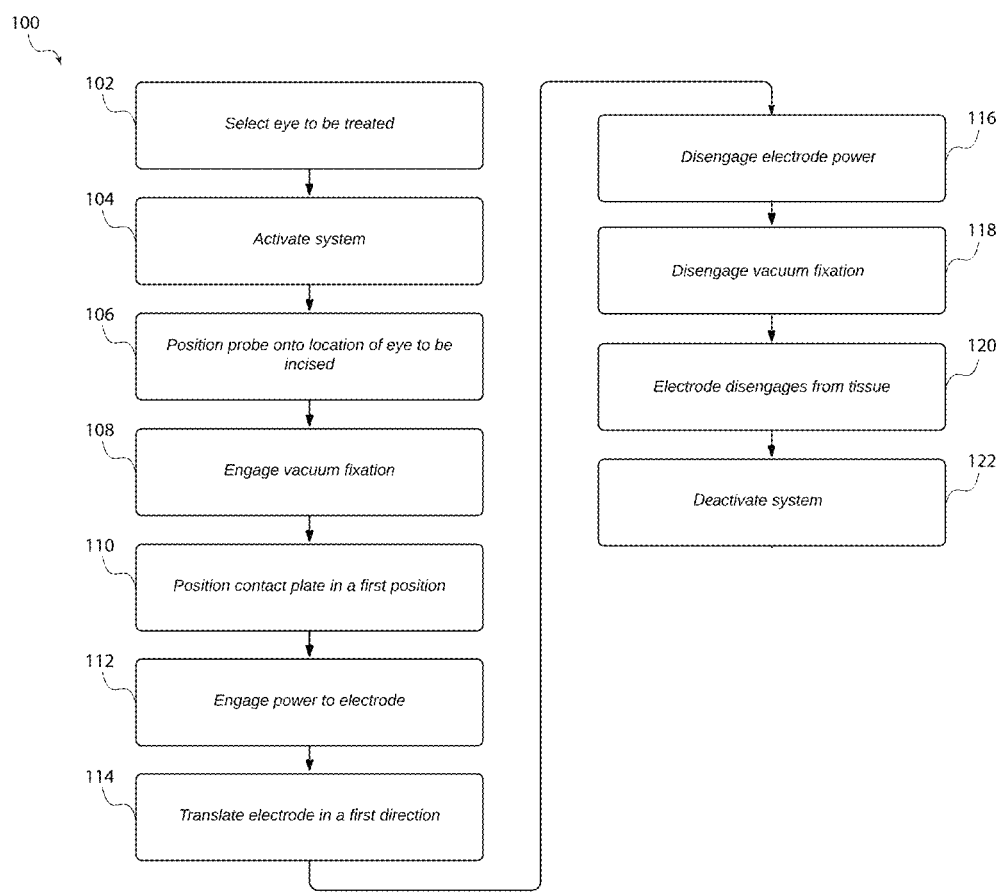
FIG. 7 depicts a flow chart describing steps to practice a method, in accordance with embodiments of the present disclosure.
Figure 9:
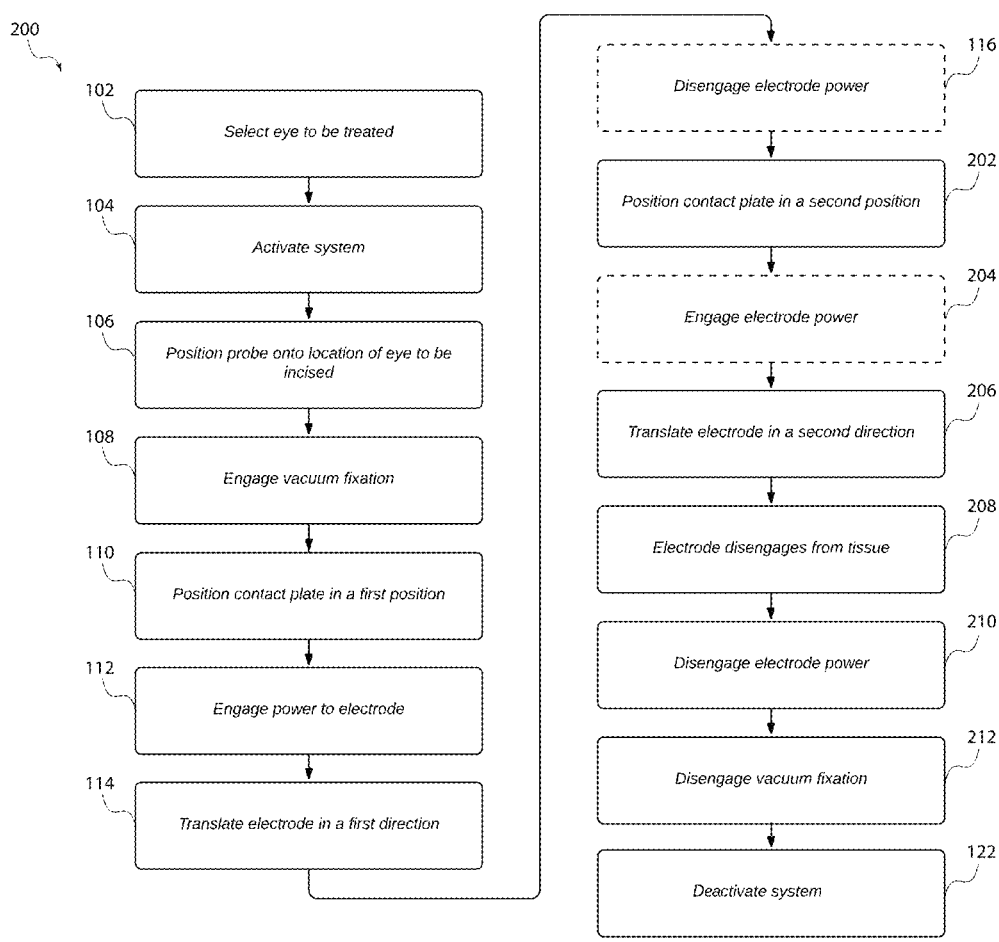
FIG. 9 depicts a flow chart describing steps of a method, in accordance with embodiments of the present disclosure.

In some embodiments, an incision may form a flap or a pocket or combinations thereof based upon whether or not the electrode cutting width is about greater than or about equal to the lateral extent of the target tissue structure to be incised and whether or not the electrode is made to penetrate outwards laterally from the tissue. That is, a flap may be made in an anterior aspect of a cornea by applanating or otherwise compressing said anterior corneal surface using contact plate 804 to yield a lateral dimension for incision 42 of between ~3 mm and ~11 mm, or alternately of between ~8 mm and ~10 mm, all of which may be less than the aforementioned bridge distance to provide a flap incision. A flap incision may be configured to provide a D-shaped incision 42, as shown, where the straight segment of the D-shaped incision may be a hinge portion. Similarly, a pocket incision may be made if the electrode bridge distance is less than the lateral extent of the compressed cornea presented to the electrode. Alternately, a combination flap/pocket incision may be created using a pocket incision configuration and allowing the electrode to traverse the entire distance through the cornea and may yield an incision shaped as a fully-rounded rectangle, or a partially-rounded rectangle (e.g. when configured to comprise a straight uncut portion). In an alternate embodiment, driver 18 may be configured to supply a sinusoidal waveform that may have a peak-to-peak full range voltage of ~250V at a frequency of ~1 MHz and a power limit of ~15 W to incise corneal tissue at an electrode translation rate of between ~200 mm·s$^{-1}$ and ~0 mm·s$^{-1}$ (i.e. $v_t$=~0 mm·s$^{-1}$ while electrode is stopped at end of incision) along direction of motion 12 and utilizing steps 102 through 122 of flowcharts 100 & 200, as shown in FIGS. 7 & 9. Step 202 of flowchart 200 may be utilized for the discontinuation of power to an electrode in coordination with the motion of the electrode and contact plate 804 such that the electrode is provided a voltage of nominally ~0V during the interim period between the electrode moving in a first direction and then moving in a second direction, such as might be the case if contact plate 804 is moved along direction of motion 14 in order to remove a portion of tissue (e.g. a "lenticule" of intrastromal tissue). Alternately, the electrode voltage and/or power may be made a function of the electrode velocity, and/or position, and/or cutting extent, as described elsewhere herein.

Alternately, a variable acceleration may be utilized to create a motion profile for an electrode, resulting in a nonlinear velocity profile. Such a motion profile may require a higher order control model and incorporate "jerk" and/or "snap" and/or "crackle" and/or "pop" factors to provide an asymmetrical acceleration/deceleration such that the range of $v_t$ in the initial ~50 µs is similar to that of the final ~10 µs, by way of non-limiting example.

The velocity and/or velocity profile and/or the active incision width may be taken into account when controlling (e.g., "modulating") the power to the electrode.

By way of non-limiting example, the power to an electrode 702 may be adjusted by choosing a maximum value of a parameter selected from the group consisting of: a voltage, a current, a carrier frequency, a modulation frequency, a duty cycle, a power setpoint, a power limit, an energy per pulse setpoint, an energy per pulse limit, and combinations thereof.

By way of non-limiting example, a modulation relationship describing the controlled power output of an electrode 702 driven by driver 18 may be selected from the list comprised of the following; a fixed relationship, a constant relationship, a linear relationship, a nonlinear relationship, a logarithmic relationship, a sinusoidal relationship, an exponential relationship, a polynomial relationship, and combinations thereof. Said relationships may be direct or inverse, depending upon the immediate system configuration and determinable using the descriptions and equations included herein. Said controlled power output may be considered to be the instantaneous power and/or the average power and/or the peak power. Said modulation may be achieved via control of driver 18, by way of non-limiting example. The term modulation is used herein to indicate an alteration of an otherwise consistent output, waveform, or signal. As used herein, "modulating" a waveform is equivalent to "enveloping" a waveform and "modulation envelope" is equivalent to "envelope." Alternately, no modulation may be used to envelope a waveform, including an intrinsically pulsatile waveform.

By way of non-limiting example, when creating a corneal flap incision, a duty cycle $D_c$ may be modulated by utilizing a compound relationship representing the active incision width $y_a$ which may be modeled as a chord length of a circle of radius R that is turn a function of the distance into the target tissue $x_c$ (i.e., the height of the circular cap) multiplied by the velocity profile $v_t$ to yield $$D_c \propto v_t y \rightarrow 2v_t[x_c(2R - x_c)]^{\frac{1}{2}},$$

which may be normalized using the nominal values for R and $v_{t,max}$ to provide a generic envelope function.

Alternatively, the voltage U required for vaporization may be regarded as $$U = r_e\sqrt{\frac{\rho C \Delta T \gamma}{\tau}\ln\left(\frac{L}{r_e}\right)},$$

and at least a component of a modulation relationship for electrode voltage V provided by driver 18 to an electrode 702 may be $$V \propto \sqrt{\ln(y_a)} \rightarrow 2\sqrt{x_c(2R-x_c)}/\sqrt{2}.$$

It should be noted that the preceding examples at least partially involve exponential relationships, as the radical is the inverse function to the of taking of a power.

Alternately, an energy per cycle provided by driver 18 to an electrode 702 may be configured to deliver an energy per cycle that may be at least partially dependent on the value of $v_t$ and/or at least partially dependent on the value of the active incision width $y_a$.

Alternately, a duty cycle provided by driver 18 to an electrode 702 may be configured to deliver a duty cycle that may be at least partially dependent on the value of $v_t$ and/or at least partially dependent on the value of the active incision width $y_a$.

Alternately, a voltage provided by driver 18 to an electrode 702 may be configured to deliver a voltage that may be at least partially dependent on the value of $v_t$ and/or at least partially dependent on the value of the active incision width $y_a$.

Alternately, a current limit provided by driver 18 to an electrode 702 may be configured to deliver a current limit that may be at least partially dependent on the value of $v_t$ and/or at least partially dependent on the value of the active incision width $y_a$.

Alternately, a power limit or setpoint provided by driver 18 to an electrode 702 may be configured to deliver a power limit or setpoint that may be at least partially dependent on the value of $v_t$ and/or at least partially dependent on the value of the active incision width $y_a$.

Alternately, a PRF provided by driver 18 to an electrode 702 may be configured to deliver a PRF that may be at least partially dependent on the value of $v_t$ and/or at least partially dependent on the value of the active incision width $y_a$.

Alternately, $v_t$ may be at least partially dependent upon the active incision width $y_a$ and/or $x_c$, where $y_a = 2\sqrt{x_c(2R-x_c)}$, as described elsewhere herein.

Alternately, such as may be useful when tensioned electrode assembly 5 is comprised of an ~10 mm long, ~Ø20 μm, ~99.99% pure tungsten wire for the incisional portion of electrode 702 that is tensioned to ~300 mN by tensioning element 700 and translated at a maximum rate of ~200 mm·s$^{-1}$ along direction 12 with a constant acceleration of ~1,000 mm·s$^{-2}$ with an initial electrode location that is between ~2 mm and ~4 mm from the closest aspect of the target tissue to be incised (i.e., the point nearest the electrode along its axis of motion), a voltage provided by driver 18 may be configured to deliver a maximum peak-to-peak bipolar nominally sinusoidal voltage of ~600V (comprising both ~+300V and ~−300V amplitudes, relative to a nominal neutral voltage) with a PRF (or "carrier frequency") of ~1 MHz that linearly ramps from ~0V to maximum amplitude during the initial ~50 μs of a translation and ramps back to ~0V during the final ~50 μs of a translation.

In a further alternate embodiment, a duty cycle provided by driver 18 may be configured to deliver a duty cycle that ramps from ~0% to maximum amplitude of between ~70% and ~100% during the initial ~50 μs of a translation and ramps back to ~0% during the final ~10 μs of a translation. Said duty cycle may be created utilizing a modulation frequency, such as a square-wave gating function. Sais square-wave gating function may be configured to have variable "on" and/or "off" times. The relationship of the variable "on" and/or "off" times may be as described elsewhere herein regarding the relationships for describing the controlled power output of an electrode.

In a further alternate embodiment, a duty cycle provided by driver 18 may be configured to deliver a duty cycle that may be at least partially dependent on the value of $v_t$ and may ramp from ~0% to maximum amplitude of between ~70% and ~100% while the velocity of the electrode is increased from rest (i.e. $v_t=0$ mm·s$^{-1}$) to its maximum value and the duty cycle is then decreased to ~0% when the electrode velocity is reduced back to rest.

In a further alternate embodiment, the maximum power output provided by driver 18 may be configured to deliver a maximum power output that is that may be at least partially dependent on the value of $v_t$ and may ramp from ~0% to maximum amplitude of between ~70% and ~100% while the velocity of the electrode is increased from rest to its maximum value and the maximum power output is then decreased to ~0% when the electrode velocity is reduced back to rest.

In a further alternate embodiment, a voltage provided by driver 18 may be configured to deliver a voltage that may be at least partially dependent on the value of $v_t$ and may ramp from ~0% to maximum amplitude of between ~70% and ~100% while the velocity of the electrode is increased from rest to its maximum value and the duty cycle then decreased to ~0% when the electrode velocity is reduced back to rest.

FIG. 7 describes a method of incising tissue. Flowchart 100 comprises steps 102-122 that may be completed serially, or in any suitable order. At a step 102 an eye is selected for treatment. Step 104 involves activating the system, and step 106 involves positioning a probe onto the tissue to be treated. Step 108 involves activating a vacuum system to fixate tissue with respect to the probe (such as via the vacuum system described earlier). Step 110 involves positioning a contact plate onto the tissue in a first position. Step 112 involves power being applied to an electrode. Step 114 involves translating (or "moving" or "actuating") said electrode in a first direction (such as along axis of motion 12, the "+x-direction"). Step 116 involves discontinuing power to the electrode. Step 118 involves disengaging the vacuum fixation and freeing the tissue and disengaging the eye being treated. Step 120 involves an electrode disengaging from a tissue just incised. Step 122 involves deactivating the system and disengaging it from the eye. A thin electrode may be allowed to break as the system is disengaged from the patient. Alternately said electrode may be made to translate in a second direction, nominally opposite of said first direction. Alternately, step 108 and step 110 can be exchanged and power applied to the electrode once it is in contact with tissue 2. Alternately, steps 116 through 120 may be eliminated to create an excision. Alternately, steps 116 & 118 may be eliminated if there is only low risk of collateral damage due to tissue heating while the actuator changes direction. Alternately, step 116 may involve a tapered reduction in power to the electrode, and step 112 may involve a tapered increase in power to the electrode, as described elsewhere herein.

Although FIG. 7 shows a method of incising tissue in accordance with some embodiments, one of ordinary skill in the art will recognize that many adaptations and variations can be made in accordance with the present disclosure. For example, the steps can be performed in any suitable order, some of the steps repeated, some of the steps omitted, and combinations thereof.

In some embodiments, a processor as described herein is configured with instructions to perform one or more of the steps of the method of FIG. 7.

Figure 8A:
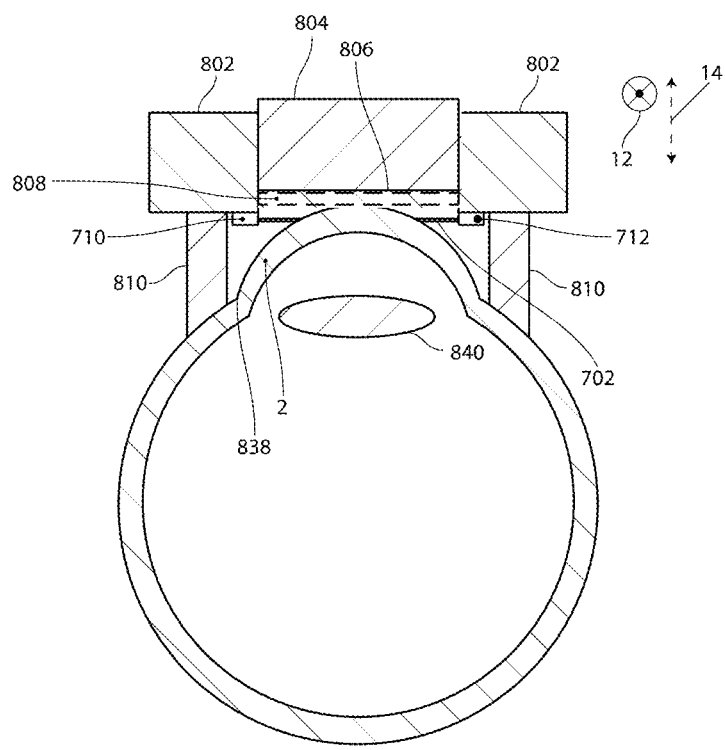
FIGS. 8A through 8D are directed at a system to incise a target tissue structure, in accordance with embodiments of the present disclosure.

FIGS. 8A through 8D are directed at details in accordance with embodiments of the present disclosure, wherein a tensioned electrode assembly 5 is now shown in a view orthogonal to that of FIGS. 4 through 6, such that axis of motion 12 may now be into and out of the plane of the figure, while axis of motion 14 may be vertical, and wherein the steps of FIG. 7 may be followed. FIG. 8A shows that contact plate 804 may be configured to lie within a middle portion of support 802 and move relative to support 802 along axis of motion 14. Contact surface 806 of contact plate 804 may be about planar and about parallel to the cutting portion of electrode 702. Electrode 702 is shown as being initially behind the cornea in this view. Contact element 808 may be placed on contact surface 806 to create a sterile disposable for use only during a single procedure. Contact element 808 may nominally conform to at least a portion of contact surface 806. The portion of contact surface 806 to which contact element 808 conforms may be a center portion. Suction element 810 may be configured to contact the eye containing tissue 2 at a region nearby the outer cornea and/or the corneoscleral limbus 838, as shown, to fixate and stabilize cornea 843 (not indicated in the present figure). Alternately, suction element 810 may be made to contact at least an aspect of cornea 843 to better stabilize tissue 2 relative to the incision of electrode 702. Cornea 843 may comprise anterior corneal surface 842 and posterior corneal surface 844. In this instance, target tissue 2 may be considered to be stromal tissue within cornea 843 and contained between anterior corneal surface 842 and posterior corneal surface 844. Intraocular lens 840 is shown for the purposes of orientation and may be a natural lens or a prosthetic lens. In the present embodiment, contact element is in contact with the apex of anterior corneal surface 842 of cornea 843. Electrode assembly 4 may comprise arms 710 and 712, as well as electrode 702, as shown. The configuration of the immediate figure may represent steps 102, 104, and 106 of FIG. 7.

Figure 8B:
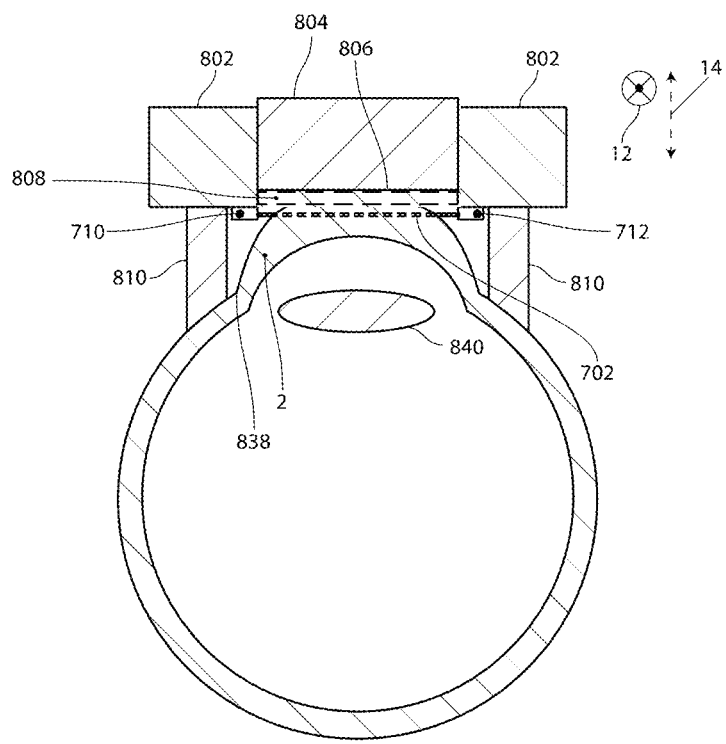

FIG. 8B shows the system of FIG. 8A, wherein contact plate 804 and therefore contact element 808 may have been moved farther along axis of motion 14 to applanate cornea 843 and tissue 2 therein. Electrode 702 may be made to incise tissue 2 by traversing a path along axis of motion 12, as has been described elsewhere herein, to create incision 45 and thereby bed 43 (not indicated in this view). The configuration of the immediate figure may represent steps 108, 110, 112, and 114 of FIG. 7.

Figure 8C:
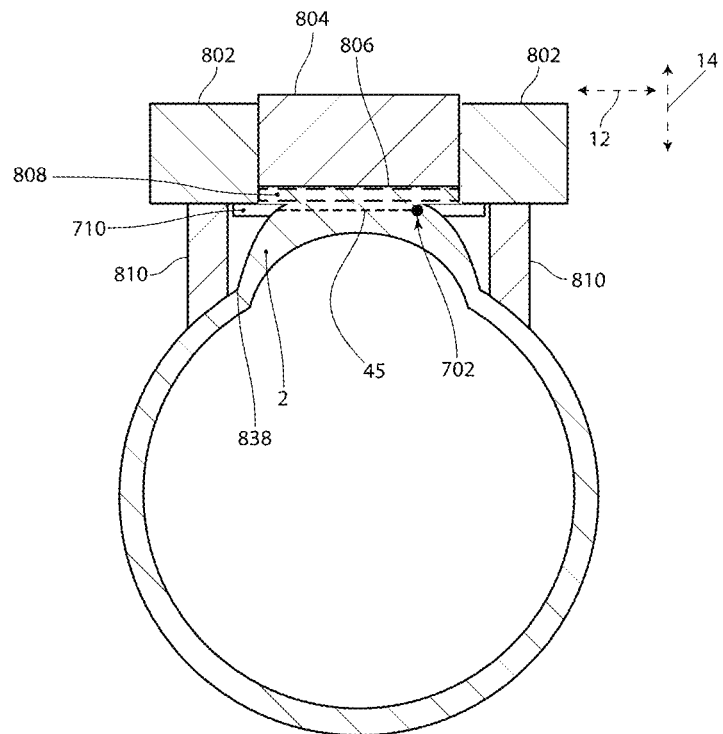

FIG. 8C shows the system of FIG. 8B in a different orientation, as evidenced by axes of motion 12 & 14, such that incision 45 is seen to be progressing through tissue 2 as electrode 702 is translated along axes of motion 12 (shown in this view as proceeding from left to right). The actuation of electrode 702 may be in its final position, such as may be the case when creating a flap incision.

Figure 8D:
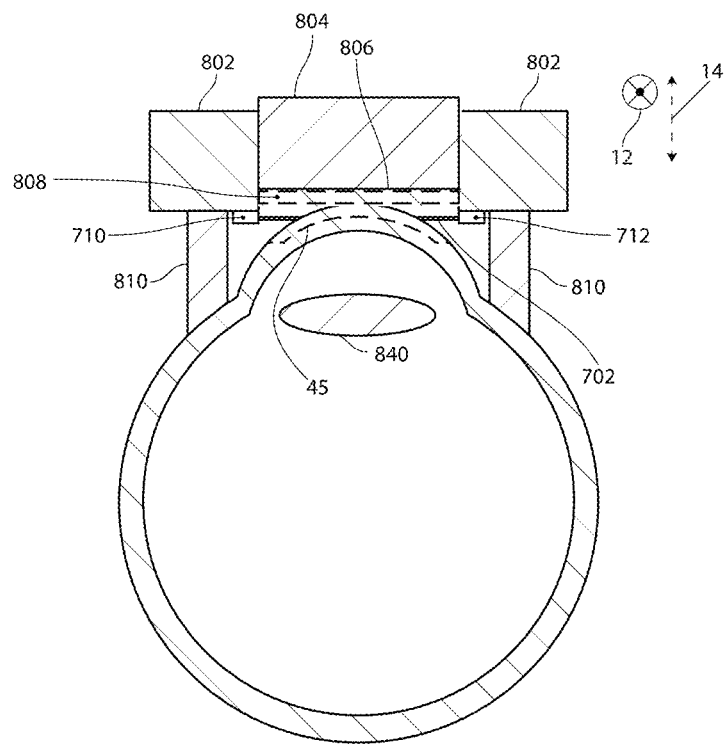

FIG. 8D shows the system of FIGS. 8A-8C, wherein contact plate 804 and therefore contact element 808 may have been moved along axis of motion 14 to just rest atop the apex of corneal surface 842, as in FIG. 8A. The immediate figure now shows incision 45, which may form a surface for bed 43 (not indicated). The surface shape of bed 43 thus created may be nominally characterized as about that of the anterior corneal surface 842. Alternately, the surface shape of the central region of bed 43 (not shown) thus created may characterized as the mean value of at least portions of the surface shapes of the anterior corneal surface 842 and the contact surface 806 (or contact element 808). Said mean may nominally be an arithmetic mean, a geometric mean, a harmonic mean, a weighted mean, or combinations thereof. The configuration of the immediate figure may represent steps 116, 118, 120, and 122 of FIG. 7.

FIG. 9 describes a method of similar to that of FIG. 7, with additional steps 202 through 212; wherein step 116 may be made optional and allow the electrode to incise during step 202. That is, alternately, steps 116 & 118 may be eliminated if there is only low risk of collateral damage due to tissue heating while the actuator changes direction and/or the strain to an unpowered electrode may cause a failure of said electrode due to the change in position of the contact plate. Step 202 involves positioning a contact plate at a second position, which may be a translation of the entire element, or a translation of at least a portion of the element. The translation of at least a portion of the element may be utilized to create a non-planar contact plate surface to provide a desired corneal deformation, as will described with regard to FIGS. 11A & 11B. Alternately, a contact plate may be interchanged at step 202 to provide a desired corneal deformation. Said corneal deformation may be intended to create a surface that defines at least a portion of a lenticule, such as bed 43, to achieve at least a portion of a desired three-dimensional tissue resection profile. Said lenticule may be subsequently removed to cause a refractive change to a cornea 843 of an eye of a patient. Step 204 may be made optional, if step 202 is removed, but may otherwise be similar to step 112. Step 206 involves translating an electrode in a second direction. Said second direction may be nominally the opposite of said first direction. Step 208 involves an electrode disengaging from tissue, such as may occur should the translation of step 206 bring the electrode outside of tissue 2. Step 210 involves disengaging power to an electrode and may be similar to step 116 of FIG. 7. Step 212 involves disengaging the vacuum fixation and freeing the tissue and disengaging the eye being treated and may be similar to step 118 of FIG. 7. Step 122 involves deactivating the system and disengaging it from the eye similar to step 122 of FIG. 7.

Although FIG. 9 shows a method of incising tissue in accordance with some embodiments, one of ordinary skill in the art will recognize that many adaptations and variations can be made in accordance with the present disclosure. For example, the steps can be performed in any suitable order, some of the steps repeated, some of the steps omitted, and combinations thereof.

In some embodiments, a processor as described herein is configured with instructions to perform one or more of the steps of the method of FIG. 9.

FIGS. 10A through 10F are directed at a system similar to that of FIGS. 8A through 8D, further configured such that the shape of contact surface 806 may be configured as other than planar and is shown as convex and additionally that a lenticule (e.g. lenticule 820) may be incised within (stromal) tissue 2 of cornea 843. The difference between a first incision profile and a second incision profile may correspond to a shape of a lenticule of tissue to be removed from the cornea to treat a refractive error of the eye.

Figure 10A:
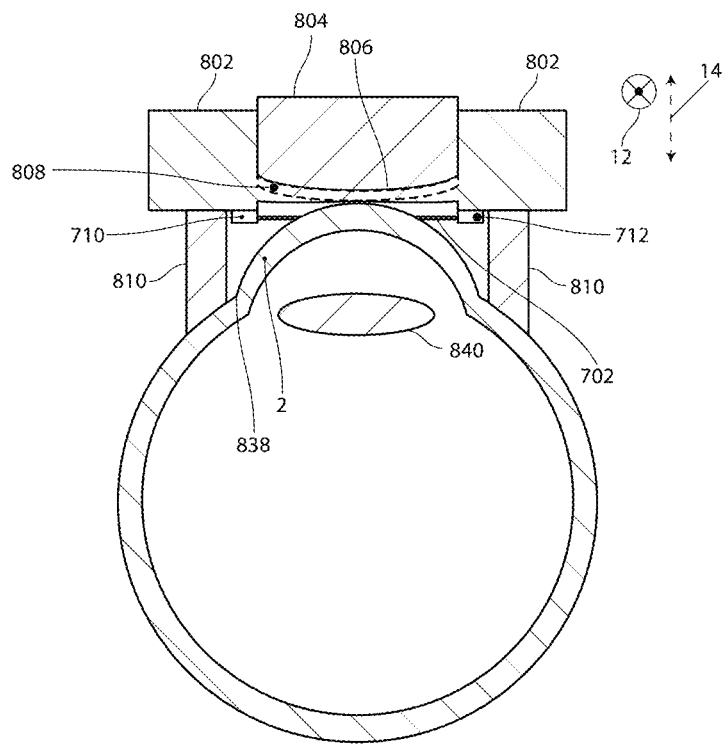
FIGS. 10A through 10F are directed at a system to incise a target tissue structure, in accordance with embodiments of the present disclosure.

FIG. 10A shows a system configured similarly to that of FIG. 8A, with the addition of a curved surface 806 on contact plate 804. Likewise, contact element 806 is placed on curved contact surface 806 and nominally matches said curvature. The configuration of the immediate figure may represent steps 102 through 108 of FIGS. 7 & 9.

Figure 10B:
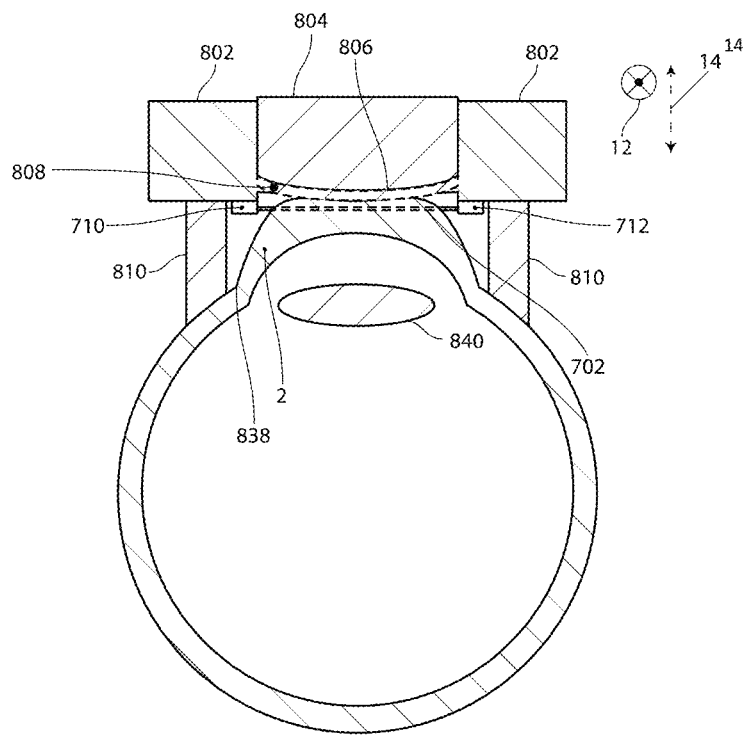

FIG. 10B shows the system of FIG. 10A, wherein contact plate 804 and therefore contact element 808 may have been moved farther along axis of motion 14 to contact cornea 843 and tissue 2 therein. Unlike the configuration of FIGS. 8A through 8C, in the configuration of the immediate figure the cornea is not necessarily applanated but caused to compress to differentially to at least partially match the curvature (or "shape" in the case where a curvature alone cannot suffice to adequately describe contact surface 806) of contact surface 806 in order to produce an incision 46. The configuration of the immediate figure may represent steps 110 through 112 of FIGS. 7 and 9.

Figure 10C:
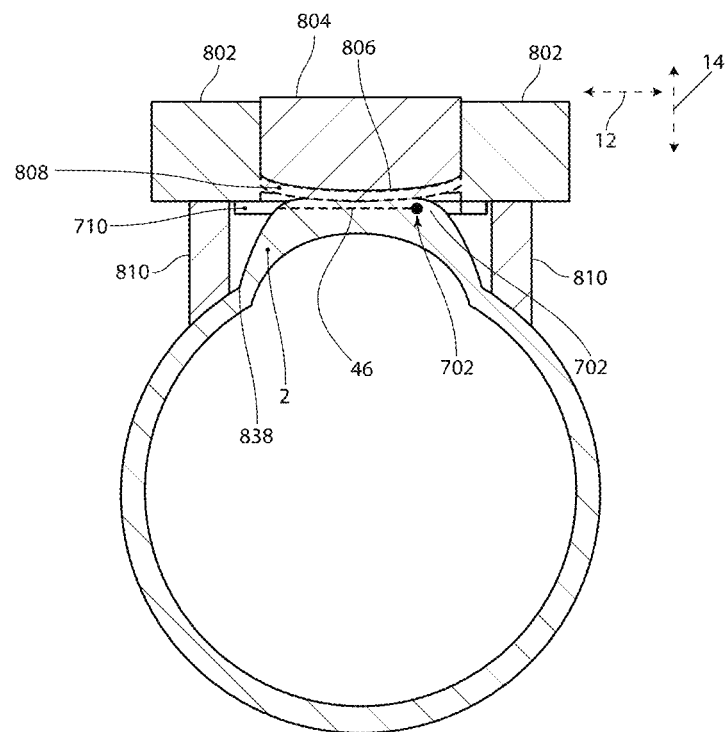

FIG. 10C shows the system of the previous FIG. 10X in a different orientation, as evidenced by axes of motion 12 and 14, such that incision 45 is seem to be progressing through tissue 2 as electrode 702 is translated along axes of motion 12 (shown in this view as proceeding from left to right). The actuation of electrode 702 may be in its final position, such as may be the case when creating a flap incision.

Figure 10D:
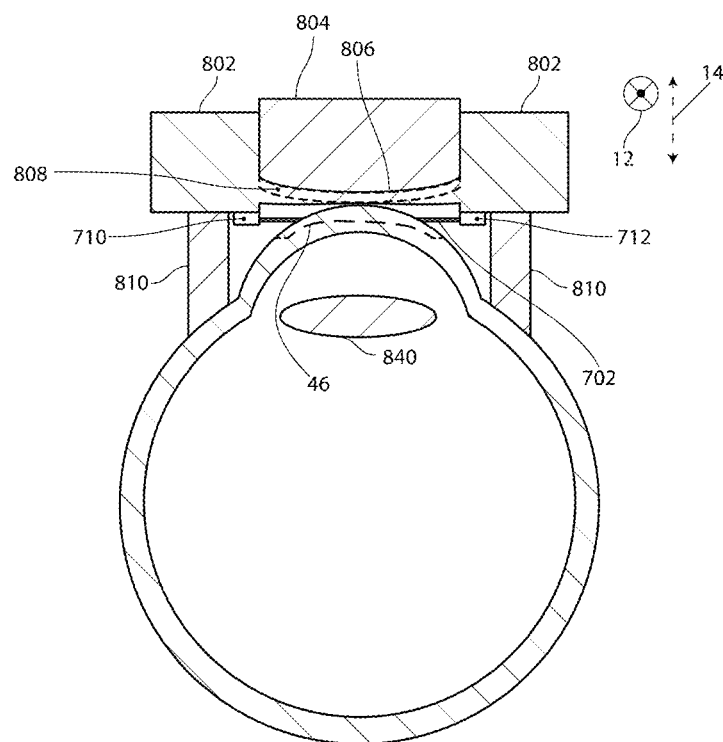

FIG. 10D shows the system of the previous FIGS. 10X, wherein contact plate 804 has been translated anteriorly and incision 46 is now indicated. Such incision 46 may form a surface for bed 44 (not indicated). The surface shape of bed 44 thus created may characterized as the mean value of the surface shapes of the anterior corneal surface 842 and the contact surface 806 (or contact element 808). Said mean may nominally be an arithmetic mean, a geometric mean, a harmonic mean, a weighted mean, or combinations thereof.

Figure 10E:
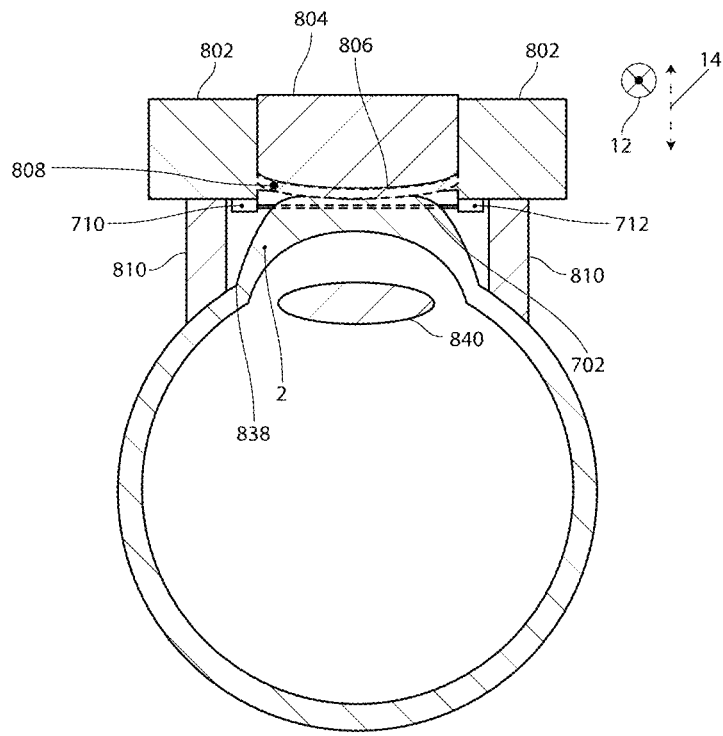

FIG. 10E shows the system of the previous FIGS. 10X, wherein a second incision, incision 45, may now be created. The configuration of the immediate figure may represent steps 202-206 of FIG. 9. Alternately, incision 45 may be created by interchanging contact plate 804, or portions thereof, to provide a different surface shape for incision 45. A flat contact surface may be used for at least one the incisions.

Figure 10F:
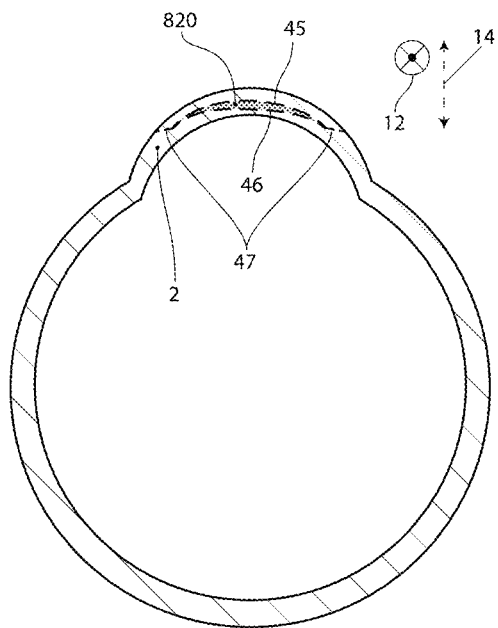

FIG. 10F shows an eye treated with the system of the previous FIGS. 10X, wherein lenticule 820 has been incised within (stromal) tissue 2 of cornea 843 and is bounded by surfaces created by incisions 45, 46. Incisions 45, 46 may comprise incisions 47 when the electrode is made to incise across the entire cornea rather than to create a pocket in the cornea. The configuration of the immediate figure may represent the outcome of completing the remaining steps of FIG. 9. The shapes of surfaces created via incisions 45, 46 may be chosen to affect a refractive correction to a cornea 843 of an eye of a patient. Said refractive correction may be defined, at least in part, by diagnostic measurements such as corneal aberrometry, ocular aberrometry, wavefront aberrometry, corneal topography, and combinations thereof, where the nominal shape of the lenticule may be defined to optically balance (or correct) the measured aberrations, such as has been described in Sekundo W. Small Incision Lenticule Extraction (SMILE) Principles, Techniques, Complication Management, and Future Concepts. 2015. Springer Cham Heidelberg; and the associated citations therein.

In some embodiments, for the cornea an approximate tissue profile for tissue to be removed may be expressed as:
$T(x,y) \sim = W(x,y)/(n-1)$ where T is the thickness in microns, W is the wavefront error in microns, n is the index of refraction of the cornea and x and y are the coordinate references corresponding to a plane, such as a plane near the pupil or vertex of the cornea. The wavefront error can be expressed in many ways, such as with an elevation in microns, or with individual Zernike coefficients for example.

Other approaches may be used to determine the thickness profile of tissue to be removed, for example with reference to the SMILE procedure as will be known to one of ordinary skill in the art.

Figure 11A:
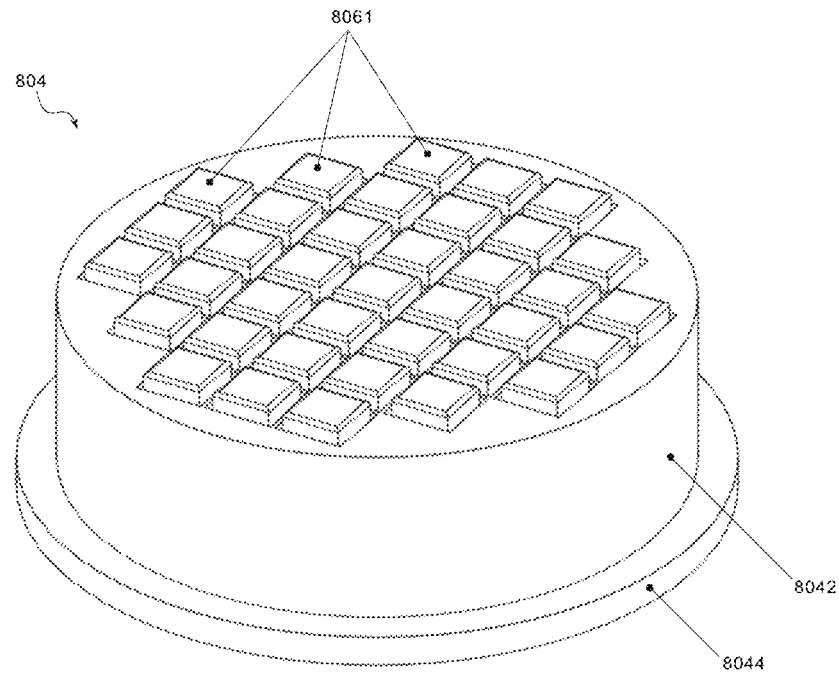
FIGS. 11A and 11B are directed at a piecewise adjustable contact element, in accordance with embodiments of the present disclosure.
Figure 11B:
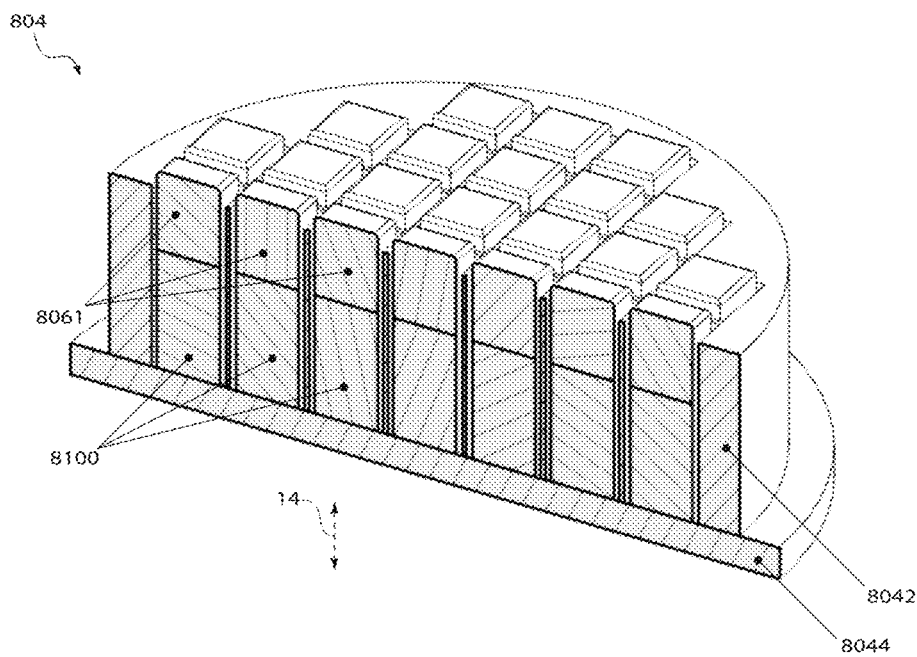

FIGS. 11A & 11B are directed at a piecewise adjustable contact plate 804 to deform the cornea in order to create a lenticule or other therapeutic incision. The adjustable contact plate 804 can be operatively coupled to the controller and configured to shape the cornea to provide refractive correction, for example with reference to small incision lenticular extraction as described herein. FIG. 11A depicts piecewise adjustable contact plate 804 comprised of sub-plates (or, equivalently, "elements") 8061, which together may be constitute a contact surface 806, that may be housed within housing 8042 and mounted to base 8044. FIG. 11B depicts the same contact plate 804 in a cross-sectional view in order to expose actuators 8100 that are operatively coupled to sub-plates 8061 within housing 8042. In the instant embodiment, sub-plates 8061 may each be affixed to an actuator 8100 to allow each subplate 8061 to be individually actuated using additional actuators and associated monitoring and control subsystems, as shown and described in regard to the system of FIG. 6 (said connections not indicated in the immediate figure). By way of non-limiting example, sub-plates 8061 may be adhered to actuators 8100 using an epoxy or be soldered. Actuators 8100 may be selected from the group consisting of: piezoelectric actuators, motors, pneumatic actuators, fluidic actuators, and combinations thereof. As shown in the exemplary embodiment, sub-elements 8062 may be constructed using a material selected from the group consisting of: a glass, a ceramic, a quartz, a silicon, a metal, a polymer, and combinations thereof. Such sub-plates 8061 may be actuated along an axis of motion (e.g. axis of motion 14). Such sub-plates 8061 may be translated (or "displaced") to form a piecewise contact surface 806 with a freeform profile (or "shape" or "surface profile") to create a contact surface 806 with a discrete but arbitrarily addressable profile for use in creating an incision 45 and/or an incision 46 to address optical aberrations, including higher order aberrations, such as defocus, radial distortion, sphere, spherical aberration, cylinder, cylindrical aberration, astigmatism, coma, and trefoil in prescribing a figure for a lenticule to be removed from tissue 2 within a cornea 843. Such sub-plates 8061 may be configured to be nominally rectangular, as shown, but need not be and other geometries are considered within the scope of the present disclosure. A contact element 808 (not shown) may be placed on the distal surface of contact plate 804 to provide a clean and/or sterile surface for contact with tissue 2 and may be configured as a thin, conformal, peel-and-stick sterile barrier, which may also be disposable, as was described elsewhere herein. Rather than utilizing step 202 of FIG. 9 to reposition a contact plate 804, the immediate embodiment may allow for said step 202 to be modified to reconfigure contact plate to a second configuration prior to creating another incision. The number of actuators 8100 may be determined by the spatial resolution requirements of a given prescription and/or the tolerance of the surface figure.

By way of non-limiting examples, there may be an array of 10 square cross-sectional shaped actuators 8100, or there may be an array of 14 such actuators 8100, or there may be an array of 28 such actuators 8100; which when configured to be square-packed within the extent of a nominally 12 mm diameter disk-shaped contact surface yield areas of ~2.0 mm$^2$, ~1.44 mm$^2$, and ~0.80 mm$^2$ per actuator 8100, respectively. Alternately, a more regular array may be used, such as a 4×4 square array to yield 16 actuators 8100. When said regular array of 16 square cross-sectional shaped actuators 8100 is positioned concentric with a nominally 12 mm disk-shaped contact surface, the area per actuator may be ~9 mm$^2$, although the corners of the array may lie outside of the 12 mm disk boundary. Similarly, a 10×10 square array may yield an area per actuator of ~1.44 mm$^2$ Alternately, a customized contact plate 804 and/or contact surface 806 may be fabricated to comprise a surface profile for use in creating an incision 45 and/or an incision 46 to address higher order aberrations in prescribing a figure for a lenticule to be removed from tissue 2 within a cornea 843. Alternately, such customized contact plate 804 and/or contact surface 806 may be used individually in creating an incision 45 and/or an incision 46. Alternately, a first customized contact plate 804 and/or contact surface 806 may be used in creating an incision 45 and a second customized contact plate 804 and/or contact surface 806 may be used in creating an incision 46, wherein the first and second customized contact plates 804 and/or contact surfaces 806 may be configured with different surface profiles. Rather than utilizing step 202 of FIG. 9 to reposition a contact plate 804, the immediate embodiment may allow for said step 202 to be modified to substitute (or "interchange") second contact plate prior to creating another incision. Means of fabricating such customized contact plates 804 and/or contact surfaces 806 may selected from the group consisting of: additive manufacturing, injection molding, machining, and combinations thereof.

In some embodiments, an optical prescription may comprise one or more of surface curvatures, optical power in diopters, material properties, indices of refraction, a wavefront measurement of the eye, or thicknesses. In some embodiments, a surface figure of an optic may be defined as the perturbation of the optical surface from the optical prescription. Low-frequency errors may be typically specified as irregularity, fringes of departure, or flatness and tend to transfer light from the center of the airy disk pattern into the first few diffraction rings. This effect may reduce the magnitude of the point-spread function without widening it, thus reducing the Strehl ratio. Mid-frequency errors (or small-angle scatter) may be specified using slope or (PSD) requirements and tend to widen or smear the point spread function (PSF) and reduce contrast. Low-frequency and mid-frequency errors may both degrade the optical system performance. However, some figure imperfections may be omitted from a surface-figure specification, as may be the case for optical power and occasionally astigmatism. Optical systems may allow for individual optics to be focused, decentered, or tilted to compensate for specific aberrations. Surface accuracy and surface figure are terms often used to capture both regions. To eliminate ambiguity, one may use microns as the unit value in specifications.

Figure 12A:
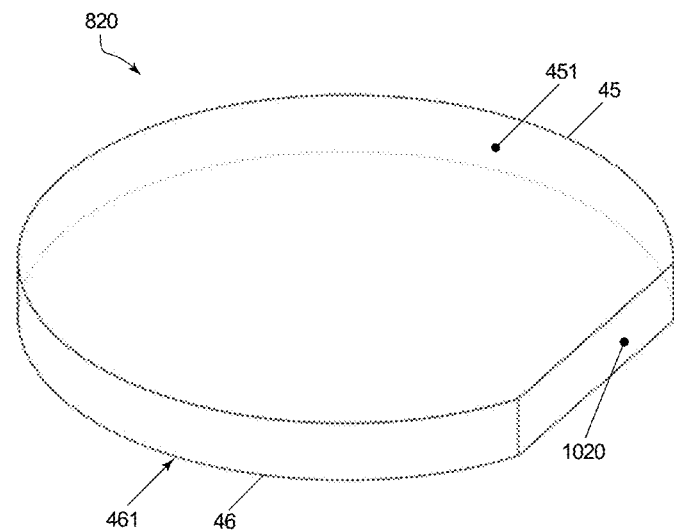
FIGS. 12A and 12B are directed at a disc-shaped lenticule, in accordance with embodiments of the present disclosure.
Figure 12B:
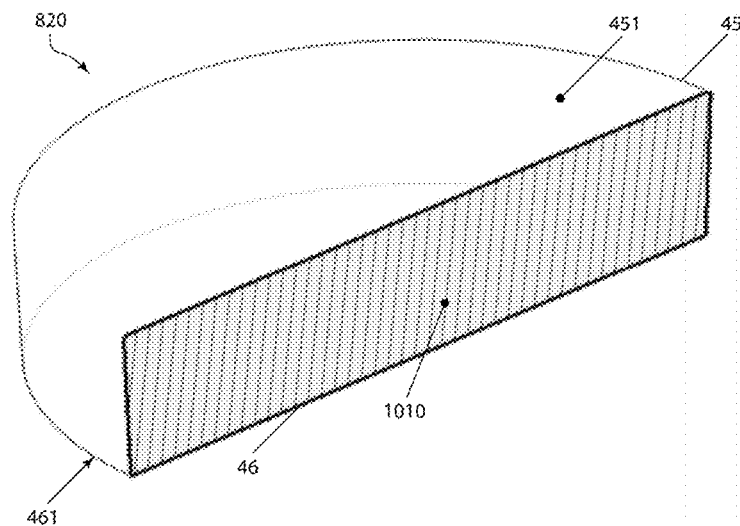

FIGS. 12A & 12B are directed at the creation of a disc-shaped lenticule. FIG. 12A shows lenticule 820, which is comprised of anterior surface 451 that may be created by incision 45 via step 114 of FIGS. 7 & 9, and posterior surface 461 that may be created by incision 46 via step 118 of FIGS. 7 & 9. Hinge 1020 may be created via step 202 of FIG. 9, the translation of contact plate to a second position between the creation of incisions 46 & 45. In the present figure the lenticule may appear to be a flat disc as shown when it is spread upon a flat surface, as shown. FIG. 12B shows a cross-sectional view of the same lenticule 820 of FIG. 12A. It the instant embodiment, a nominally planar contact plate may be positioned to first position (or "depth" or "location") to create incision 46 and then translated to a second, more anterior (or "proximal"), position in order to create incision 45. In the configuration of the instant embodiment, cross-sectional shape 1010 may be nominally rectangular and faces 451 & 461 may be nominally parallel. Alternately, incision 45 more be created at a more posterior (or "distal") position than that of incision 46 by appropriate translation of the contact plate.

Figure 13:
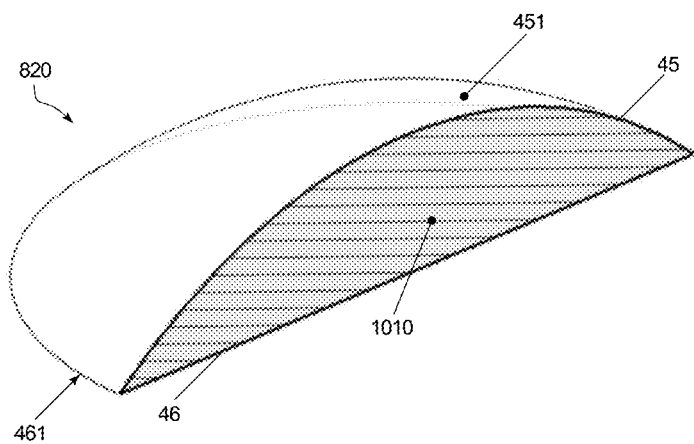
FIGS. 13 through 15 are directed at different lenticule configurations, in accordance with embodiments of the present disclosure.

FIG. 13 is directed at a plano-convex type lenticule, similar to that of FIG. 12B, in accordance with embodiments of the present disclosure. Here lenticule 820 comprises anterior face 451 that may be created by incision 45 and posterior face 461 that may be created by incision 46. The contact plate, or elements of a contact plate comprised of a plurality of translatable elements, may be configured to produce a non-planar type of surface for face 451. The configuration of the instant embodiment may be utilized to create a plano-convex type lenticule, as shown.

Figure 14:
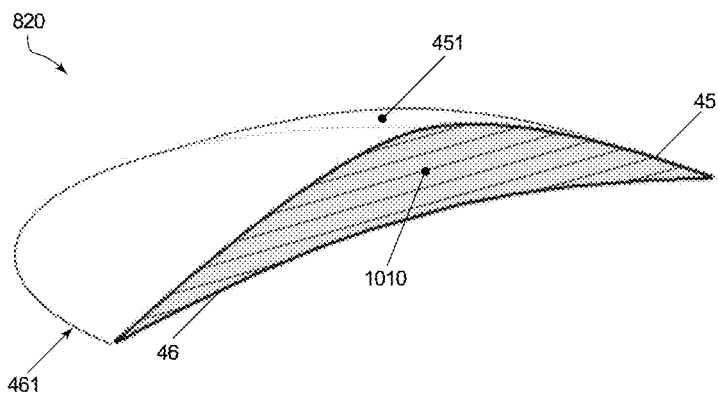

FIG. 14 is directed at a meniscus-shaped lenticule, similar to that of FIG. 13, in accordance with embodiments of the present disclosure. Here lenticule 820 comprises anterior face 451 that may be created by incision 45 and posterior face 461 that may be created by incision 46. The contact plate, or elements of a contact plate comprised of a plurality of translatable elements, may be configured to produce a non-planar type of surface for both faces 451 & 461. The configuration of the instant embodiment may be utilized to create a meniscus type lenticule, as shown.

Figure 15:
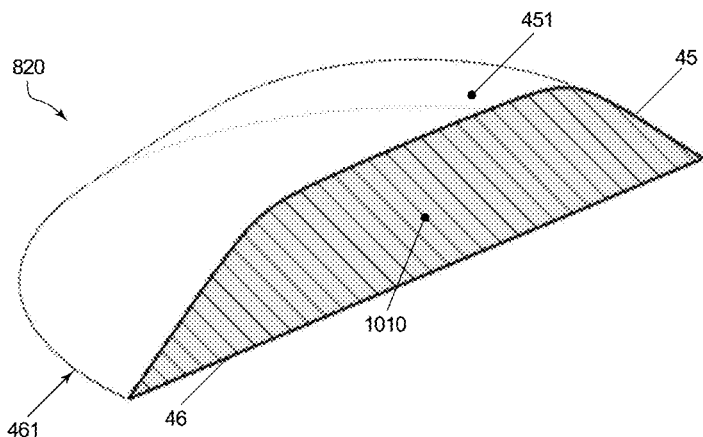

FIG. 15 is directed at a hybrid type lenticule, similar to that of FIG. 14, in accordance with embodiments of the present disclosure. Here lenticule 820 comprises anterior face 451 that may be created by incision 45 and posterior face 461 that may be created by incision 46. The contact plate, or elements of a contact plate comprised of a plurality of translatable elements, may be configured to produce a non-planar type of surface for both faces 451 & 461. The configuration of the instant embodiment may be utilized to create a meniscus type lenticule, as shown.

Figure 16A:
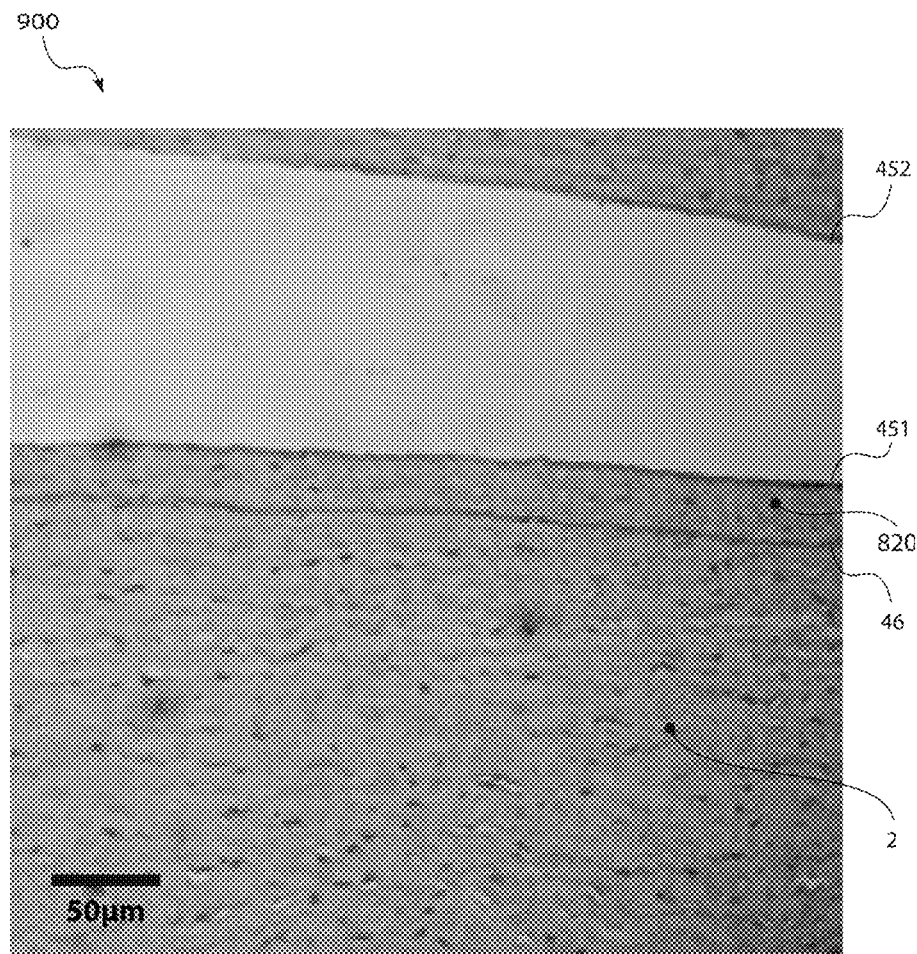
FIGS. 16A and 16B are directed at histological images of porcine corneas containing incisions made, in accordance with embodiments of the present disclosure.
Figure 16B:
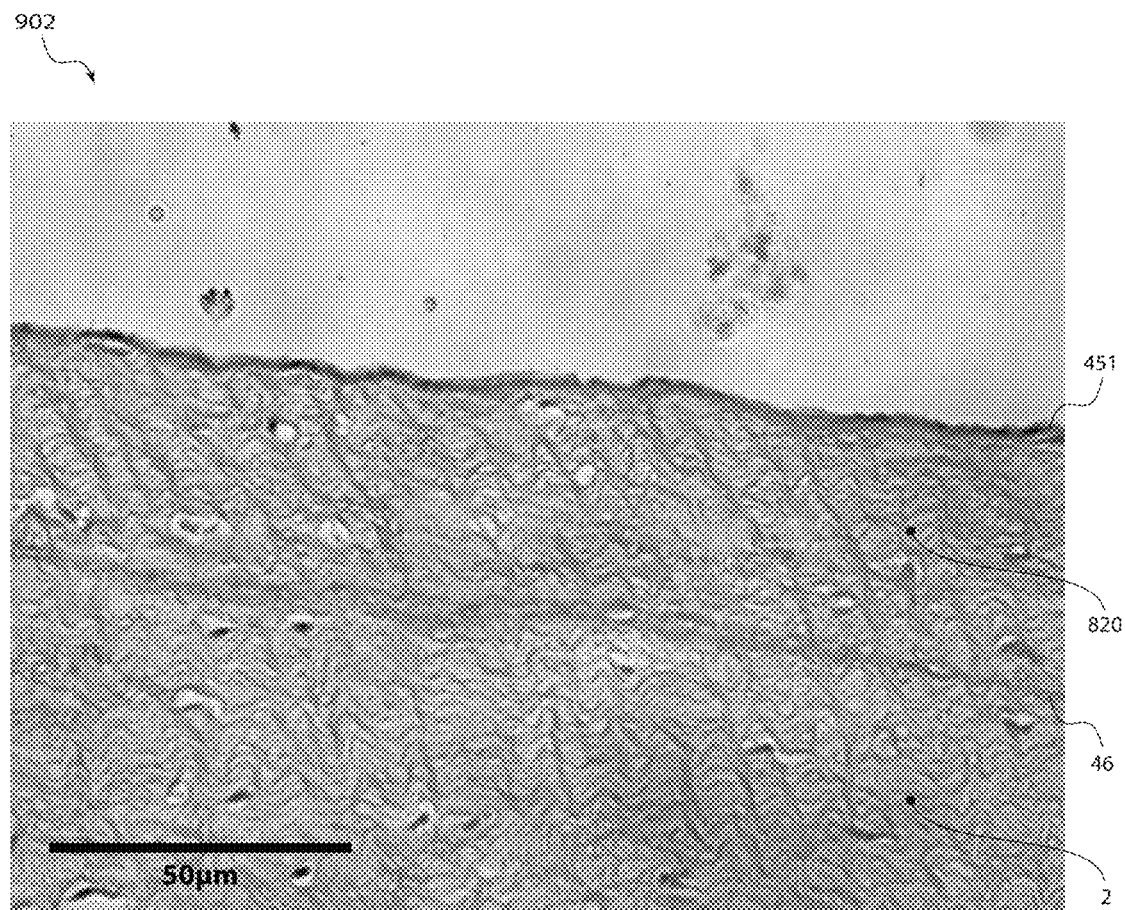

FIGS. 16A & 16B are directed at histological images of incisions in porcine cornea created in accordance with embodiments of the present disclosure. FIG. 16A shows image 900, a traditional sagittal cross-sectional (H&E stained) histological microscopic image of a porcine cornea that was incised when fresh (≤2 days post-harvest, stored at ~2° C.) and was subsequently fixed in a 4% paraformaldehyde solution. The incisional system was configured as follows: PRF~1 MHZ, V~±250V, sinusoidal waveform, $P_{rms}$~15 W; $v_{t,\ max}$~400 mm·s$^{-1}$; constant acceleration ~2000 mm·s$^{-2}$; ~Ø15 µm, L~10 mm, ~99.99% pure tungsten wire electrode; T~290 mN; ~35 µm contact plate (flat) posterior displacement between incisions 45 & 46, and a vacuum gauge pressure of ~−500 mmHg for suction element 810 as measured at vacuum sensor 854. Electrode assembly translation was accomplished using M-664.164 piezo-motor actuators from (PI, Karlsruhe, Germany). Target tissue 2 is corneal stromal tissue. Incision 45 was separated to reveal surfaces 451 and 452. Incision 46 was left intact with lenticule 820 in place. Damage may be visible as the darker bands along incisions 45 & 46 and may be on the order of ~3 µm in extent. FIG. 16B shows image 902, similar to that of FIG. 16A, but at a higher magnification and with the different spacing between incisions 45 & 46 by means of a ~50 μm posterior contact plate translation. Again, narrow damage zones are evident.

Figure 17:
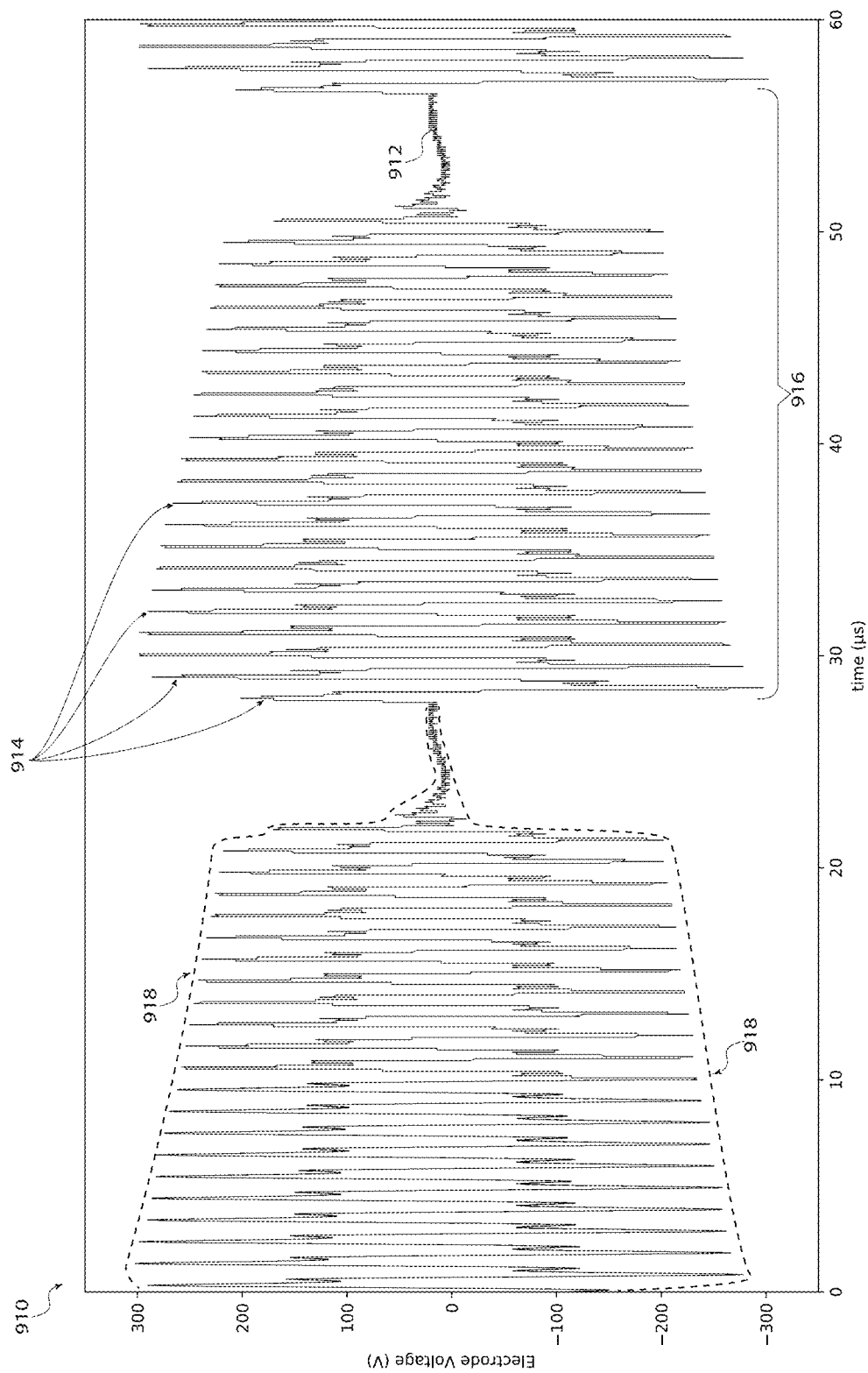
FIG. 17 is directed at a plot displaying an exemplary electrode voltage versus time, in accordance with embodiments of the present disclosure.

FIG. 17 is directed at plot 910, which displays an exemplary electrode voltage versus time waveform 912 that comprises features in accordance with embodiments of the present disclosure. Waveform 912 comprises individual cycles 914. Bursts 916 are comprised of pulses (cycles 914) and constrained by modulation envelope 918. Modulation envelope 918 may be configured to be a combination of the relationships described elsewhere herein, including pulsatile, duty cycle, and modulation (e.g., ramping) relationships. While shown here for clarity at the level of pulses and bursts, an entire incisional waveform may be similarly configured.

Figure 18:
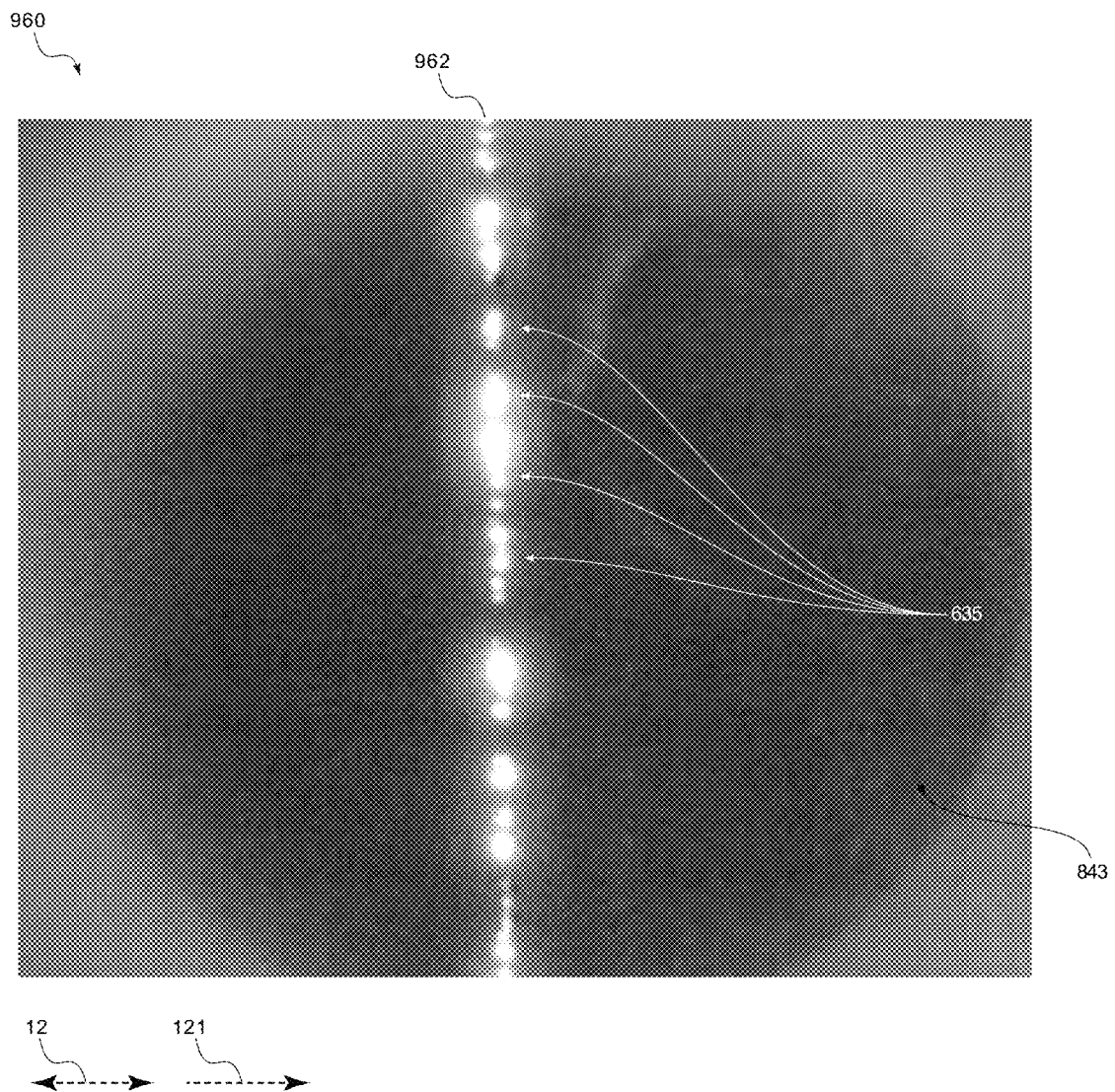
FIG. 18 is directed at a high-speed video image of a porcine cornea being incised, in accordance with embodiments of the present disclosure.

FIG. 18 is directed at image 960, a 576 pixel×464 pixel frame, as may be obtained using a high-speed digital camera such as the AOS M-VIT 4000 (AOS Technologies, Daettwil, Switzerland), when configured to operate with an equivalent sensitivity of 6400 ISO, and a shutter speed (or "integration time") of $t_{sh}$~250 μs. In the instant figure, the plurality of vapor cavities 635 along image element 962 may show the staccato disruption process, which may correspond to an electrode translation of about one diameter, as $v_t * t_{sh} \rightarrow$~13 μm and $PRF * t_{sh} \rightarrow$~250 cycles of a ~1 MHz waveform for an incisional system configured similarly to that of FIGS. 6 through 10E: $v_{t,max}$~400 mm·s$^{-1}$; constant acceleration ~2000 mm·s$^{-2}$; ~Ø13 μm, L~10 mm, ~≥99.99% pure tungsten wire electrode; T~280 mN; and a vacuum gauge pressure of ~−640 mmHg for suction element 810 as measured using a vacuum sensor 854, and nominally utilizing the waveform of FIG. 17. A plurality of vapor cavities 635 may be visible along image element 962 as an electrode 702 (located at image element 962, but otherwise obscured in the present figure) is actuated to translate along axis of motion 12 in direction 121 to create an incision within cornea 843. The plurality of vapor cavities 635 may comprise regions where light is emitted in association with the formation of plasma, and the light may comprise a wavelength that is a function of the plasma temperature and may lie within a range from about 400 nm to about 750 nm.

In accordance with embodiments of the present disclosure the technique dependency of scleral incisions may be reduced by semi-automating flap creation using a plasma-induced cutting tool which limits tissue damage and providing predictable, accurate, and precise incisions in the sclera and/or cornea, including the sclero-corneal limbus. In accordance with embodiments of the present disclosure, pockets in the sclera and/or cornea, including the sclero-corneal limbus may be made rather than the flaps traditionally used. Further embodiments may provide for incising other tissues, such as those listed in FIG. 1A. By way of non-limiting example, a plasma-induced incision may be created in a CAPSULE to produce a capsulorrhexis; in a LENS to produce lens fragments or to simplify lens fragmentation and/or lens removal; in a RETINA to produce a pocket or flap, in a TM to improve drainage and/or to lower IOP; and in an IRIS to produce an iridotomy.

A flap may be described as an incision yielding a "flap" of tissue that maybe lifted and pivot on a "hinge" to provide access to the tissue beneath it. By way of nonlimiting example, cutting three sides of a square to the 50% depth and razing a plane at that 50% depth beneath the edges of the square of a tissue may yield a half-thickness flap with the fourth uncut side of the square as its hinge. A flap may be amputated by completing the fourth side of the exemplary square incision.

A pocket maybe described as an incision that separates a first depth (or layer) of tissue from a second depth (or layer) of tissue without necessarily creating a flap. By way of a further nonlimiting example, cutting one side of a square to the 50% depth and razing a plane at that 50% depth beneath the edges of the square of a tissue may yield a half-thickness pocket.

A semi-automated cutting tool may be used to yield an incision improved over those of traditional sharp-edged instruments. A plasma-induced, semi-automated cutting tool may be used to yield an incision improved over those of a semi-automated cutting tool configured for use with traditional sharp-edged instruments.

A semi-automated cutting system with at least one degree of motion may be used to create the 5×5 mm and 4×4 mm flaps instead of manually creating them. For example, a system comprising both 5 mm wide and 4 mm wide "blades" may be used to create the 5×5 mm and 4×4 mm flaps, respectively. An electrode may comprise a wire and/or a blade.

Figure 19A:
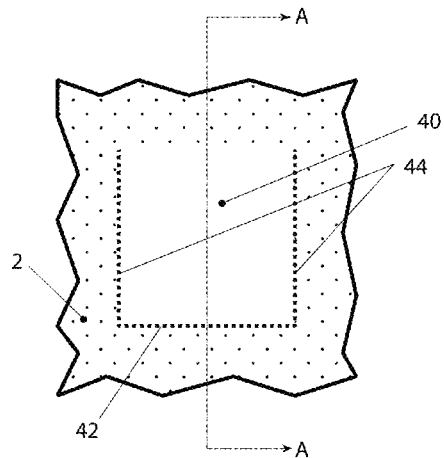
FIGS. 19A-19D depict aspects of a tissue "flap" and aspects of a tissue "pocket", in accordance with embodiments of the present disclosure.
Figure 19B:
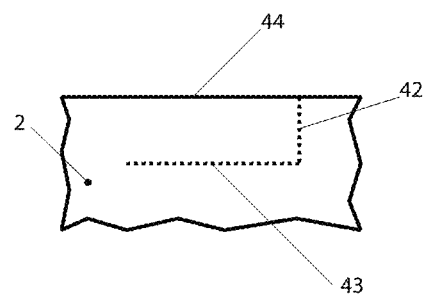

FIG. 19A shows flap 40 in tissue 2 as seen from above, and FIG. 19B shows the same flap 40 as seen looking into cross-section A-A. Flap 40 is constructed of incisions 42 and 44, which create bed 43 and form 3 sides of a square (in the examples of FIGS. 19A-19D, although other such shapes are also considered within the scope of the present disclosure). The flap may be lifted and hinge about the missing side of the square to expose the tissue beneath. Bed 43 may be planar or curved. A flap may be amputated by completing the fourth side of the exemplary square incision.

Figure 19C:
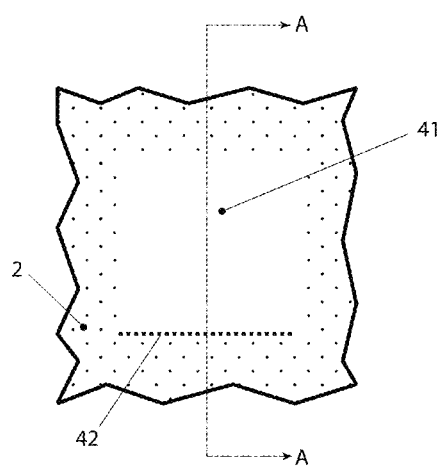
Figure 19D:
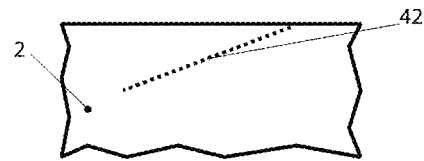

Similar to the configuration of FIGS. 19A & 19B, FIG. 19C shows pocket 41 in tissue 2 as seen from above, and FIG. 19D shows the same pocket 41 as seen looking into cross-section A-A. However, in this configuration, pocket 41 is comprised of incision 42, which creates bed 43, but lacks incisions 44. Again, bed 43 may be planar or curved, but this time will be dependent upon the longitudinal shape (or "profile") of the incisor in order to avoid creating incisions 44.

Figure 20:
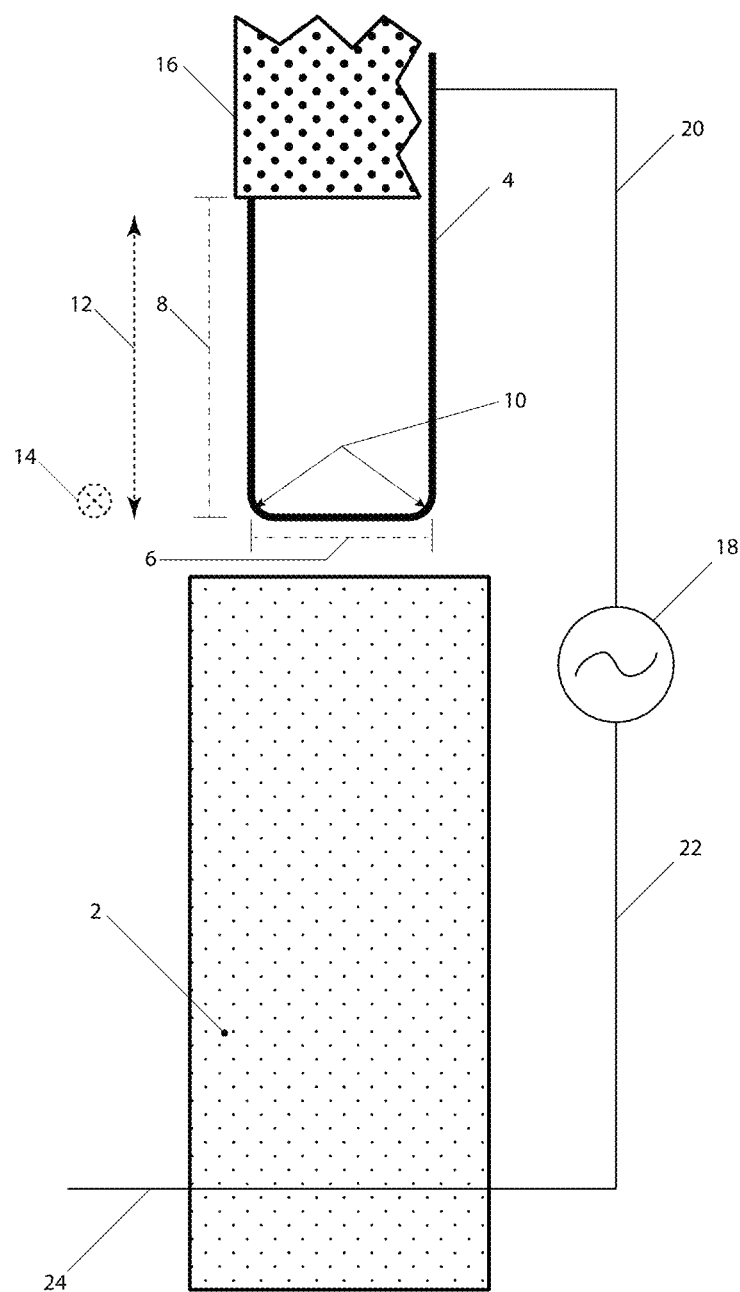
FIG. 20 depicts aspects of a system that is configured to create a tissue flap or a tissue pocket, in accordance with embodiments of the present disclosure.

FIG. 20 is directed at a system in accordance with embodiments of the present disclosure configured to create a rectangular flap or pocket as may be useful in canaloplasty for the reduction of IOP in the treatment of glaucoma. Tissue 2 may be incised using electrode 4, which is configured in a U-shape of width 6 and length 8 and comprises bends 10 in this exemplary embodiment. Electrode 4 may be connected to power RF driver 18 via lead 20. Lead 22 may be connected to the patient creating electrode 24, which in turn may be a part of a return path. RF driver may produce bipolar pulses. Electrode 4 may be enclosed within a sheath 16, shown here as partially cut-away for clarity. Direction of motion 12 may be used to provide a lateral extent to the incision and direction of motion 14 may be orthogonal to direction of motion 12 and perpendicular to the plane described by the width 6 of U-shape of electrode 4, such as may be used to create a tissue flap and/or pocket. Alternately, direction of motion 14 maybe employed to create an incision nominally perpendicular to a surface of tissue 2. Width 6 may be chosen to be between 1 mm and 10 mm, specifically 4 mm or 5 mm, as described above. Length 8 may be greater than width 6 and made to traverse tissue a distance less than length 8. For example, a 4 mm×4 mm flap may be created by configuring width 6 to be 4 mm and length 8 to be greater than 4 mm but made to traverse 4 mm of tissue along direction of motion 12.

Figure 21:
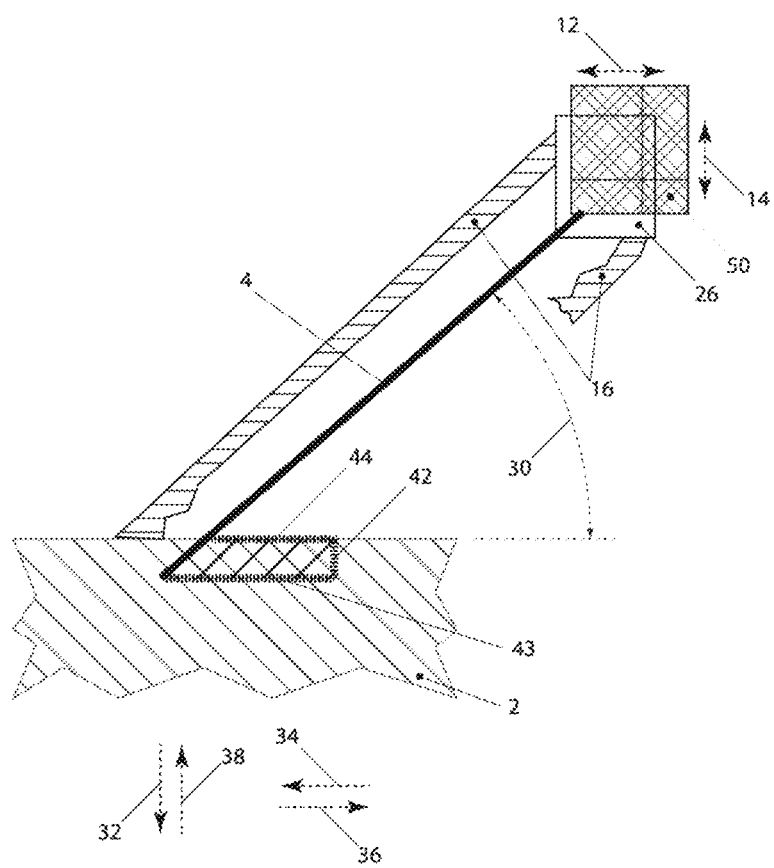
FIG. 21 depicts aspects of a system, in accordance with embodiments of the present disclosure.

FIG. 21 is directed at a system similar to that of FIG. 20, as seen from the side and configured to create a flap; with the additions of probe body 26 to contain electrode 4, sheath 16, and actuator 50; as well being oriented at angle 30 relative the surface of tissue 2. Actuator 50 may be operatively coupled to electrode 4 and move in directions of motion 12&14 such that electrode 4 is made to translate within tissue 2 along a motion profile described by moving first in direction 32; then direction 34; then direction 36, which is in opposite direction from direction 34; then direction 38, which is in opposite direction from direction 32. This configuration may then create a flap 40 (not explicitly shown for purposes of clarity) by creating incision 42, then incision 44 and bed 43. Actuator 50 may be powered, such as a motor or voice coil, by way of non-limiting examples. Alternately, actuator 50 may comprise a series of springs and ratchets or stop and triggers to create the motion profile described. Elements electrode 4 and/or sheath 6 and/or probe body 26 may be configured to be a subsystem that engages with actuator 50 and RF driver 18 and to be disposed of after use. In an alternate embodiment, a flap may be amputated by altering the motion profile as follows: by moving first in direction 32; then direction 34; then direction 38, which is in opposite direction from direction 32.

Alternately, the system of FIG. 21 may be configured such that actuator 50 translates electrode 4 first in a direction that is nominally along angle 30 then retract electrode 4 along a second direction that is nominally the opposite of the first direction in order to create a pocket rather than a flap.

Alternately, a second electrode may also be used to create a second flap or pocket that of different size and/or shape than a first flap or pocket. For example, a 5 mm×5 mm flap may be first made first and subsequently and 4 mm×4 mm flap may then be made. The exemplary 4 mm×4 mm flap may further be an amputated flap.

Figure 22A:
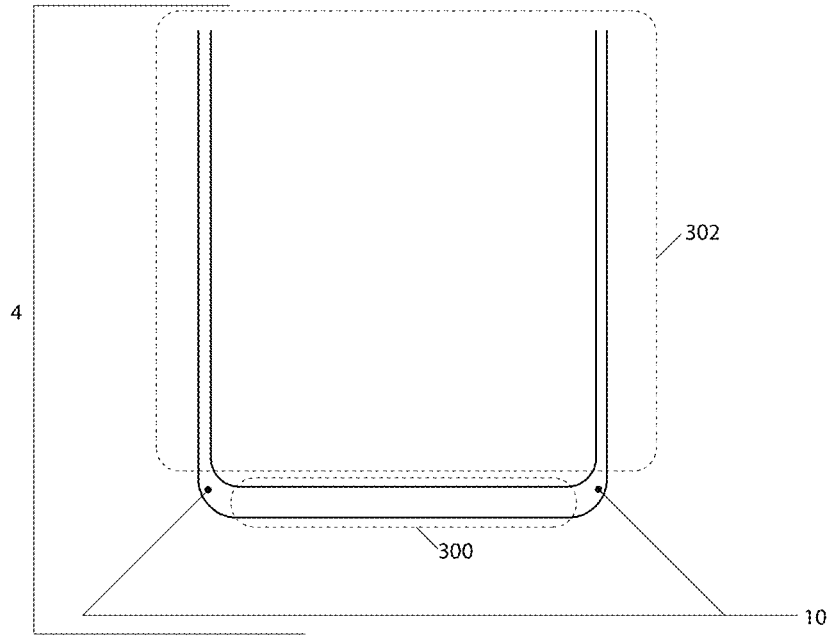
FIGS. 22A to 22C depict an electrode, in accordance with embodiments of the present disclosure.
Figure 22B:
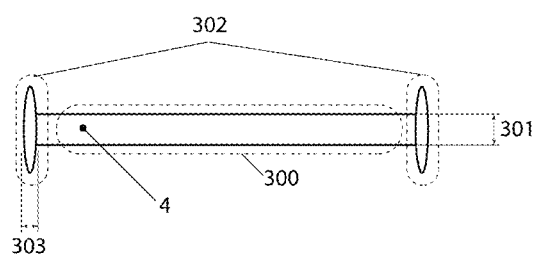
Figure 22C:
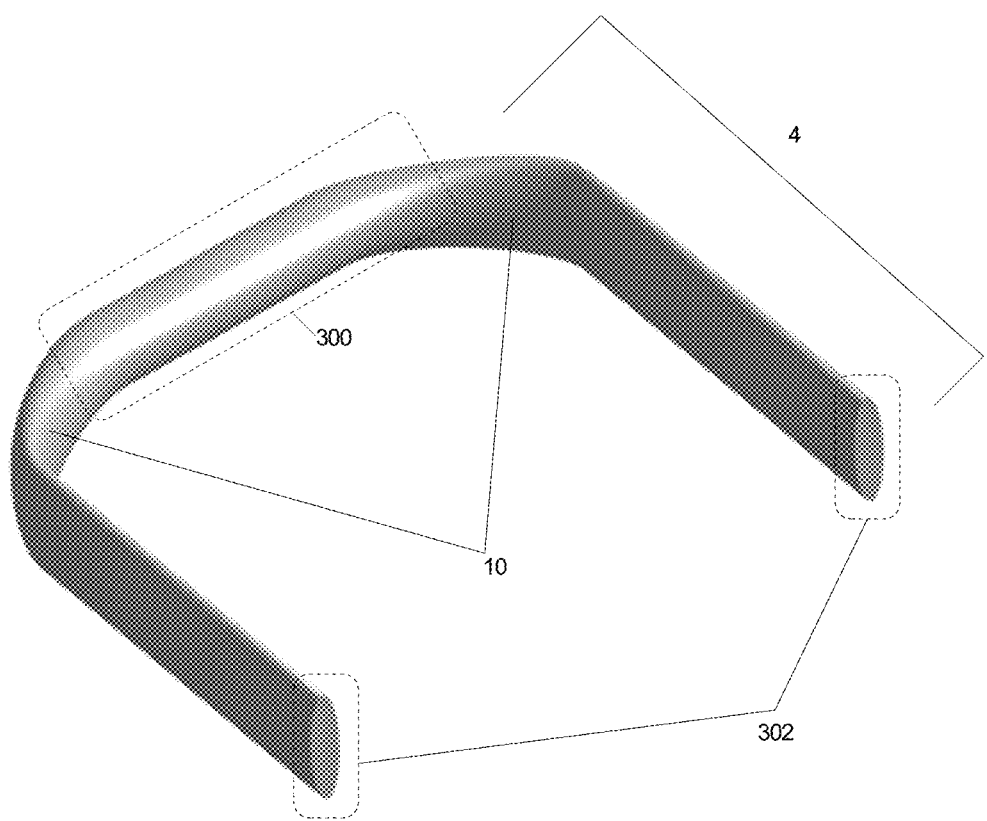

FIGS. 22A-22C are directed at details of an electrode configured in accordance with embodiments of the present disclosure, wherein electrode 4 comprises regions 300, 302, and bends 10. Nominally, the surface area may be kept constant along electrode 4. By way of non-limiting example, electrode 4 may comprise a solid wire of diameter between ~50 μm and ~300 μm and be composed of a material selected from the group consisting of; tungsten, nitinol, steel, copper, stainless steel, beryllium-copper alloy, cupronickel alloy, and aluminum. Furthermore, in alternate embodiments, an electrode may be at least partially coated with another conducting material, such as gold. Region 302 may comprise the same base structure as region 300 with the modification of being compressed in the direction parallel to the plane of the image and elongated in an orthogonal direction. Such a configuration may maintain the surface area while providing increased strength in the aforementioned orthogonal direction for improved reliability and strength while incising tissue by reducing dimension 303 to be less than dimension 301. Bends 10 may be made from either the configuration of region 300, that of region 302, or be made to transition between regions 300 & 302. Alternately, regions 300 and 302 and/or bends 10 may be joined from disparate materials. In a further alternate embodiment, electrode 4 may be constructed from tungsten wire with a diameter of ~250 μm, which has been compressed everywhere except region 300 of length ~3 mm and with a dimension 301 that is nominally the same as the ~250 μm native diameter of the wire, and to the native bends 10 located about the region 300 and made to have radii of ~0.5 mm to yield a width 6 of ~4 mm while dimension 303 is configured to be formed by the aforementioned compression and to ~400 μm.

For purposes of clarity, electrode 4 has been shown thus far as being U-shaped but it need not be. Rf driver 18 may provide an alternating current to electrode 4. Such an alternating current may be, by way of non-limiting examples; a sinewave, a square wave, a sawtooth wave, a triangle wave, or a combination thereof. The signal provided by rf driver 18 may be configured to have a base (or "carrier") frequency between ~10 kHz and ~10 MHZ and it may be further modulated to comprise bursts of pulses at frequency of between ~100 Hz and ~3 MHz to create a duty cycle. The duty cycle may be between ~0.01% and ~100%. In alternate embodiments, the duty cycle may be between ~60% and ~80%. The peak-to-peak voltage provided by rf driver 18 may be between ~500V and ~2000V. In alternate embodiments, the peak-to-peak voltage provided by rf driver 18 may be between ~400V and ~800V. In one embodiment the signal of rf driver 18 may be configured to have a peak-to-peak bipolar voltage of ~800V (comprising both ~+400V and ~−400V amplitudes) with a carrier frequency of ~1 MHz and a modulation frequency of ~10 kHz, such as may be useful when electrode 4 is comprised of a ~Ø100 μm diameter tungsten wire in region 300.

Figure 23:
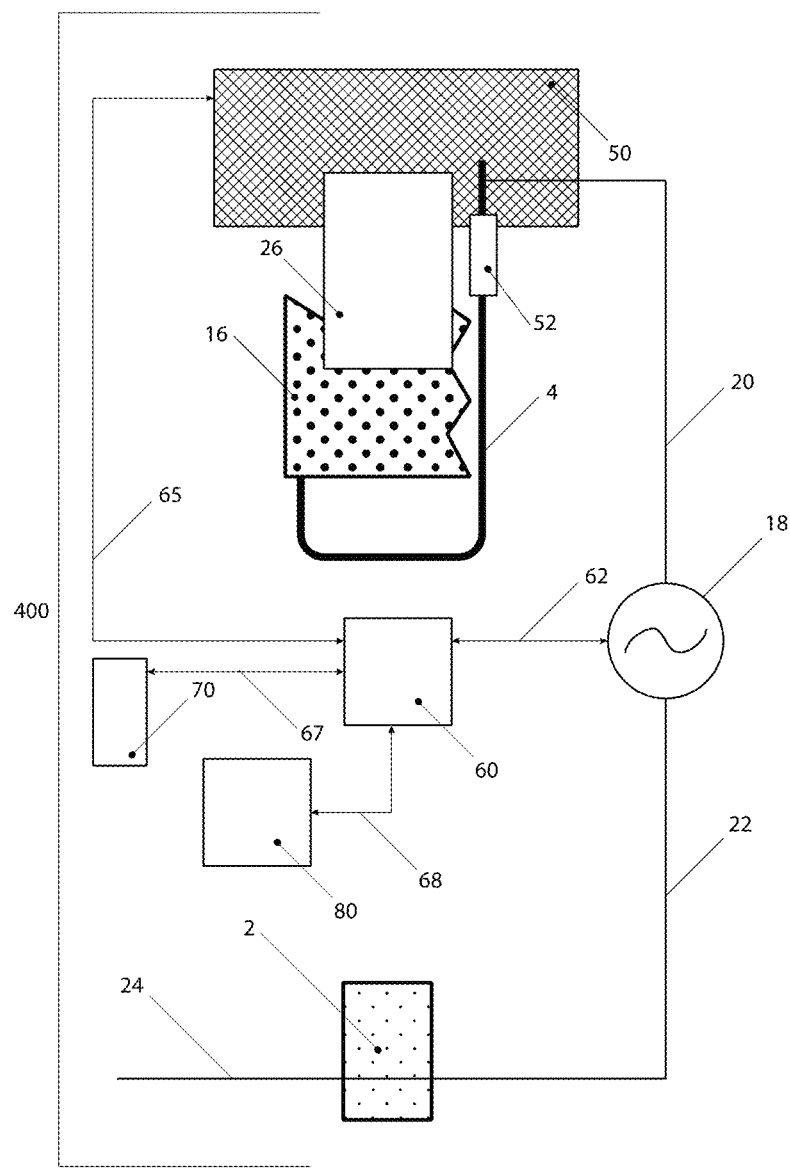
FIG. 23 depicts a system, in accordance with embodiments of the present disclosure.

FIG. 23 is directed at system 400, which is configured in accordance with embodiments of the present disclosure. In addition to the elements related to previous figures, system 400 further comprises controller 60, power supply 70, user interface 80, and coupler 52. Connection 62 connects controller 60 with RF driver 18 and is at least a unidirectional connection. Connection 62 may also be a bidirectional connection wherein controller 60 is able to sense and/or respond to at least a signal from rf driver 18. Such a signal may be a safety signal related to a sensed voltage or current. In a further alternate embodiment, rf driver 18 may provide feedback to controller 60 or use such feedback internally and may share such feedback as signals with controller 60. Such feedback may be, for example, EMF or current feedback and may be useful in determining when electrode 4 contacts tissue and/or the status of the plasma. Such status may be, for example, whether or not the plasma in the glow discharge regime or not. Likewise, connection 65 connects controller 60 with actuator 50 and is at least a unidirectional connection. Actuator 50 may be comprised of at least one electrical motor and may further comprise a positional encoder. Connection 65 may alternately be a bidirectional connection wherein signals are shared between controller 60 and actuator 50, such as position, velocity, acceleration, out of bounds errors, etc. In a further alternate embodiment, actuator 50 may provide feedback to controller 60 or use such feedback internally and may share such feedback as signals with controller 60. Such feedback may be, for example, force feedback and may be useful in determining when electrode 4 contacts tissue or when it imparts excessive force on the tissue to be incised. Likewise, connection 67 connects controller 60 with power supply 70 and is at least a unidirectional connection. In a further alternate embodiment, power supply 70 may provide feedback to controller 60 or use such feedback internally and may share such feedback as signals with controller 60. Such feedback may be, for example, an error signal. Such error signals may be temperature errors, input voltage errors, output voltage errors, input current errors, output current errors, etc. Likewise, connection 68 connects controller 60 with user interface 80 and is at least a unidirectional connection. In a further alternate embodiment, interface 80 may provide feedback to controller 60 or use such feedback internally and may share such feedback as signals with controller 60. For example, user interface 80 may be a graphical user interface or a button used to signal actuator 50 to move electrode 4 and incise tissue. This exemplary embodiment of system 400 also includes coupler 52, which may couple electrode 4 to actuator 50 such that electrode 4 may be moved, as described with respect to earlier figures. Coupler 52 may be constructed from an electrically insulating material and be configured to electrically isolate electrode 4 from at least one other element of system 400. Coupler 52, and/or sheath 16, as well as electrode 4 may be joined into a subsystem that may be disposed of after use. Although not shown, an alternate embodiment is a configuration for coupler 52 that may be made to connect both sides of the (exemplary) U-shaped electrode 4 to actuator 50. Electrode 4 may be translated by actuator 50 at a rate of $\sim 200$ mm·s$^{-1}$.

The symbol "$\sim$" is used herein as equivalent to "about". For example, a statement such as "$\sim 100$ ms" is equivalent to a statement of "about 100 ms" and a statement such as "$v_t = \sim 5$ mm·s$^{-1}$" is equivalent to a statement of "$v_t$ is about 5 mm·s$^{-1}$".

The symbol "Ø" is used herein to indicate the following value is a diameter. For example, a statement such as "Ø10 μm" is equivalent to a statement of "a diameter of 10 μm." Furthermore, a statement such as "$\sim$Ø12 μm" is equivalent to a statement of "a diameter of about 12 μm."

The symbol "$\propto$" is used herein to indicate proportionality. For example, a statement such as "$\propto r^{-2}$" is equivalent to the statement "proportional to $r^{-2}$."

Dot notation is used herein to represent compound units for the sake of clarity and brevity. For example, the statement k=$\sim$40N·m$^{-1}$ is equivalent to the statement "k=$\sim$40 N per meter."

As used herein "mN" refers to "milli Newtons", which is $10^{-3}$ Newtons.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection.

Unless otherwise noted, the terms "operatively connected to" and "operatively coupled to" (and their derivatives), as used in the specification and claims, are to be construed as permitting both direct and indirect (i.e., via other elements or components) connection to perform a function.

In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. A system for incising tissue with a plasma, comprising: an elongate electrode, the elongate electrode configured to flex and generate the plasma to incise the tissue; an electrical energy source operatively coupled to the elongate electrode and configured to provide electrical energy to the electrode to generate the plasma; and a tensioning element operatively coupled to the elongate electrode, the tensioning element configured to provide tension to the elongate electrode to allow the elongate electrode to flex in response to the elongate electrode engaging the tissue and generating the plasma.

Clause 2. The system of clause 1, further comprising a plurality of arms operatively coupled to the electrode and the tensioning element.

Clause 3. The system of clause 2, wherein the electrode is unsupported between the two arms.

Clause 4. The system of clause 2, wherein the electrode is configured to vibrate transversely to an elongate axis of the electrode.

Clause 5. The system of clause 2, further comprising a support structure operatively coupled to the plurality of arms and the tensioning element, wherein the support structure is configured to advance the plurality of arms and the tensioning element in order to advance the elongate electrode into tissue to incise the tissue.

Clause 6. The system of clause 5 wherein an incisional portion of the elongate electrode is suspended between the plurality of arms with tension from the tensioning element and wherein a gap extends between the plurality of arms.

Clause 7. The system of clause 6 wherein the gap extends between the incisional portion of the elongate electrode, the plurality of arms and the support structure.

Clause 8. The system of clause 6 wherein the gap is sized to receive incised tissue along an incision formed with the elongate electrode.

Clause 9. The system of clause 5 wherein the support structure is operatively coupled to one or more actuators to move the elongate electrode in one or more directions.

Clause 10. The system of clause 9 wherein the one or more actuators is configured to move the electrode with a variable velocity.

Clause 11. The system of clause 1, wherein the tensioning element is selected from the group consisting of a spring, a coil spring, a leaf spring, a torsion spring, a mesh, a hinge, and a living hinge.

Clause 12. The system of clause 1, wherein the elongate electrode comprises a first portion of an elongate filament and wherein the tensioning element comprises a second portion of the elongate filament shaped to tension the elongate electrode.

Clause 13. The system of clause 1, further comprising an electrode assembly, the electrode assembly comprising a support structure operatively coupled to a plurality of arms and the tensioning element, wherein the electrode assembly is configured to advance the electrode into tissue to incise the tissue.

Clause 14. The system of clause 1, wherein the electrode is configured to sequentially contact a plurality of locations of the tissue to generate the incision.

Clause 15. The system of clause 14, wherein the plurality of locations comprises a plurality of discontiguous locations.

Clause 16. The system of clause 15, wherein the electrode is configured to vaporize tissue in contact with the electrode at each of the plurality of discontiguous locations.

Clause 17. The system of clause 1, wherein the electrode is configured to generate a plurality of flashes of light energy at a plurality of locations while the electrode incises the tissue.

Clause 18. The system of clause 17, wherein the plurality of flashes of light energy comprise visible light energy comprising a wavelength within a range from about 400 nm to about 750 nm.

Clause 19. The system of clause 17, wherein each of the plurality of flashes of light energy comprises maximum distance across of no more than about 1 mm.

Clause 20. The system of clause 17, wherein the plurality of flashes is generated within a time interval of no more than about 250 µs and optionally no more than about 25 µs.

Clause 21. The system of clause 17, wherein the plurality of flashes is generated with an electrode movement distance of no more than about 100 µm and optionally no more than about 10 µm.

Clause 22. The system of clause 17, wherein the plurality of flashes of light is distributed at a plurality of non-overlapping regions.

Clause 23. The system of clause 22, wherein the plurality of non-overlapping regions is located along the elongate electrode.

Clause 24. The system of clause 17, wherein the plurality of flashes of light are generated at a first rate with a first velocity of the electrode and a second rate with a second velocity of the electrode, wherein the first rate is greater than the second rate when the first velocity is less than the second velocity and wherein the first rate is less than the second rate when the first velocity is greater than the second velocity.

Clause 25. The system of clause 24, wherein the plurality of flashes of light is generated at a substantially constant rate to within about 25% and wherein one or more of a pulse rate or a burst rate of a waveform to the elongate electrode is varied in response to the a varying velocity of the electrode to maintain the substantially constant rate.

Clause 26. The system of clause 1, wherein the elongate electrode comprises a filament and wherein the filament comprises one or more of a wire or a thread.

Clause 27. The system of clause 1, wherein the elongate electrode comprises a wire.

Clause 28. The system of clause 27, wherein a diameter of the wire is within a range from 5 µm to 200 µm, optionally from about 5 µm to about 100 µm, optionally from about 5 µm to about 50 µm, optionally from about 5 µm to about 25 µm, or optionally from about 5 µm to about 20 µm.

Clause 29. The system of clause 1, wherein the elongate electrode comprises a cross-sectional distance and wherein the cross-sectional distance comprises no more than about 25 µm.

Clause 30. The system of clause 1, wherein the elongate electrode operatively coupled to the tensioning element comprises a mechanical resonance frequency within a range from about 1 kHz to about 100 kHz and optionally within a range from about 2 kHz to about 50 KHz.

Clause 31. The system of clause 1, wherein the tensioning element is configured to tension the elongate electrode with a force within a range from about 20 mN to about 2N and optionally within a range from about 50 mN to about 1N and further optionally within a range from about 100 mN to about 500 mN.

Clause 32. The system of clause 1, wherein the elongate electrode comprises a mass per unit length within a range from about 0.2 µg·mm-1 to about 3 µg·mm-1.

Clause 33. The system of clause 1, wherein elongate electrode comprises a material selected from the group consisting of tungsten, nitinol, steel, copper, brass, titanium, stainless steel, beryllium-copper alloy, cupronickel alloy, palladium, platinum, platinum-iridium, silver, and aluminum.

Clause 34. The system of clause 1, wherein elongate electrode comprises an axis along an elongate direction of the electrode and wherein the electrode is configured to incise tissue with movement in a direction transverse to the axis.

Clause 35. The system of clause 1, wherein elongate electrode is configured to incise tissue in a direction transverse to an elongate direction of the electrode at a velocity greater than about 1 m·s-1.

Clause 36. The system of clause 1, wherein elongate electrode is configured to incise tissue in a direction transverse to an elongate direction of the electrode at a velocity within a range from about 0.5 cm·s-1 to about 10 m·s-1 and optionally within a range from about 1 cm·s-1 to about 5 m·s-1.

Clause 37. The system of clause 1, wherein the electrode is configured to incise an area of tissue at a rate within a range from about 5 mm$^2$·s-1 to about 50,000 mm$^2$·s-1 and optionally within a range from about 500 mm$^2$·s-1 to about 25,000 mm$^2$·s-1.

Clause 38. The system of clause 1, wherein the electrical energy source is configured to deliver a waveform, wherein the waveform comprises one or more of a pulsatile waveform, a sinusoidal waveform, a square waveform, a sawtooth waveform, a triangular waveform, a fixed frequency waveform, a variable frequency waveform, or a gated waveform.

Clause 39. The system of clause 38, wherein the waveform comprises the sinusoidal waveform and wherein the sinusoidal waveform comprises a frequency within a range from about 0.5 MHz to about 2 MHz.

Clause 40. The system of clause 38, wherein the waveform comprises a combination of the sinusoidal waveform and the gated waveform and wherein the sinusoidal waveform comprises a frequency within a range from about 0.5 MHz to about 2 MHz and wherein the gated waveform comprises a gate frequency within a range from about 20 kHz to about 80 kHz and a duty cycle within a range from about 35% to about 100%.

Clause 41. The system of clause 1, further comprising a controller operatively coupled to the electrical energy source.

Clause 42. The system of clause 41, wherein the controller is configured to control parameters of the electrical energy source by modulating the waveform using a parameter selected from the group consisting of a voltage, a current, a carrier frequency, a modulation frequency, a duty cycle, a power setpoint, a power limit, an energy per pulse setpoint, an energy per pulse limit, and a modulation envelope.

Clause 43. The system of clause 42, wherein the waveform comprises a pulsatile voltage waveform comprising pulses and a substantially constant frequency within a range from about 10 kHz to about 10 MHz and optionally within a range from about 0.5 MHz to about 2 MHz.

Clause 44. The system of clause 43, wherein the waveform provides an energy per pulse of within a range from about 0.5 µJ to about 50 µJ and optionally within a range from about 1 µJ to about 10 µJ.

Clause 45. The system of clause 44, wherein the controller is configured to modulate the substantially constant frequency waveform to produce bursts.

Clause 46. The system of clause 45, wherein a frequency of the bursts is within a range from about 100 Hz and about 3 MHz and optionally within a range from about 1 kHz to about 100 kHz.

Clause 47. The system of clause 46, wherein the waveform from the electrical energy source is configured to supply an average power within a range from about 1 W to about 25 W.

Clause 48. The system of clause 5, further comprising a translation element operatively coupled to the support structure and configured to direct the support structure along an axis of motion transverse to an elongate axis of the electrode.

Clause 49. The system of clause 48, wherein the translation element is selected from the group consisting of a translation stage, a linear stage, a rotary stage, a rail, a rod, a cylindrical sleeve, a screw, a roller screw, a travelling nut, a rack, a pinion, a belt, a chain, a linear motion bearing, a rotary motion bearing, a cam, a flexure, and a dovetail.

Clause 50. The system of clause 49, comprising an actuator operatively coupled to the translation element to move the support structure along an axis of motion.

Clause 51. The system of clause 50, wherein the translation element is manually actuated.

Clause 52. The system of clause 50, wherein the actuator is selected from the group consisting of a motor, a rotary motor, a squiggle motor, a linear motor, a solenoid, a rotary solenoid, a linear solenoid, a voice coil, a spring, a moving coil, a piezoelectric actuator, a pneumatic actuator, a hydraulic actuator, and a fluidic actuator.

Clause 53. The system of clause 5, wherein a portion of the support structure comprises a material selected from the group consisting of tungsten, nitinol, steel, copper, brass, titanium, stainless steel, beryllium-copper alloy, cupronickel alloy, palladium, platinum, platinum-iridium, silver, aluminum, polyimide, PTFE, polyethylene, polypropylene, polycarbonate, poly(methyl methacrylate), acrylonitrile butadiene styrene, polyamide, polylactide, polyoxymethylene, polyether ether ketone, polyvinyl chloride, polylactic acid, glass, and ceramic.

Clause 54. The system of clause 48, wherein the translation element comprises a first translation element having a first axis of motion and a second translation element having a second axis of motion different from the first axis of motion.

Clause 55. The system of clause 54, wherein the first and second translation elements are each selected from the group consisting of a translation stage, a linear stage, a rotary stage, a rail, a rod, a cylindrical sleeve, a screw, a roller screw, a travelling nut, a rack, a pinion, a belt, a chain, a linear motion bearing, a rotary motion bearing, a cam, a flexure, and a dovetail.

Clause 56. The system of clause 55, further comprising a contact plate operatively coupled to the second translation element to engage a portion of the tissue to shape the tissue prior to incising the tissue with the electrode.

Clause 57. The system of clause 1, further comprising a contact plate operatively coupled to the elongate electrode, the contact plate configured to engage a portion of a cornea to shape the cornea prior to incising the cornea with the electrode.

Clause 58. The system of clause 57, wherein the contact plate comprise a first contact plate have a first surface profile and a second contact plate having a second surface profile, a difference between the first surface profile and the second surface profile corresponding to a refractive correction of an eye to correct the refractive error of the eye.

Clause 59. The system of clause 57, wherein the contact plate comprises a free-form optical surface shaped to correct wavefront aberrations an eye.

Clause 60. The system of clause 57, wherein the contact plate comprises a plurality of independently adjustable actuators to shape the cornea.

Clause 61. The system of clause 60, wherein the contact plate comprises a plurality of plates operatively coupled to the independently adjustable actuators to shape the cornea.

Clause 62. The system of clause 61, wherein each of the plurality of plates is configured to be driven to a first position and a second position at each of a plurality of locations, a difference between the first position and the second position corresponding to a shape profile of tissue to be resected from the cornea to ameliorate refractive error of the eye.

Clause 63. The system of clause 62, wherein the plurality of locations comprises a plurality of two-dimensional locations and the shape profile comprises a three-dimensional tissue resection profile.

Clause 64. The system of clause 60, wherein the plurality of actuators comprises at least 10 actuators and optionally wherein the plurality of actuators comprises at least 16 actuators and optionally wherein the plurality of actuators comprises at least 42 actuators and optionally wherein the plurality of actuators comprises at least 100 actuators.

Clause 65. The system of clause 60, wherein the contact plate comprises a deformable membrane operatively coupled to the plurality of independently adjustable actuators.

Clause 66. The system of clause 60, wherein the contact plate comprises a first configuration for a first incision with the electrode along a first incision profile and a second configuration for a second incision with the electrode along a second incision profile and wherein a difference between the first incision profile and the second incision profile corresponds to a shape of a lenticule of tissue to be removed from the cornea to treat a refractive error of the eye.

Clause 67. The system of clause 57, wherein the contact plate is configured to correct one or more of sphere, cylinder, coma, spherical aberration, or trefoil of an eye.

Clause 68. The system of clause 57, further comprising a suction element to engage tissue retain the tissue in contact with the second translation element in a substantially fixed position while the first translation element moves the electrode to incise the tissue.

Clause 69. The system of clause 57, further comprising sterile barrier for placement on the contact plate to maintain sterility of the eye.

Clause 70. The system of clause 69, wherein the sterile barrier comprises a thin conformal barrier to conform to the shape of the contact plate with the sterile barrier between the eye and the contact plate.

Clause 71. The system of clause 69, wherein the sterile barrier comprises a peel-and-stick sterile barrier.

Clause 72. The system of clause 57, wherein: a length of the elongate electrode is within a range from about 6 mm to about 12 mm; the tissue comprises corneal tissue; the electrode comprises a wire having a diameter within a range from about 5 μm to about 20 μm; and wherein the tensioning element is configured to provide a tension to the electrode within a range from about 100 mN to about 500 mN.

Clause 73. The system of clause 1, further comprising: a processor operatively coupled to the elongate electrode, the processor configured with instructions to advance the electrode distally and draw the electrode proximally.

Clause 74. The system of clause 73, wherein: the elongate electrode is sized for insertion into the tissue; the processor is configured with instructions to incise the tissue with the electrode to define a volume of incised tissue; and wherein the volume comprises a shape profile.

Clause 75. The system of clause 74, wherein the processor is configured with instructions to move the electrode with a first movement to define a first surface on a first side of the volume of tissue and move with a second movement to define a second surface on a second side of the volume of tissue.

Clause 76. The system of clause 74, wherein the processor is configured with instructions to advance the electrode distally to define a first surface on a first side of the volume of tissue and to draw the electrode proximally to define a second surface on a second side of the volume of tissue.

Clause 77. The system of clause 76, wherein a gap extends between the elongate electrode and the support structure and wherein the gap is sized to receive tissue and wherein tissue extending into the gap is incised when the electrode is drawn proximally.

Clause 78. The system of clause 74, the contact plate comprises a first configuration to define a first surface on a first side of the volume of tissue and a second configuration to define a second surface on a second side of the volume of tissue.

Clause 79. The system of clause 74, wherein a first contact plate comprises a first shape profile to define a first surface on a first side of the volume of tissue and a second shape profile to define a second surface on a second side of the volume of tissue.

Clause 80. The system of clause 74, wherein the shape profile comprises a thickness profile.

Clause 81. A system to treat a refractive error of an eye, the system comprising: an elongate electrode to incise corneal tissue; an electrical energy source operatively coupled to the elongate electrode and configured to provide electrical energy to the electrode; a contact plate configured to engage a portion of a cornea to shape the cornea prior to incising the cornea with the electrode; and a support structure operatively coupled to the elongate electrode and the plate, the support configured to move the electrode relative to the plate and incise the corneal tissue with the electrode.

Clause 82. The system of clause 81, further comprising a translation element operatively coupled to the support structure and the elongate electrode to incise the corneal tissue with translation of the electrode.

Clause 83. The system of clause 81, wherein the contact plate comprise a first contact plate have a first surface profile and a second contact plate having a second surface profile, a difference between the first surface profile and the second surface profile corresponding to a refractive correction of an eye to correct the refractive error of the eye.

Clause 84. The system of clause 81, wherein the contact plate comprises a free-form optical surface shaped to correct wavefront aberrations an eye.

Clause 85. The system of clause 81, wherein the contact plate comprises a plurality of independently adjustable actuators to shape the cornea.

Clause 86. The system of clause 85, wherein the contact plate comprises a plurality of plates operatively coupled to the independently adjustable actuators to shape the cornea.

Clause 87. The system of clause 86, wherein each of the plurality of plates is configured to be driven to a first position and a second position at each of a plurality of locations, a difference between the first position and the second position corresponding to a shape profile of tissue to be resected from the cornea to ameliorate refractive error of the eye.

Clause 88. The system of clause 87, wherein the plurality of locations comprises a plurality of two-dimensional locations and the shape profile comprises a three-dimensional tissue resection profile.

Clause 89. The system of clause 85, wherein the plurality of actuators comprises at least 10 actuators and optionally wherein the plurality of actuators comprises at least 16 actuators and optionally wherein the plurality of actuators comprises at least 42 actuators and optionally wherein the plurality of actuators comprises at least 100 actuators.

Clause 90. The system of clause 85, wherein the contact plate comprises a deformable membrane operatively coupled to the plurality of independently adjustable actuators.

Clause 91. The system of clause 85, wherein the contact plate comprises a first configuration for a first incision with the electrode along a first incision profile and a second configuration for a second incision with the electrode along a second incision profile and wherein a difference between the first incision profile and the second incision profile corresponds to a shape of a lenticle of tissue to be removed from the cornea to treat a refractive error of the eye.

Clause 92. The system of clause 81, wherein the contact plate is configured to correct one or more of sphere, cylinder, coma, spherical aberration, or trefoil of an eye.

Clause 93. The system of clause 81, further comprising a suction element to engage tissue retain the tissue in contact with the second translation element in a substantially fixed position while the first translation element moves the electrode to incise the tissue.

Clause 94. The system of clause 81, further comprising sterile barrier for placement on the contact plate to maintain sterility of the eye.

Clause 95. The system of clause 94, wherein the sterile barrier comprises a thin conformal barrier to conform to the shape of the contact plate with the sterile barrier between the eye and the contact plate.

Clause 96. The system of clause 94, wherein the sterile barrier comprises a peel-and-stick sterile barrier.

Clause 97. The system of clause 81, wherein: a length of the elongate electrode is within a range from 6 mm to 12 mm; the electrode comprises a wire having a diameter within a range from 5 µm to 20 µm; and wherein the tensioning element is configured to provide a tension to the electrode within a range from 100 mN to 500 mN.

Clause 98. The system of clause 81, further comprising: a processor operatively coupled to the elongate electrode, the processor configured with instructions to advance the electrode distally and draw the electrode proximally.

Clause 99. The system of clause 98, wherein: the elongate electrode is sized for insertion into a cornea of the eye to treat a refractive error of the eye; the processor is configured with instructions to incise the cornea with the electrode to define a lenticle of corneal tissue within a pocket; and wherein the lenticle comprises a shape profile corresponding to treatment of the refractive error.

Clause 100. The system of clause 99, wherein the processor is configured with instructions to move the electrode with a first movement to define a first surface on a first side of the lenticle and moved with a second movement to define a second surface on a second side of the lenticle.

Clause 101. The system of clause 99, wherein the processor is configured with instructions to advance the electrode distally to define a first surface on a first side of the lenticle and to draw the electrode proximally to define a second surface on a second side of the lenticle.

Clause 102. The system of clause 101, wherein a gap extends between the elongate electrode and the support structure and wherein the gap is sized to receive tissue and wherein tissue extending into the gap is incised when the electrode is drawn proximally.

Clause 103. The system of clause 99, the contact plate comprises a first configuration to define a first surface on a first side of the lenticule and a second configuration to define a second surface on a second side of the lenticule.

Clause 104. The system of clause 99, wherein a first contact plate comprises a first shape profile to define a first surface on a first side of the lenticule and a second shape profile to define a second surface on a second side of the lenticule.

Clause 105. The system of clause 99, wherein the shape profile comprises a thickness profile.

Clause 106. A method for incising tissue with a plasma, comprising: incising tissue with an elongate electrode, the elongate electrode configured to flex and generate the plasma to incise the tissue; wherein an electrical energy source is operatively coupled to the elongate electrode and provides electrical energy to the electrode to generate the plasma; and wherein a tensioning element is operatively coupled to the elongate electrode and provides tension to the elongate electrode to allow the elongate electrode to flex in response to the elongate electrode engaging the tissue and generating the plasma.

Clause 107. The method of clause 106, wherein a plurality of arms is operatively coupled to the electrode and the tensioning element.

Clause 108. The method of clause 107, wherein the electrode is unsupported between the two arms.

Clause 109. The method of clause 107, wherein the electrode is configured to vibrate transversely to an elongate axis of the electrode.

Clause 110. The method of clause 107, wherein a support structure is operatively coupled to the plurality of arms and the tensioning element, wherein the support structure advances the plurality of arms, the tensioning element, and the elongate electrode to incise the tissue.

Clause 111. The method of clause 110, wherein an incisional portion of the elongate electrode is suspended between the plurality of arms with tension from the tensioning element and wherein a gap extends between the plurality of arms.

Clause 112. The method of clause 111, wherein the gap extends between the incisional portion of the elongate electrode, the plurality of arms and the support structure.

Clause 113. The method of clause 111, wherein the gap is sized to receive incised tissue along an incision formed with the elongate electrode.

Clause 114. The method of clause 110, wherein the support structure is operatively coupled to one or more actuators to move the elongate electrode in one or more directions.

Clause 115. The method of clause 114, wherein the one or more actuators moves the electrode with a variable velocity.

Clause 116. The method of clause 106, wherein the tensioning element is selected from the group consisting of a spring, a coil spring, a leaf spring, a torsion spring, a mesh, a hinge, and a living hinge.

Clause 117. The method of clause 106, wherein the elongate electrode comprises a first portion of an elongate filament and wherein the tensioning element comprises a second portion of the elongate filament shaped to tension the elongate electrode.

Clause 118. The method of clause 106, wherein an electrode assembly comprising a support structure is operatively coupled to a plurality of arms and the tensioning element, wherein the electrode assembly advances the electrode into tissue to incise the tissue.

Clause 119. The method of clause 106, wherein the electrode sequentially contacts a plurality of locations of the tissue to generate the incision.

Clause 120. The method of clause 119, wherein the plurality of locations comprises a plurality of discontiguous locations.

Clause 121. The method of clause 120, wherein the electrode vaporizes tissue in contact with the electrode at each of the plurality of discontiguous locations.

Clause 122. The method of clause 106, wherein the electrode generates a plurality of flashes of light energy at a plurality of locations while the electrode incises the tissue.

Clause 123. The method of clause 122, wherein the plurality of flashes of light energy comprise visible light energy comprising a wavelength within a range from about 400 nm to about 750 nm.

Clause 124. The method of clause 122, wherein each of the plurality of flashes of light energy comprises maximum distance across of no more than about 1 mm.

Clause 125. The method of clause 122, wherein the plurality of flashes is generated within a time interval of no more than about 250 µs and optionally no more than about 25 µs.

Clause 126. The method of clause 122, wherein the plurality of flashes is generated with an electrode movement distance of no more than about 100 µm and optionally no more than about 10 µm.

Clause 127. The method of clause 122, wherein the plurality of flashes of light is distributed at a plurality of non-overlapping regions.

Clause 128. The method of clause 127, wherein the plurality of non-overlapping regions is located along the elongate electrode.

Clause 129. The method of clause 122, wherein the plurality of flashes of light are generated at a first rate with a first velocity of the electrode and a second rate with a second velocity of the electrode, wherein the first rate is greater than the second rate when the first velocity is less than the second velocity and wherein the first rate is less than the second rate when the first velocity is greater than the second velocity.

Clause 130. The method of clause 129, wherein the plurality of flashes of light is generated at a substantially constant rate to within about 25% and wherein one or more of a pulse rate or a burst rate of a waveform to the elongate electrode is varied in response to the a varying velocity of the electrode to maintain the substantially constant rate.

Clause 131. The method of clause 106, wherein the elongate electrode comprises a filament and wherein the filament comprises one or more of a wire or a thread.

Clause 132. The method of clause 106, wherein the elongate electrode comprises a wire.

Clause 133. The method of clause 132, wherein a diameter of the wire is within a range from 5 µm to 200 µm, optionally from about 5 µm to about 100 µm, optionally from about 5 µm to about 50 µm, optionally from about 5 µm to about 25 µm, or optionally from about 5 µm to about 20 µm.

Clause 134. The method of clause 106, wherein the elongate electrode comprises a cross-sectional distance and wherein the cross-sectional distance comprises no more than about 25 µm.

Clause 135. The method of clause 106, wherein the elongate electrode operatively coupled to the tensioning element comprises a mechanical resonance frequency within a range from about 1 kHz to about 100 kHz and optionally within a range from about 2 kHz to about 50 kHz.

Clause 136. The method of clause 106, wherein the tensioning element tensions the elongate electrode with a force within a range from about 20 mN to about 2N and optionally within a range from about 50 mN to about 1N and further optionally within a range from about 100 mN to about 500 mN.

Clause 137. The method of clause 106, wherein the elongate electrode comprises a mass per unit length within a range from about 0.2 µg·mm-1 to about 3 µg·mm-1.

Clause 138. The method of clause 106, wherein elongate electrode comprises a material selected from the group consisting of tungsten, nitinol, steel, copper, brass, titanium, stainless steel, beryllium-copper alloy, cupronickel alloy, palladium, platinum, platinum-iridium, silver, and aluminum.

Clause 139. The method of clause 106, wherein elongate electrode comprises an axis along an elongate direction of the electrode and wherein the electrode incises tissue with movement in a direction transverse to the axis.

Clause 140. The method of clause 106, wherein elongate electrode incises tissue in a direction transverse to an elongate direction of the electrode at a velocity greater than about 1 m·s-1.

Clause 141. The method of clause 106, wherein elongate electrode incises tissue in a direction transverse to an elongate direction of the electrode at a velocity within a range from about 0.5 cm·s-1 to about 10 m·s-1 and optionally within a range from about 1 cm·s-1 to about 5 m·s-1.

Clause 142. The method of clause 106, wherein the electrode incises an area of tissue at a rate within a range from about 5 mm²·s-1 to about 50,000 mm²·s-1 and optionally within a range from about 500 mm²·s-1 to about 25,000 mm²·s-1.

Clause 143. The method of clause 106, wherein the electrical energy source delivers a waveform, wherein the waveform comprises one or more of a pulsatile waveform, a sinusoidal waveform, a square waveform, a sawtooth waveform, a triangular waveform, a fixed frequency waveform, a variable frequency waveform, or a gated waveform.

Clause 144. The method of clause 143, wherein the waveform comprises the sinusoidal waveform and wherein the sinusoidal waveform comprises a frequency within a range from about 0.5 MHz to about 2 MHz.

Clause 145. The method of clause 143, wherein the waveform comprises a combination of the sinusoidal waveform and the gated waveform and wherein the sinusoidal waveform comprises a frequency within a range from about 0.5 MHz to about 2 MHz and wherein the gated waveform comprises a gate frequency within a range from about 20 kHz to about 80 KHz and a duty cycle within a range from about 35% to about 100%.

Clause 146. The method of clause 106, wherein a controller is operatively coupled to the electrical energy source.

Clause 147. The method of clause 146, wherein the controller controls parameters of the electrical energy source by modulating the waveform using a parameter selected from the group consisting of a voltage, a current, a carrier frequency, a modulation frequency, a duty cycle, a power setpoint, a power limit, an energy per pulse setpoint, an energy per pulse limit, and a modulation envelope.

Clause 148. The method of clause 147, wherein the waveform comprises a pulsatile voltage waveform comprising pulses and a substantially constant frequency within a range from about 10 kHz to about 10 MHz and optionally within a range from about 0.5 MHz to about 2 MHz.

Clause 149. The method of clause 148, wherein the waveform provides an energy per pulse of within a range from about 0.5 µJ to about 50 µJ and optionally within a range from about 1 µJ to about 10 µJ.

Clause 150. The method of clause 149, wherein the controller modulates the substantially constant frequency waveform to produce bursts.

Clause 151. The method of clause 150, wherein a frequency of the bursts is within a range from about 100 Hz and about 3 MHz and optionally within a range from about 1 kHz to about 100 kHz.

Clause 152. The method of clause 151, wherein the waveform from the electrical energy source supplies an average power within a range from about 1 W to about 25 W.

Clause 153. The method of clause 110, wherein a translation element operatively coupled to the support structure directs the support structure along an axis of motion transverse to an elongate axis of the electrode.

Clause 154. The method of clause 153, wherein the translation element is selected from the group consisting of a translation stage, a linear stage, a rotary stage, a rail, a rod, a cylindrical sleeve, a screw, a roller screw, a travelling nut, a rack, a pinion, a belt, a chain, a linear motion bearing, a rotary motion bearing, a cam, a flexure, and a dovetail.

Clause 155. The method of clause 154, wherein an actuator operatively coupled to the translation element moves the support structure along an axis of motion.

Clause 156. The method of clause 155, wherein the translation element is manually actuated.

Clause 157. The method of clause 155, wherein the actuator is selected from the group consisting of a motor, a rotary motor, a squiggle motor, a linear motor, a solenoid, a rotary solenoid, a linear solenoid, a voice coil, a spring, a moving coil, a piezoelectric actuator, a pneumatic actuator, a hydraulic actuator, and a fluidic actuator.

Clause 158. The method of clause 110, wherein a portion of the support structure comprises a material selected from the group consisting of tungsten, nitinol, steel, copper, brass, titanium, stainless steel, beryllium-copper alloy, cupronickel alloy, palladium, platinum, platinum-iridium, silver, aluminum, polyimide, PTFE, polyethylene, polypropylene, polycarbonate, poly(methyl methacrylate), acrylonitrile butadiene styrene, polyamide, polylactide, polyoxymethylene, polyether ether ketone, polyvinyl chloride, polylactic acid, glass, and ceramic.

Clause 159. The method of clause 153, wherein the translation element comprises a first translation element having a first axis of motion and a second translation element having a second axis of motion different from the first axis of motion.

Clause 160. The method of clause 159, wherein the first and second translation elements are each selected from the group consisting of a translation stage, a linear stage, a rotary stage, a rail, a rod, a cylindrical sleeve, a screw, a roller screw, a travelling nut, a rack, a pinion, a belt, a chain, a linear motion bearing, a rotary motion bearing, a cam, a flexure, and a dovetail.

Clause 161. The method of clause 160, wherein a contact plate operatively coupled to the second translation element engages a portion of the tissue to shape the tissue prior to incising the tissue with the electrode.

Clause 162. The method of clause 106, wherein a contact plate operatively coupled to the elongate electrode engages a portion of a cornea to shape the cornea prior to incising the cornea with the electrode.

Clause 163. The method of clause 162, wherein the contact plate comprise a first contact plate have a first surface profile and a second contact plate having a second surface profile, a difference between the first surface profile and the second surface profile corresponding to a refractive correction of an eye to correct the refractive error of the eye.

Clause 164. The method of clause 162, wherein the contact plate comprises a free-form optical surface shaped to correct wavefront aberrations an eye.

Clause 165. The method of clause 162, wherein the contact plate comprises a plurality of independently adjustable actuators to shape the cornea.

Clause 166. The method of clause 165, wherein the contact plate comprises a plurality of plates operatively coupled to the independently adjustable actuators to shape the cornea.

Clause 167. The method of clause 166, wherein each of the plurality of plates is driven to a first position and a second position at each of a plurality of locations, a difference between the first position and the second position corresponding to a shape profile of tissue to be resected from the cornea to ameliorate refractive error of the eye.

Clause 168. The method of clause 167, wherein the plurality of locations comprises a plurality of two-dimensional locations and the shape profile comprises a three-dimensional tissue resection profile.

Clause 169. The method of clause 165, wherein the plurality of actuators comprises at least 10 actuators and optionally wherein the plurality of actuators comprises at least 16 actuators and optionally wherein the plurality of actuators comprises at least 42 actuators and optionally wherein the plurality of actuators comprises at least 100 actuators.

Clause 170. The method of clause 165, wherein the contact plate comprises a deformable membrane operatively coupled to the plurality of independently adjustable actuators.

Clause 171. The method of clause 165, wherein the contact plate comprises a first configuration for a first incision with the electrode along a first incision profile and a second configuration for a second incision with the electrode along a second incision profile and wherein a difference between the first incision profile and the second incision profile corresponds to a shape of a lenticule of tissue removed from the cornea to treat a refractive error of the eye.

Clause 172. The method of clause 162, wherein the contact plate is configured to correct one or more of sphere, cylinder, coma, spherical aberration, or trefoil of an eye.

Clause 173. The method of clause 162, wherein a suction element engages tissue retain the tissue in contact with the second translation element in a substantially fixed position while the first translation element moves the electrode to incise the tissue.

Clause 174. The method of clause 162, wherein sterile barrier is placed on the contact plate to maintain sterility of the eye.

Clause 175. The method of clause 174, wherein the sterile barrier comprises a thin conformal barrier to conform to the shape of the contact plate with the sterile barrier between the eye and the contact plate.

Clause 176. The method of clause 174, wherein the sterile barrier comprises a peel-and-stick sterile barrier.

Clause 177. The method of cluase 162, wherein: a length of the elongate electrode is within a range from about 6 mm to about 12 mm; the tissue comprises corneal tissue; the electrode comprises a wire having a diameter within a range from about 5 µm to about 20 µm; and wherein the tensioning element provides a tension to the electrode within a range from about 100 mN to about 500 mN.

Clause 178. A method to treat a refractive error of an eye, the method comprising: incising corneal tissue with an elongate electrode by providing electrical energy to the electrode; engaging a portion of a cornea to shape the cornea with a contact plate prior to incising the cornea with the electrode; and wherein a support structure moves the electrode relative to the plate and incises the corneal tissue with the electrode.

Clause 179. The method of clause 178, wherein a translation element operatively coupled to the support structure and the elongate electrode translates the electrode to incise the corneal tissue.

Clause 180. The method of clause 178, wherein the contact plate comprise a first contact plate have a first surface profile and a second contact plate having a second surface profile, a difference between the first surface profile and the second surface profile corresponding to a refractive correction of an eye to correct the refractive error of the eye.

Clause 181. The method of clause 178, wherein the contact plate comprises a free-form optical surface shaped to correct wavefront aberrations an eye.

Clause 182. The method of clause 178, wherein the contact plate comprises a plurality of independently adjustable actuators to shape the cornea.

Clause 183. The method of clause 182, wherein the contact plate comprises a plurality of plates operatively coupled to the independently adjustable actuators to shape the cornea.

Clause 184. The method of clause 183, wherein each of the plurality of plates is configured to be driven to a first position and a second position at each of a plurality of locations, a difference between the first position and the second position corresponding to a shape profile of tissue to be resected from the cornea to ameliorate refractive error of the eye.

Clause 185. The method of clause 184, wherein the plurality of locations comprises a plurality of two-dimensional locations and the shape profile comprises a three-dimensional tissue resection profile.

Clause 186. The method of clause 182, wherein the plurality of actuators comprises at least 10 actuators and optionally wherein the plurality of actuators comprises at least 16 actuators and optionally wherein the plurality of actuators comprises at least 42 actuators and optionally wherein the plurality of actuators comprises at least 100 actuators.

Clause 187. The method of clause 182, wherein the contact plate comprises a deformable membrane operatively coupled to the plurality of independently adjustable actuators.

Clause 188. The method of clause 182, wherein the contact plate comprises a first configuration for a first incision with the electrode along a first incision profile and a second configuration for a second incision with the electrode along a second incision profile and wherein a difference between the first incision profile and the second incision profile corresponds to a shape of a lenticule of tissue to be removed from the cornea to treat a refractive error of the eye.

Clause 189. The method of clause 178, wherein the contact plate is configured to correct one or more of sphere, cylinder, coma, spherical aberration, or trefoil of an eye.

Clause 190. The method of clause 178, wherein a suction element engages the corneal tissue retain the corneal tissue in contact with the second translation element in a substantially fixed position while the first translation element moves the electrode to incise the tissue.

Clause 191. The method of clause 178, wherein a sterile barrier is placed on the contact plate to maintain sterility of the eye.

Clause 192. The method of clause 191, wherein the sterile barrier comprises a thin conformal barrier to conform to the shape of the contact plate with the sterile barrier between the eye and the contact plate.

Clause 193. The method of clause 191, wherein the sterile barrier comprises a peel-and-stick sterile barrier.

Clause 194. The method of clause 178, wherein: a length of the elongate electrode is within a range from 6 mm to 12 mm; the electrode comprises a wire having a diameter within a range from 5 µm to 20 µm; and wherein the tensioning element provides a tension to the electrode within a range from 100 mN to 500 mN.

Clause 195. A method of treating a refractive error of an eye, the method comprising: inserting an elongate electrode into a cornea of the eye; incising the cornea with the electrode to define a lenticle of corneal tissue within a pocket; and removing the lenticle; wherein the lenticle comprises a shape profile corresponding to treatment of the refractive error.

Clause 196. The method of clause 195, wherein the electrode is moved with a first movement to define a first surface on a first side of the lenticle and moved with a second movement to define a second surface on a second side of the lenticle.

Clause 197. The method of clause 195, wherein the electrode is advanced distally to define a first surface on a first side of the lenticle and drawn proximally to define a second surface on a second side of the lenticle.

Clause 198. The method of clause 197, wherein a gap extends between the elongate electrode and the support structure and wherein the gap is sized to receive tissue and wherein tissue extending into the gap is incised when the electrode is drawn proximally.

Clause 199. The method of clause 195, wherein a contact plate comprises a first configuration to define a first surface on a first side of the lenticule and a second configuration to define a second surface on a second side of the lenticule.

Clause 200. The method of clause 195, wherein a first contact plate comprises a first shape profile to define a first surface on a first side of the lenticule and a second shape profile to define a second surface on a second side of the lenticule.

Clause 201. The method of clause 195, wherein the shape profile comprises a thickness profile.

Clause 202. The system or method of any one of the preceding clauses, further comprising: a processor operatively coupled to the elongate electrode to move the elongate electrode to incise tissue.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A system for incising tissue with a plasma, comprising:
   an elongate electrode, the elongate electrode configured to flex and generate the plasma to incise the tissue;
   an electrical energy source operatively coupled to the elongate electrode and configured to provide electrical energy to the elongate electrode to generate the plasma;
   a tensioning element operatively coupled to the elongate electrode, the tensioning element configured to provide tension to the elongate electrode to allow the elongate electrode to flex in response to the elongate electrode engaging the tissue and generating the plasma; and
   a contact surface operatively coupled to the elongate electrode, the contact surface configured to engage a portion the tissue to shape the tissue prior to incising the tissue with the elongate electrode, wherein the contact surface comprises a plurality of independently adjustable actuators to shape the tissue.

2. The system of claim 1, further comprising a plurality of arms operatively coupled to the elongate electrode and the tensioning element.

3. The system of claim 2, wherein the elongate electrode is unsupported between two arms of the plurality of arms.

4. The system of claim 2, wherein the elongate electrode is configured to vibrate transversely to an elongate axis of the elongate electrode.

5. The system of claim 1, wherein the contact surface comprises a first contact surface having a first surface profile and a second contact surface having a second surface profile, a difference between the first surface profile and the second surface profile corresponding to a shape profile of a volume of tissue to be removed.

6. The system of claim 1, wherein the contact surface comprises a free-form optical surface.

7. The system of claim 1, wherein the contact surface comprises a deformable membrane operatively coupled to the plurality of independently adjustable actuators.

8. The system of claim 1, further comprising a sterile barrier for placement on the contact surface to maintain sterility of the tissue.

9. The system of claim 8, wherein the sterile barrier comprises a barrier configured to conform to the shape of the contact surface with the sterile barrier between the tissue and the contact surface.

10. The system of claim 8, wherein the sterile barrier comprises a peel-and-stick sterile barrier.

11. The system of claim 1, wherein:
    a length of the elongate electrode is within a range from about 6 mm to about 12 mm;
    the tissue comprises ocular tissue;
    the elongate electrode comprises a wire having a diameter within a range from about 5 µm to about 20 µm; and
    wherein the tensioning element is configured to provide a tension to the elongate electrode within a range from about 100 mN to about 500 mN.

12. The system of claim 1, further comprising:
    a processor operatively coupled to the elongate electrode, the processor configured with instructions to advance the elongate electrode distally and draw the elongate electrode proximally.

13. The system of claim 12, wherein:
    the elongate electrode is sized for insertion into the tissue;
    the processor is configured with instructions to incise the tissue with the elongate electrode to define a volume of incised tissue; and
    wherein the volume of incised tissue comprises a shape profile.

14. The system of claim 13, wherein the processor is configured with instructions to move the elongate electrode with a first movement to define a first surface on a first side of the volume of incised tissue and move with a second movement to define a second surface on a second side of the volume of incised tissue.

15. The system of claim 13, wherein the processor is configured with instructions to advance the elongate electrode distally to define a first surface on a first side of the volume of incised tissue and to draw the elongate electrode proximally to define a second surface on a second side of the volume of incised tissue.

16. The system of claim 15, wherein a gap extends between the elongate electrode and a support structure and wherein the gap is sized to receive tissue and wherein tissue extending into the gap is incised when the elongate electrode is drawn proximally.

17. The system of claim 13, the contact surface comprises a first configuration to define a first surface on a first side of the volume of tissue and a second configuration to define a second surface on a second side of the volume of tissue.

18. The system of claim 13, wherein the contact surface comprises a first shape profile to define a first surface on a first side of the volume of tissue and a second shape profile to define a second surface on a second side of the volume of tissue.

19. The system of claim 13, wherein the shape profile comprises a thickness profile.

* * * * *